(12) United States Patent
Lee et al.

(10) Patent No.: US 9,391,282 B2
(45) Date of Patent: Jul. 12, 2016

(54) HETEROCYCLIC COMPOUND AND ORGANIC LIGHT-EMITTING DIODE INCLUDING THE SAME

(71) Applicant: SAMSUNG DISPLAY CO., LTD., Yongin, Gyeonggi-Do (KR)

(72) Inventors: Eun-Young Lee, Yongin (KR); Seok-Hwan Hwang, Yongin (KR); Young-Kook Kim, Yongin (KR); Jun-Ha Park, Yongin (KR); Hye-Jin Jung, Yongin (KR); Jin-O Lim, Yongin (KR); Sang-Hyun Han, Yongin (KR); Eun-Jae Jeong, Yongin (KR); Soo-Yon Kim, Yongin (KR); Jong-Hyuk Lee, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 303 days.

(21) Appl. No.: 13/921,168

(22) Filed: Jun. 18, 2013

(65) Prior Publication Data

US 2014/0239260 A1    Aug. 28, 2014

(30) Foreign Application Priority Data

Feb. 22, 2013  (KR) .................. 10-2013-0019374

(51) Int. Cl.
| | | |
|---|---|---|
| H01L 51/50 | (2006.01) | |
| H01L 51/00 | (2006.01) | |
| C07D 401/14 | (2006.01) | |
| C07D 401/04 | (2006.01) | |
| C07D 401/12 | (2006.01) | |
| C07D 405/12 | (2006.01) | |
| C07D 409/12 | (2006.01) | |
| C07D 409/14 | (2006.01) | |
| C07D 403/12 | (2006.01) | |
| C07D 401/10 | (2006.01) | |
| C07D 405/10 | (2006.01) | |
| C07D 409/10 | (2006.01) | |
| C07D 209/56 | (2006.01) | |

(52) U.S. Cl.
CPC .......... *H01L 51/0072* (2013.01); *C07D 209/56* (2013.01); *C07D 401/04* (2013.01); *C07D 401/10* (2013.01); *C07D 401/12* (2013.01); *C07D 401/14* (2013.01); *C07D 403/12* (2013.01); *C07D 405/10* (2013.01); *C07D 405/12* (2013.01); *C07D 409/10* (2013.01); *C07D 409/12* (2013.01); *C07D 409/14* (2013.01); *H01L 51/0052* (2013.01); *H01L 51/0058* (2013.01); *H01L 51/0067* (2013.01); *H01L 51/0073* (2013.01); *H01L 51/0074* (2013.01)

(58) Field of Classification Search
CPC .................................... C07D 209/56
See application file for complete search history.

(56) References Cited

U.S. PATENT DOCUMENTS

| | | |
|---|---|---|
| 3,968,051 A | 7/1976 | Stamm et al. |
| 7,053,255 B2 | 5/2006 | Ikeda et al. |
| 7,233,019 B2 | 6/2007 | Ionkin et al. |
| 2005/0002857 A1* | 1/2005 | Pez ............... C01B 3/0015 423/648.1 |
| 2005/0156164 A1 | 7/2005 | Sotoyama |

FOREIGN PATENT DOCUMENTS

| | | | |
|---|---|---|---|
| GB | WO 2011116866 A1 * | 9/2011 | ........... C08G 61/123 |
| KR | 10-2006-0006760 A | 1/2006 | |
| KR | 10-2010-0130068 A | 12/2010 | |
| WO | WO 2010/140802 A1 | 12/2010 | |

OTHER PUBLICATIONS

2009 Fall Assembly and Symposium, symposium; Oct. 8-9, 2009, Gwanju Institute of Science and Technology, Oryong Hall, vol. 34, No. 2; URL: http://www.sigmaaldrich.com/catalog/search?interface=All&term=4H-Benzo%5Bdef%5Dcarbazole&lang=ko&region=KR&focus=product&N=0+220003048+219853163+219853286&mode=match%20partialmax, 2 pages.

\* cited by examiner

*Primary Examiner* — Jennifer Chriss
*Assistant Examiner* — Dylan Kershner
(74) *Attorney, Agent, or Firm* — Lewis Roca Rothgerber Christie LLP

(57) ABSTRACT

A heterocyclic compound is represented by Formula 1. The heterocyclic compound may be used in an organic layer of an organic light-emitting diode. An organic light-emitting diode includes a first electrode, a second electrode and an organic layer, and the organic layer includes the heterocyclic compound represented by Formula 1. The organic light-emitting diode may be used in a flat panel display device, in which the first electrode of the organic light-emitting diode may be electrically connected to a source or drain electrode of a thin film transistor.

<Formula 1>

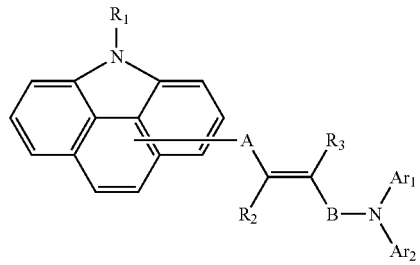

20 Claims, 1 Drawing Sheet

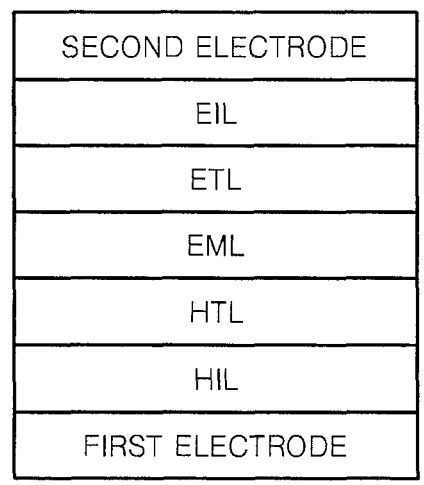

HETEROCYCLIC COMPOUND AND ORGANIC LIGHT-EMITTING DIODE INCLUDING THE SAME

CROSS-REFERENCE TO RELATED APPLICATION

This application claims priority to and the benefit of Korean Patent Application No. 10-2013-0019374, filed on Feb. 22, 2013 in the Korean Intellectual Property Office, the entire content of which is incorporated herein by reference.

BACKGROUND

1. Technical Field

The present invention relates to a heterocyclic compound and an organic light-emitting diode including the same.

2. Description of the Related Art

Organic light-emitting diodes (OLEDs) are self-emitting diodes having advantages such as wide viewing angles, good contrast, quick response speeds, high brightness, and good driving voltages. Also, OLEDs can provide multicolored images.

A typical diode has a structure including a substrate, an anode formed on the substrate, and a hole transport layer (HTL), an emission layer (EML), an electron transport layer (ETL), and a cathode sequentially stacked on the substrate. The HTL, the EML, and the ETL are organic thin films formed of organic compounds.

An operating principle of an OLED having the above-described structure is as follows. When a voltage is applied between the anode and the cathode, holes injected from the anode move to the EML via the HTL, and electrons injected from the cathode move to the EML via the ETL. The holes and electrons (carriers) recombine in the EML to generate excitons. When the excitons drop from an excited state to a ground state, light is emitted.

While conventional OLEDs may use monomolecular materials, there is ongoing demand for a material having improved electrical stability, high charge-transferring and light-emitting abilities, good emission capability, a high glass transition temperature, and that is capable of preventing crystallization.

SUMMARY

Embodiments of the present invention provide a heterocyclic compound and an organic light-emitting diode (OLED) including the same. The compound has good electrical properties, high charge-transferring abilities, and high light-emitting ability. The compound, which is a material having a high glass transition temperature and that is capable of preventing crystallization, can be effectively used as an electron-transporting material or an electron-injecting material suitable for fluorescent and phosphorescent diodes of any color, e.g., red, green, blue, or white. Therefore, a light-emitting diode having high efficiency, low driving voltage, high luminance, and a long lifetime may be manufactured using the compound.

According to an aspect of the present invention, a heterocyclic compound is represented by Formula 1 below:

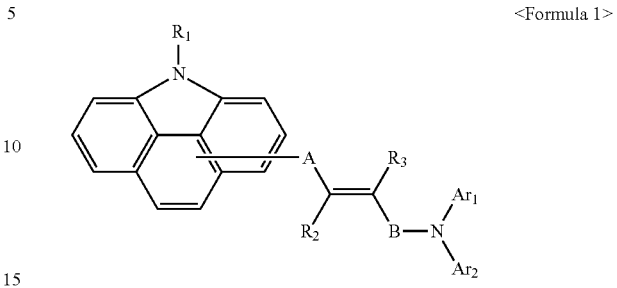

<Formula 1>

In Formula 1, A and B may each independently be a single bond or a bivalent linker that is a substituted or unsubstituted $C_6$-$C_{30}$ arylene group, a substituted or unsubstituted $C_2$-$C_{30}$ heteroarylene group, or a substituted or unsubstituted $C_6$-$C_{30}$ condensed polycyclic group.

$R_1$, $R_2$, and $R_3$ may each independently be a hydrogen atom, a deuterium atom, a substituted or unsubstituted $C_1$-$C_{60}$ alkyl group, a substituted or unsubstituted $C_3$-$C_{60}$ cycloalkyl group, a substituted or unsubstituted $C_6$-$C_{60}$ aryl group, a substituted or unsubstituted $C_2$-$C_{60}$ heteroaryl group, a substituted or unsubstituted $C_6$-$C_{30}$ condensed polycyclic group, a fluoro group, or a cyano group.

$Ar_1$ and $Ar_2$ may each independently be a substituted or unsubstituted $C_6$-$C_{30}$ aryl group, a substituted or unsubstituted $C_2$-$C_{30}$ heteroaryl group, or a substituted or unsubstituted $C_6$-$C_{30}$ condensed polycyclic group.

According to another aspect of the present invention, an OLED includes a first electrode, a second electrode, and an organic layer between the first electrode and the second electrode. The organic layer includes the compound of Formula 1 above.

According to another aspect of the present invention, the OLED is provided in a flat panel display device, and the first electrode on the substrate of the OLED is electrically connected to a source electrode or a drain electrode of a thin-film transistor (TFT).

BRIEF DESCRIPTION OF THE DRAWING

The above and other features and advantages of the present invention will become more apparent by reference to the following detailed description when considered in conjunction with the attached drawing in which:

FIG. 1 is a schematic view of a structure of an organic light-emitting diode (OLED) according to an embodiment of the present invention.

DETAILED DESCRIPTION

As used herein, the term "and/or" includes any and all combinations of one or more of the associated listed items. Expressions such as "at least one of," when preceding a list of elements, modify the entire list of elements and do not modify the individual elements of the list.

According to an aspect of the present invention, a heterocyclic compound is represented by Formula 1 below:

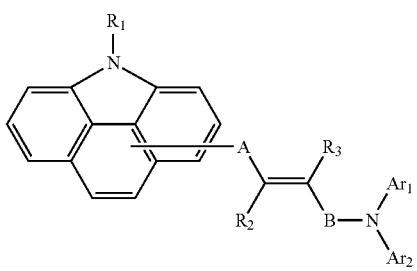

<Formula 1>

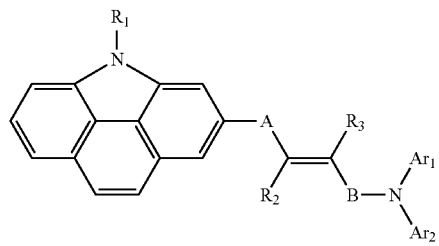

<Formula 3>

In Formula 1, A and B may each independently be a single bond or a bivalent linker that is a substituted or unsubstituted $C_6$-$C_{30}$ arylene group, a substituted or unsubstituted $C_2$-$C_{30}$ heteroarylene group, or a substituted or unsubstituted $C_6$-$C_{30}$ condensed polycyclic group.

$R_1$, $R_2$, and $R_3$ may each independently be a hydrogen atom, a deuterium atom, a substituted or unsubstituted $C_1$-$C_{60}$ alkyl group, a substituted or unsubstituted $C_3$-$C_{60}$ cycloalkyl group, a substituted or unsubstituted $C_6$-$C_{60}$ aryl group, a substituted or unsubstituted $C_2$-$C_{60}$ heteroaryl group, a substituted or unsubstituted $C_6$-$C_{30}$ condensed polycyclic group, a fluoro group, or a cyano group.

$Ar_1$ and $Ar_2$ may each independently be a substituted or unsubstituted $C_6$-$C_{30}$ aryl group, a substituted or unsubstituted $C_2$-$C_{30}$ heteroaryl group, or a substituted or unsubstituted $C_6$-$C_{30}$ condensed polycyclic group.

According to embodiments of the present invention, the compound of Formula 1 may function as a light-emitting material of the OLED. For example, the compound of Formula 1 may be effectively used as a blue fluorescent dopant.

Also, the compound of Formula 1 above has a high glass transition temperature (Tg) or melting point due to the introduction of the heterocyclic group. Therefore, the compound of Formula 1 above increases the thermal resistance of the OLED and the high-temperature resistance against Joule's heat that is generated in the organic layer, between organic layers, or between the organic layer and a metal electrode. The OLED manufactured using the heterocyclic compound has improved advantages such as high durability during storage or operation.

In some embodiments, the compound of Formula 1 above may be represented by Formula 2 or Formula 3 below:

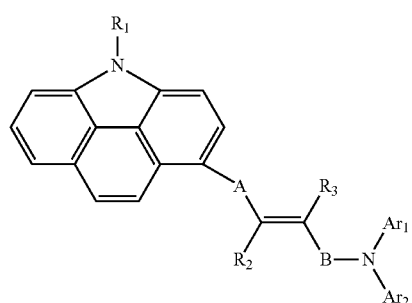

<Formula 2>

In Formulae 2 and 3, the definitions of the substituents are the same as in Formula 1 above.

In some embodiments, $Ar_1$ and $Ar_2$ in Formula 1 above may combine with each other or adjacent substituents to form a ring.

The substituents in the compound of Formula 1 above will be described in more detail.

In some embodiments, $R_1$ in Formula 1 above may be a substituted or unsubstituted $C_1$-$C_{30}$ alkyl group, or a compound represented by Formula 2a or Formula 2b below:

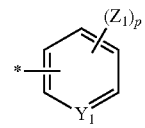

2a

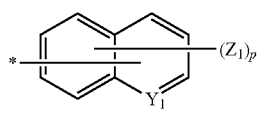

2b

In Formulas 2a and 2b, $Z_1$ may be a hydrogen atom, a deuterium atom, a halogen atom, —CN, a substituted or unsubstituted $C_1$-$C_{20}$ alkyl group, a substituted or unsubstituted $C_6$-$C_{20}$ aryl group, or a substituted or unsubstituted $C_6$-$C_{20}$ heteroaryl group.

$Y_1$ may be CH or N.

p may be an integer from 1 to 6.

* may be a binding site.

In some other embodiments, $R_2$ and $R_3$ in Formula 1 above may each independently be a hydrogen atom, a deuterium atom, a substituted or unsubstituted $C_1$-$C_{30}$ alkyl group, or a compound represented by Formula 3a below:

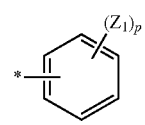

3a

In Formula 3a, $Z_1$ may be a hydrogen atom, a deuterium atom, a halogen atom, —CN, a substituted or unsubstituted $C_1$-$C_{20}$ alkyl group, a substituted or unsubstituted $C_6$-$C_{20}$ aryl group, or a substituted or unsubstituted $C_6$-$C_{20}$ heteroaryl group.

p may be an integer from 1 to 5.

* may be a binding site.

In some other embodiments, $Ar_1$ and $Ar_2$ in Formula 1 may each independently be one of the compounds represented by Formulas 4a to 4d below:

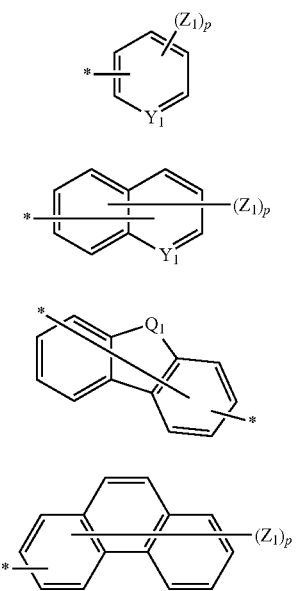

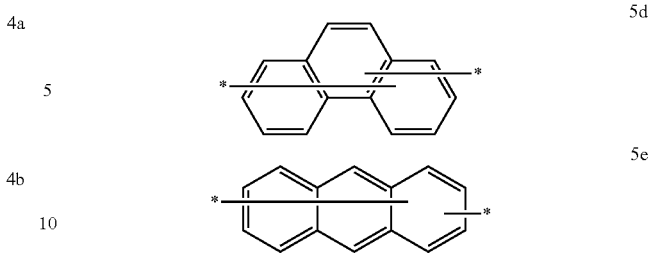

In Formulas 4a to 4d, $Z_1$ may be a hydrogen atom a deuterium atom, a halogen atom, —CN, a substituted or unsubstituted $C_1$-$C_{20}$ alkyl group, a substituted or unsubstituted $C_6$-$C_{20}$ aryl group, or a substituted or unsubstituted $C_6$-$C_{20}$ heteroaryl group.

$Y_1$ may be CH or N.

$Q_1$ may be a linker represented by —C($R_{30}$)($R_{31}$)—, —S—, or —O—.

$R_{30}$ and $R_{31}$ may each independently be a hydrogen atom, a deuterium atom, a substituted or unsubstituted $C_1$-$C_{20}$ alkyl group, a substituted or unsubstituted $C_5$-$C_{20}$ aryl group, or a substituted or unsubstituted $C_6$-$C_{20}$ condensed polycyclic group.

p may be an integer from 1 to 9.

* may be a binding site.

In some other embodiments, A and B in Formula 1 above may each independently be a single bond, one of the compounds represented by Formulas 5a to 5e below, or a linker connecting at least two of the compounds represented by Formulas 5a to 5e below.

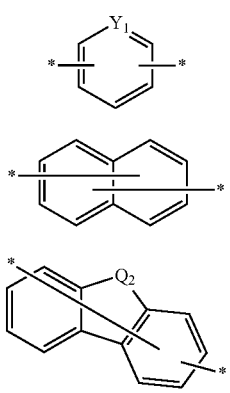

In Formulas 5a to 5e, $Y_1$ may be CH or N.

$Q_2$ may be a linker represented by —C($R_{30}$)($R_{31}$)—, —S—, or —O—.

$R_{30}$ and $R_{31}$ may each independently be a hydrogen atom, a deuterium atom, a substituted or unsubstituted $C_1$-$C_{20}$ alkyl group, a substituted or unsubstituted $C_5$-$C_{20}$ aryl group, or a substituted or unsubstituted $C_6$-$C_{20}$ condensed polycyclic group.

* may be a binding site.

Hereinafter, the definition of representative substituents used herein will be described. However, the numbers of carbons in a substituent are non-limited, and thus, the substituent characteristics are not limited. The substituents not defined herein are defined as substituents generally known to one of ordinary skill in the art.

The unsubstituted $C_1$-$C_{60}$ alkyl group, as used herein, refers to a linear or branched alkyl group. Non-limiting examples of the unsubstituted $C_1$-$C_{60}$ alkyl group include a methyl group, an ethyl group, a propyl group, an iso-butyl group, a sec-butyl group, a pentyl group, an iso-amyl group, a hexyl group, a heptyl group, an octyl group, a nonanyl group, and a dodecyl group. The substituted $C_1$-$C_{60}$ alkyl group refers to the substitution of at least one hydrogen atom of the unsubstituted $C_1$-$C_{60}$ alkyl group with a deuterium atom, a halogen atom, a hydroxyl group, a nitro group, a cyano group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_2$-$C_{60}$ alkenyl group refers to an unsubstituted alkenyl group having at least one carbon-carbon double bond in the center or at a terminal end thereof. Non-limiting examples of the unsubstituted $C_2$-$C_{60}$ alkenyl group include an ethenyl group, a propenyl group, a butenyl group, and the like. The substituted $C_2$-$C_{60}$ alkenyl group refers to the substitution of at least one hydrogen atom of the unsubstituted alkenyl group with the substituents described above in connection with the substituted alkyl group.

The unsubstituted $C_2$-$C_{60}$ alkynyl group refers to an unsubstituted alkynyl group having at least one carbon-carbon triple bond in the center or at a terminal end thereof. Non-limiting examples of the unsubstituted $C_2$-$C_{60}$ alkynyl group include acetylene, propylene, phenylacetylene, naphthylacetylene, isopropylacetylene, t-butylacetylene, diphenylacetylene, and the like. The substituted $C_2$-$C_{60}$ alkynyl group refers to the substitution of at least one hydrogen atom of the unsubstituted $C_2$-$C_{60}$ alkynyl group with the substituents described above in connection with the substituted alkyl group.

The unsubstituted $C_3$-$C_{60}$ cycloalkyl group refers to an alkyl group having a $C_3$-$C_{60}$ ring. The substituted $C_3$-$C_{60}$ cycloalkyl group refers to the substitution of at least one hydrogen atom of the $C_3$-$C_{60}$ cycloalkyl group with the substituents described above in connection with the $C_1$-$C_{60}$ alkyl group.

The unsubstituted $C_1$-$C_{60}$ alkoxy group is represented by —OA where A is an unsubstituted $C_1$-$C_{60}$ alkyl group, as described above. Non-limiting examples of the unsubstituted $C_1$-$C_{60}$ alkoxy group include a methoxy group, an ethoxy group, a propoxy group, an isopropyloxy group, a butoxy group, a pentoxy group, and the like. The substituted $C_1$-$C_{60}$ alkoxy group refers to the substitution of at least one hydrogen atom of the unsubstituted alkoxy group with the substituents described above in connection with the substituted alkyl group.

The unsubstituted $C_6$-$C_{60}$ aryl group refers to a carbocyclic aromatic system including at least one ring. When the unsubstituted $C_6$-$C_{60}$ aryl group has two or more rings, the rings may be fused to each other or linked to each other by a single bond. For example, the 'aryl' group may include an aromatic system such as phenyl, naphthyl, and anthracenyl. Also, the substituted $C_6$-$C_{60}$ aryl group refers to the substitution of at least one hydrogen atom of the aryl group with the substituents described above in connection with the $C_1$-$C_{60}$ alkyl group.

Non-limiting examples of the substituted or unsubstituted $C_6$-$C_{60}$ aryl group include a phenyl group, a $C_1$-$C_{10}$ alkylphenyl group (i.e., an ethylphenyl group), a biphenyl group, a $C_1$-$C_{10}$ alkylbiphenyl group, a $C_1$-$C_{10}$ alkoxybiphenyl group, an o-, m-, or p-toryl group, an o-, m-, or p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a $C_1$-$C_{10}$ alkylnaphthyl group (i.e., a methylnaphthyl group), a $C_1$-$C_{10}$ alkoxynaphthyl group (i.e., a methoxynaphthyl group), an anthracenyl group, an azulenyl group, a heptalenyl group, an acenaphthalenyl group, a phenalenyl group, a fluorenyl group, an anthraquinolyl group, a methylanthryl group, a phenanthryl group, a triphenylene group, a pyrenyl group, a chrysenyl group, an ethyl-chrysenyl group, a picenyl group, a perylenyl group, a pentaphenyl group, a pentacenyl group, a tetraphenylenyl group, a hexaphenyl group, a hexacenyl group, a rubicenyl group, a coronenyl group, a trinaphthalenyl group, a heptaphenyl group, a heptacenyl group, a pyranthrenyl group, an ovalenyl group, and the like.

The unsubstituted $C_2$-$C_{60}$ heteroaryl group, as used herein, refers to an aryl group including one, two, three, or four hetero atoms selected from N, O, P, or S. When the unsubstituted $C_2$-$C_{60}$ heteroaryl group has two or more rings, the rings may be fused to each other or linked to each other by a single bond. Non-limiting examples of the unsubstituted $C_4$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolyl group, an isoquinolyl group, and a dibenzothiophene group, and the like. In addition, the substituted $C_2$-$C_{60}$ heteroaryl group refers to the substitution of at least one hydrogen atom of the heteroaryl group with the substituents described above in connection with the unsubstituted $C_1$-$C_{60}$ alkyl group.

The unsubstituted $C_5$-$C_{60}$ aryloxy group is a group represented by —$OA_1$, where $A_1$ is a $C_5$-$C_{60}$ aryl group. Non-limiting examples of the aryloxy group include a phenoxy group, and the like. The substituted $C_5$-$C_{60}$ aryloxy group refers to the substitution of at least one hydrogen atom of the aryloxy group with the substituents described above in connection with the unsubstituted $C_1$-$C_{60}$ alkyl group.

The unsubstituted $C_5$-$C_{60}$ arylthio group is a group represented by —$SA_1$, where $A_1$ is a $C_5$-$C_{60}$ aryl group. Non-limiting examples of the arylthio group include a benzenethio group, a naphthylthio group, and the like. The substituted $C_5$-$C_{60}$ arylthio group refers to the substitution of at least one hydrogen atom of the arylthio group with the substituents described above in connection with the unsubstituted $C_1$-$C_{60}$ alkyl group.

The unsubstituted $C_6$-$C_{60}$ condensed polycyclic group, as used herein, refers to either: i) a substituent including at least two rings in which at least one aromatic ring and/or at least one non-aromatic ring are fused to each other; or ii) a substituent having an unsaturated group within a ring, but that is unable to form a conjugated structure. Therefore, the unsubstituted $C_6$-$C_{60}$ condensed polycyclic group is distinct from the aryl group or the heteroaryl group as it has a non-aromatic component.

Non-limiting examples of the compound of Formula 1 include the following compounds represented by Formulas 1 to 137 below:

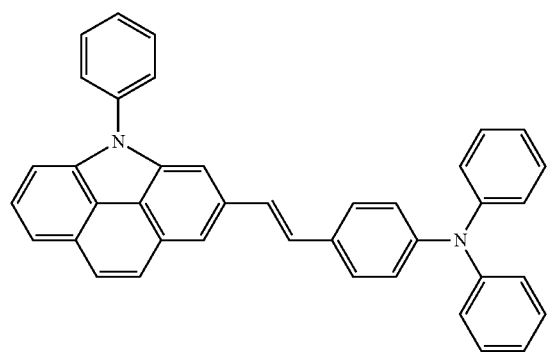

1

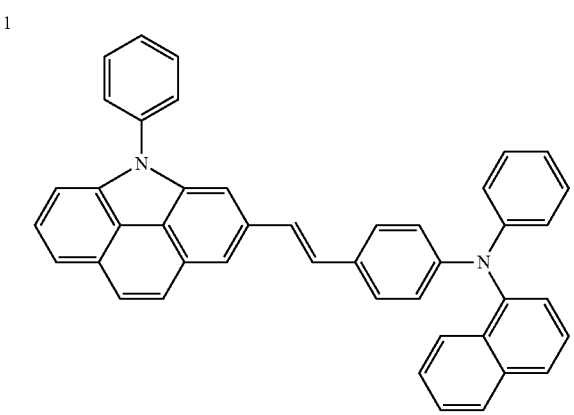

2

-continued
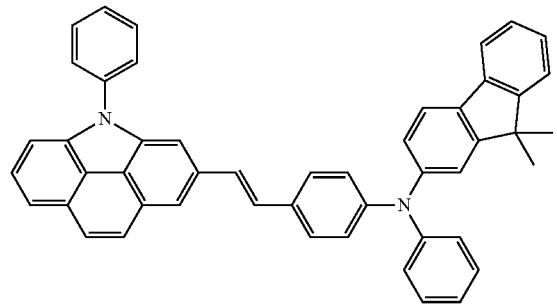
3
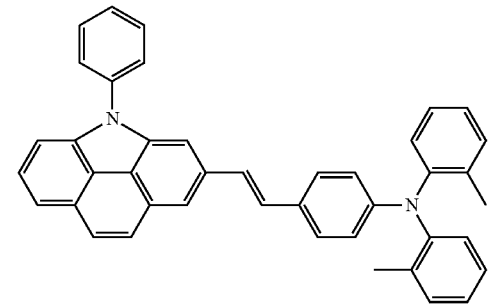
4
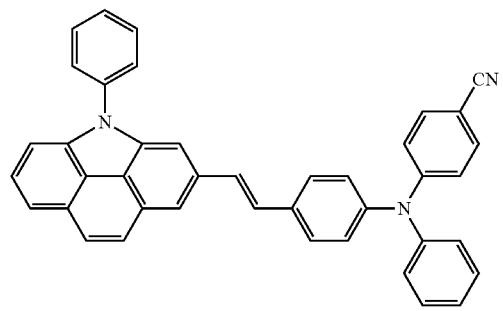
5
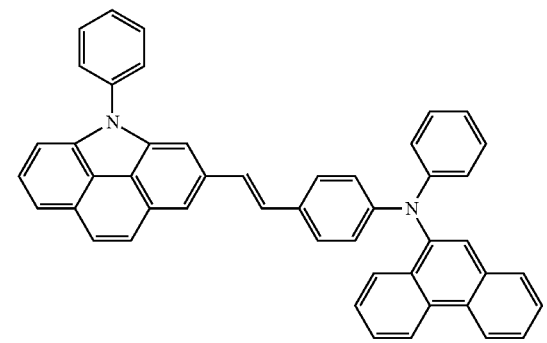
6
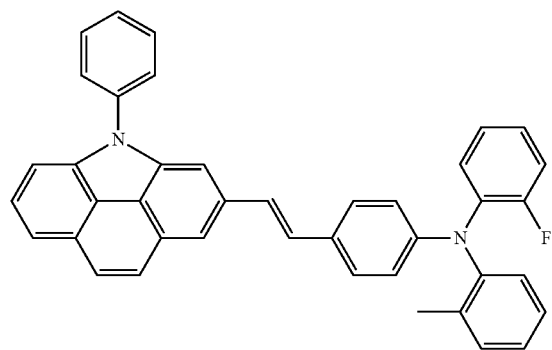
7
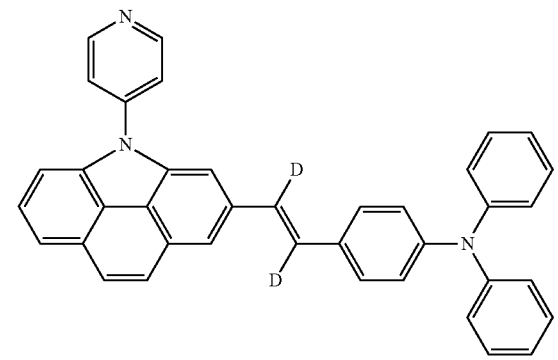
8
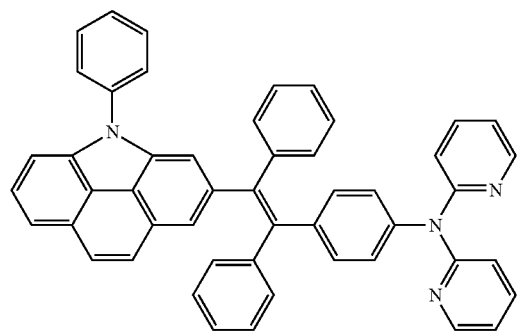
9
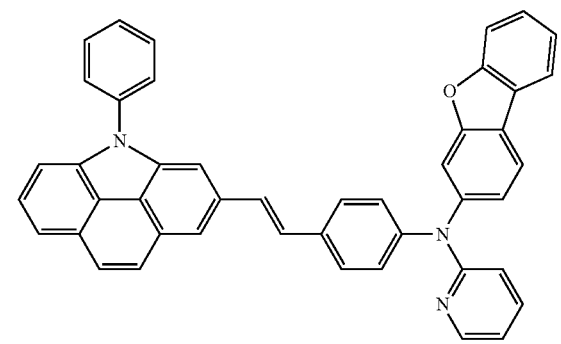
10

-continued
11
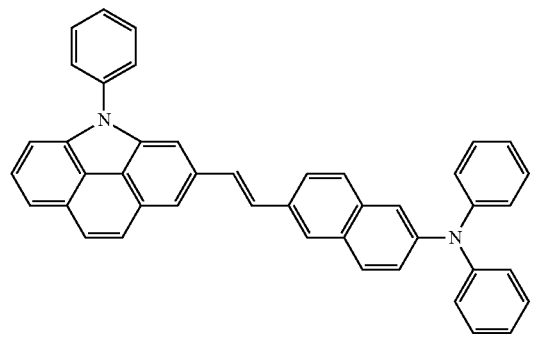
12
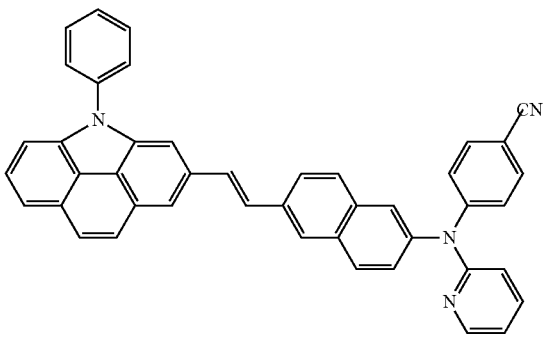
13
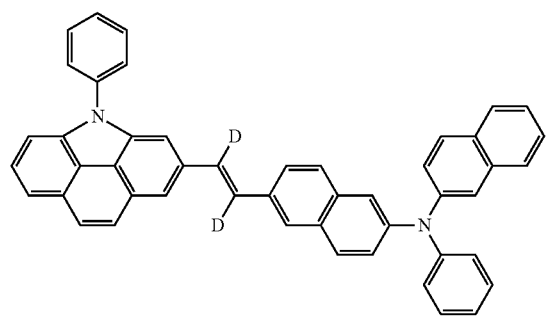
14
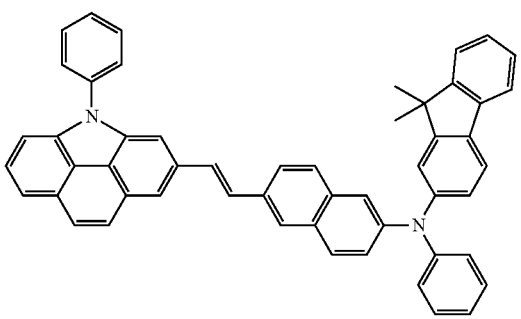
15
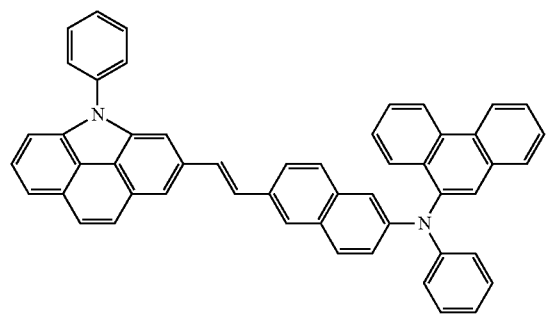
16
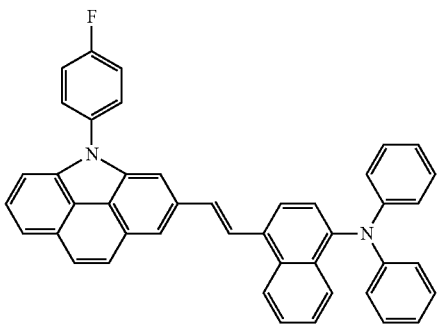
17
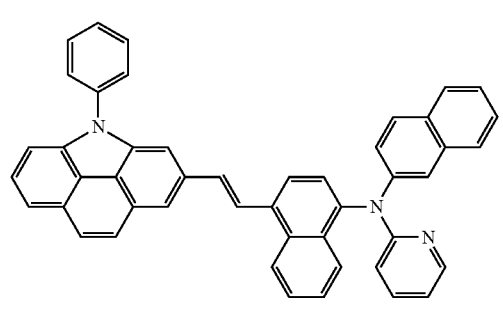
18
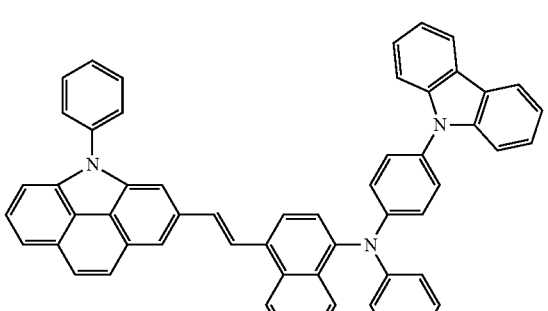

-continued
19
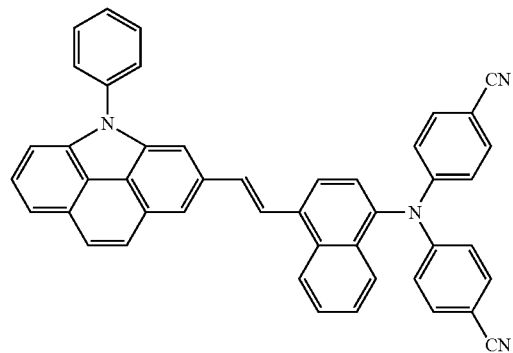
20
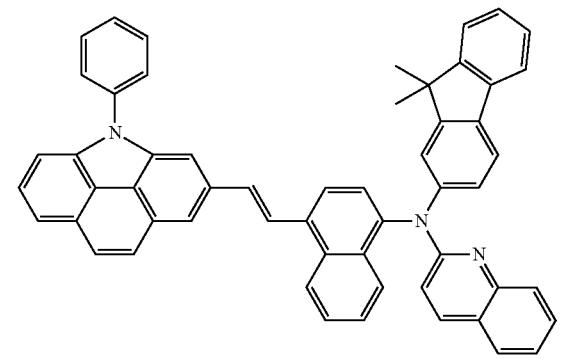
21
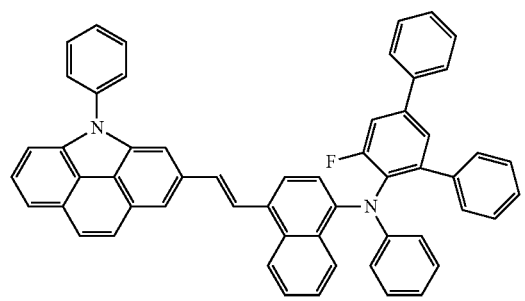
22
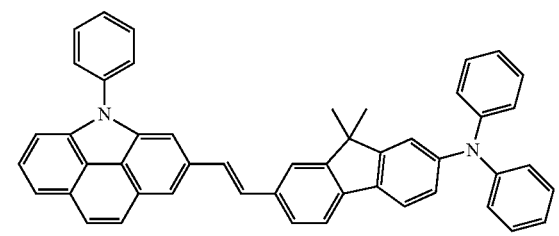
23
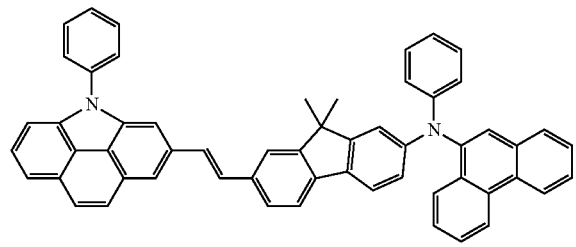
24
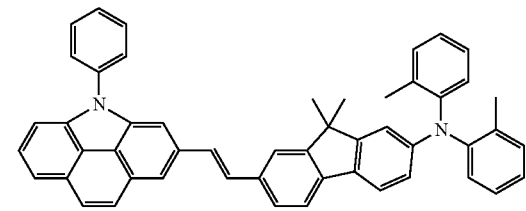
25
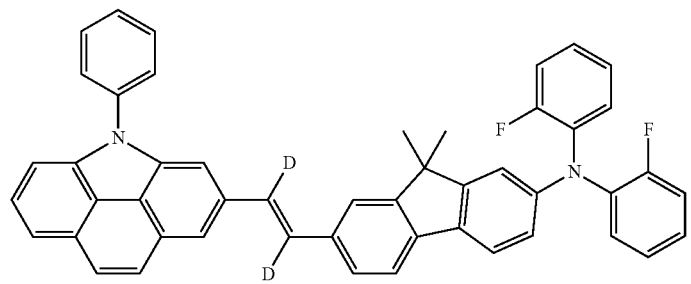
26
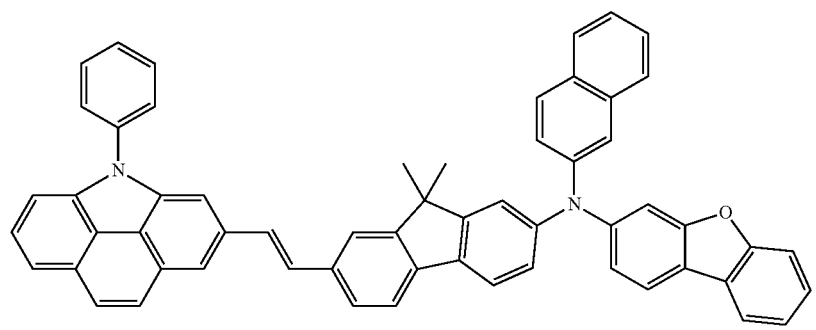

-continued
27
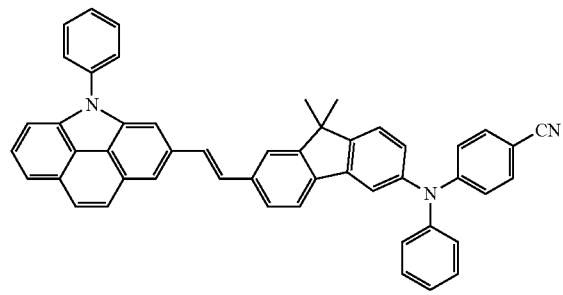
28
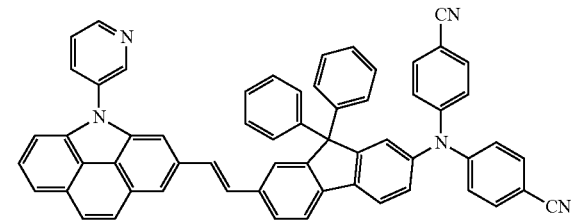
29
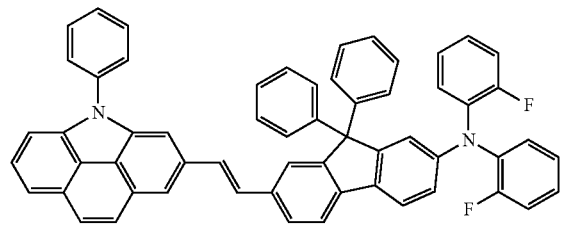
30
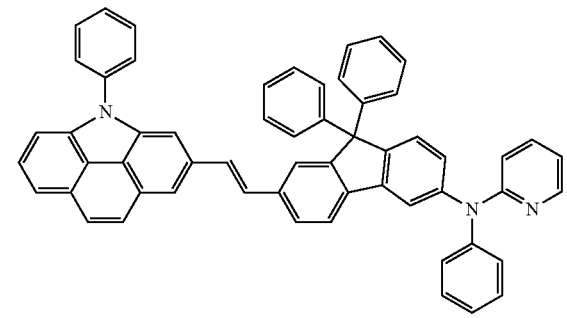
31
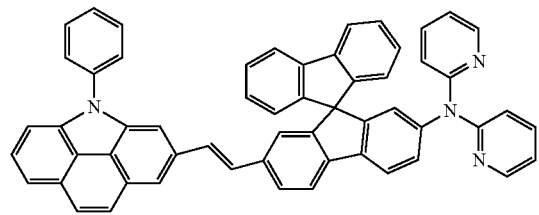
32
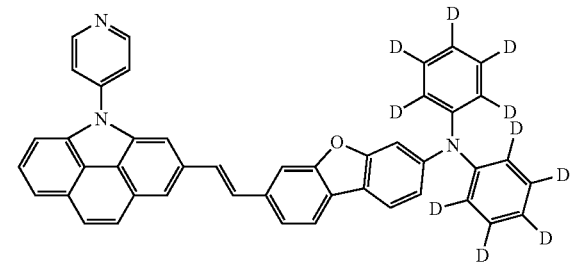
33
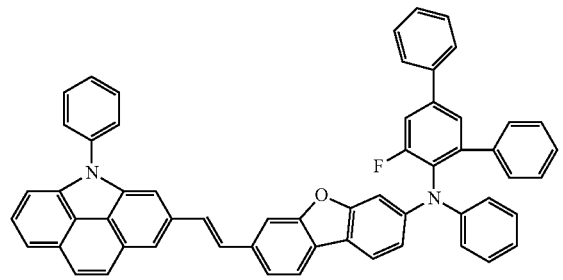
34
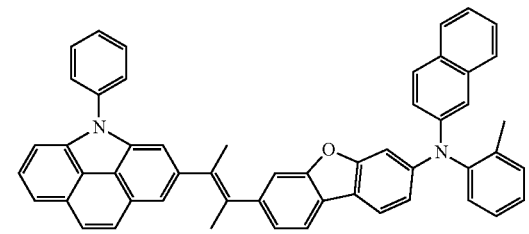
35
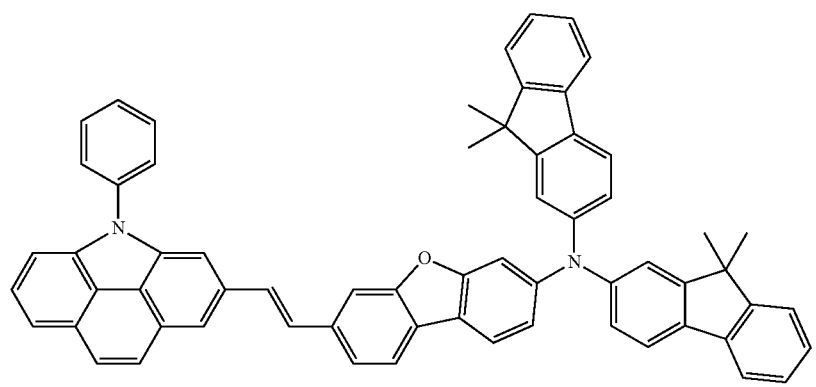

-continued
36
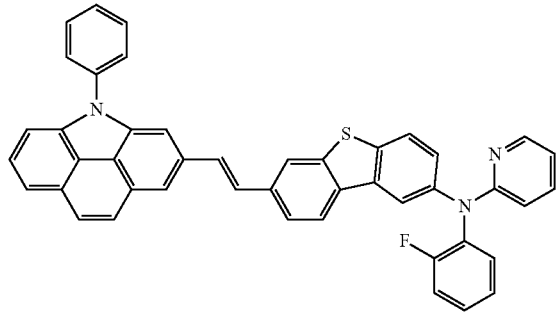
37
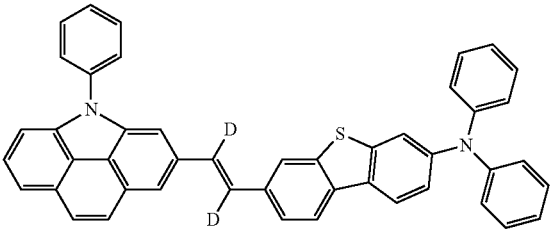
38
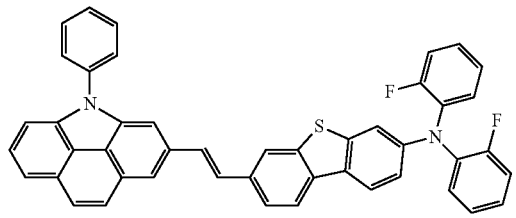
39
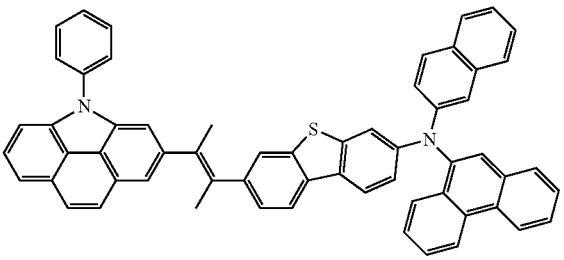
40
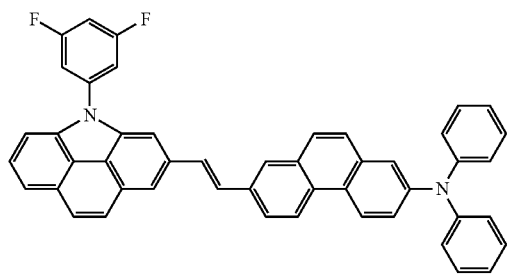
41
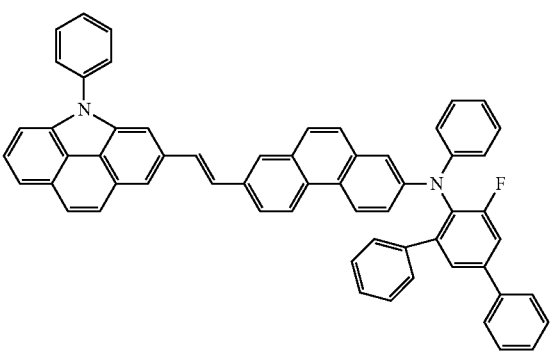
42
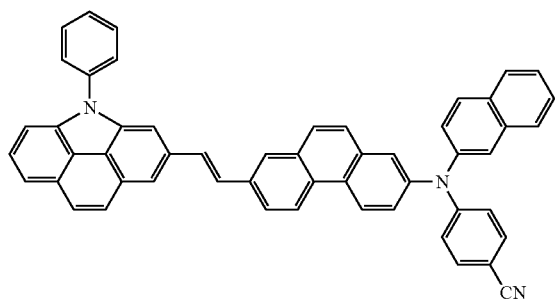
43
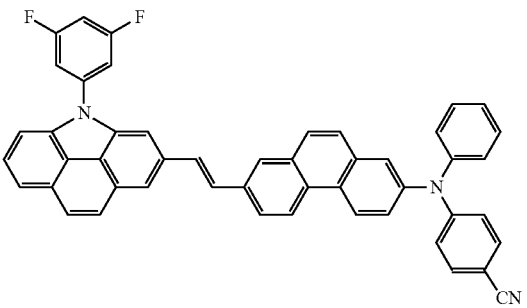
44
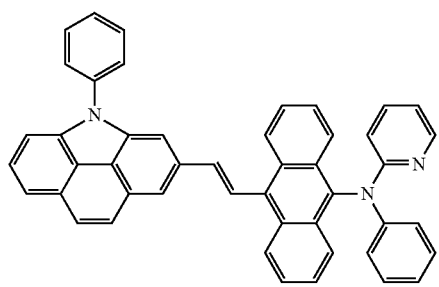
45
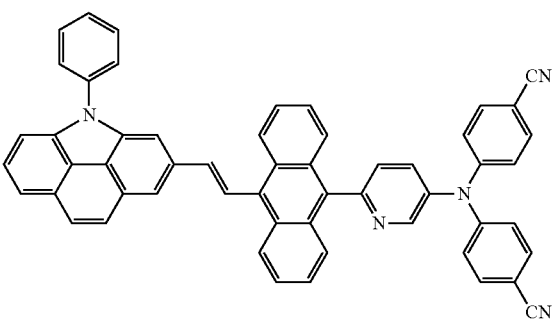

46
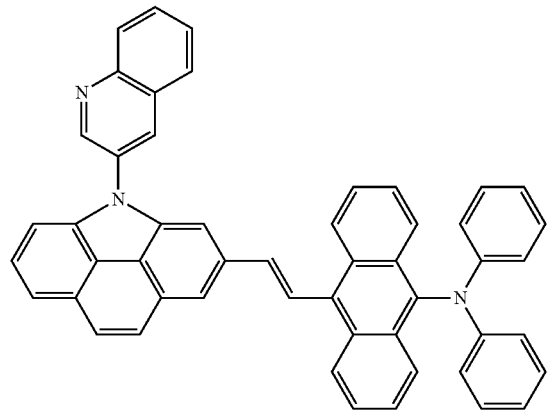
47
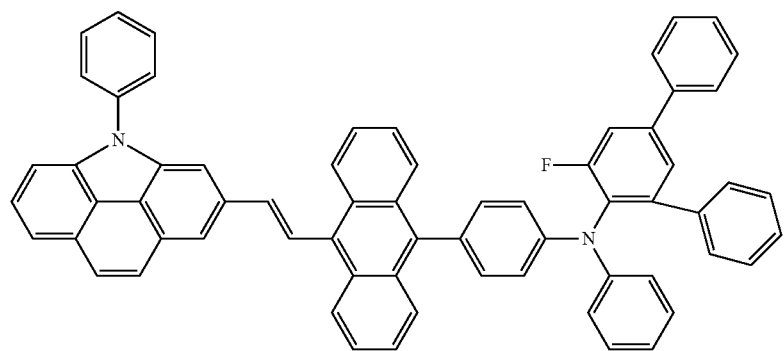
48
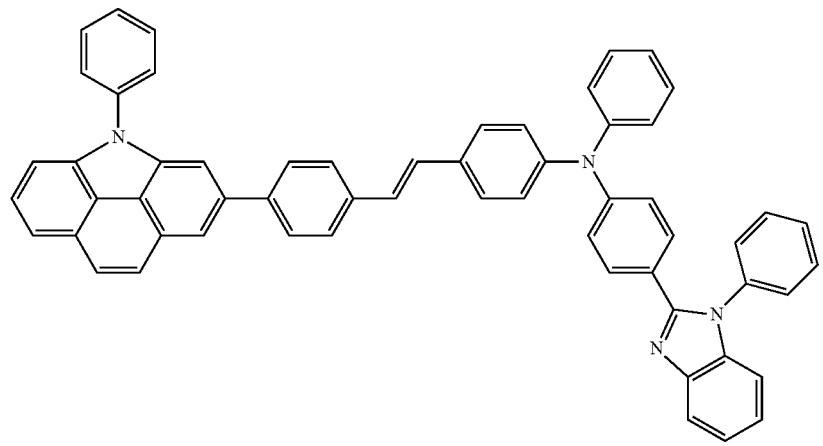
49
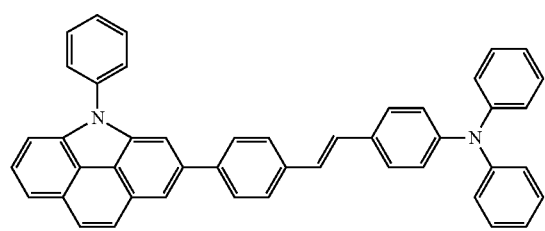
50
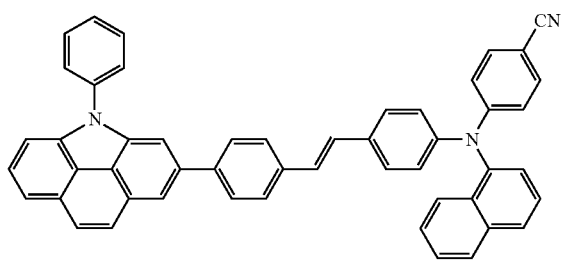

51
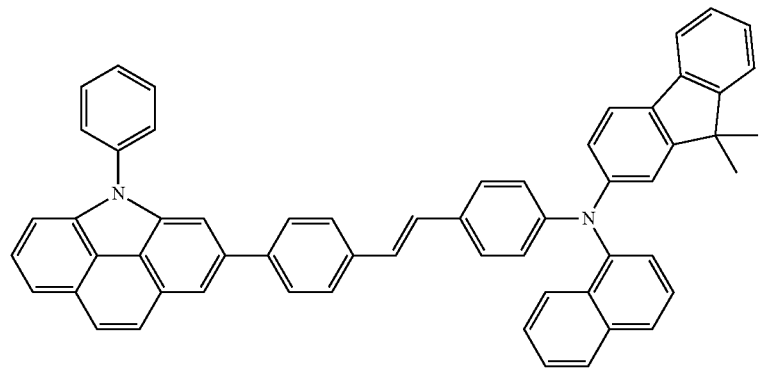
52
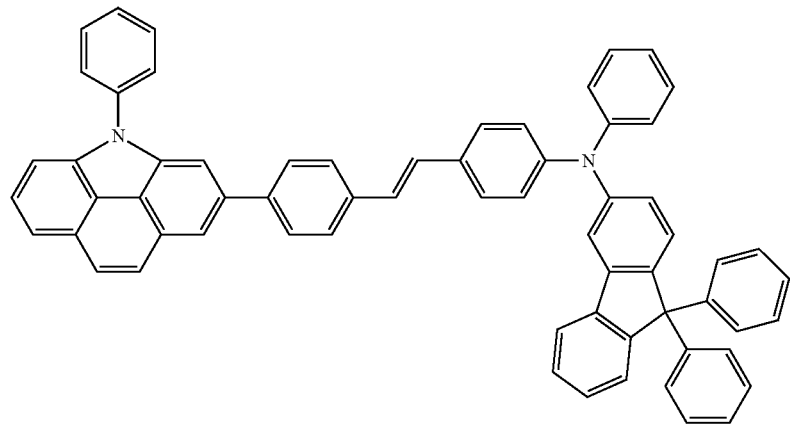
53
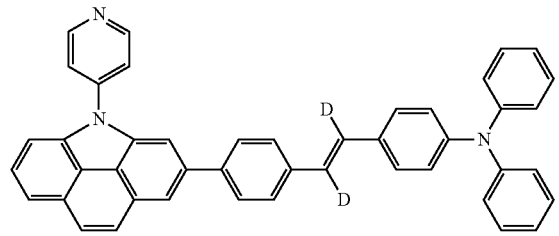
54
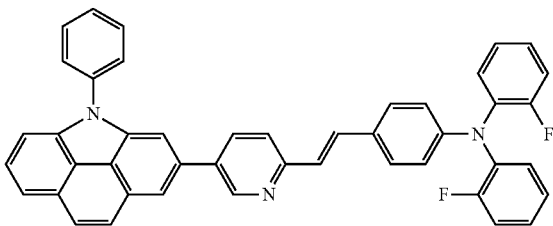
55
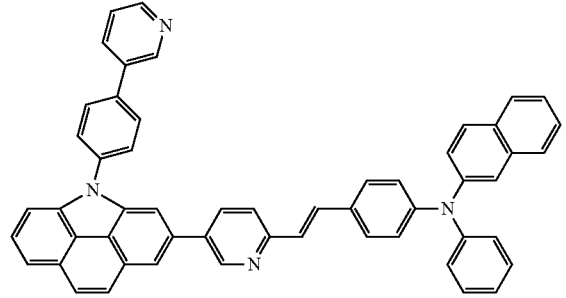
56
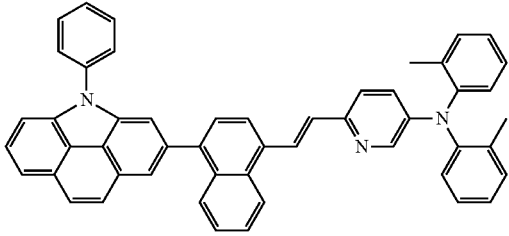

-continued
57
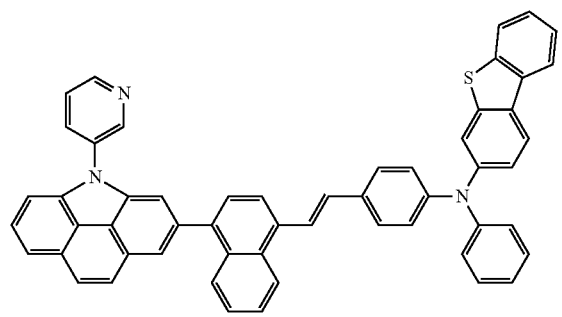
58
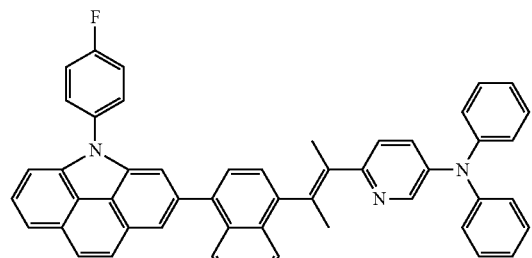
59
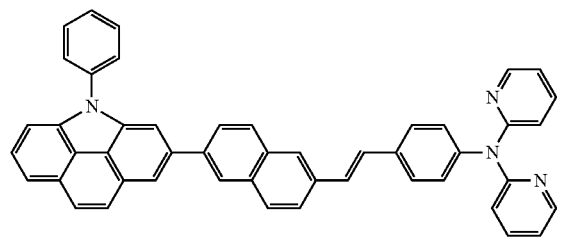
60
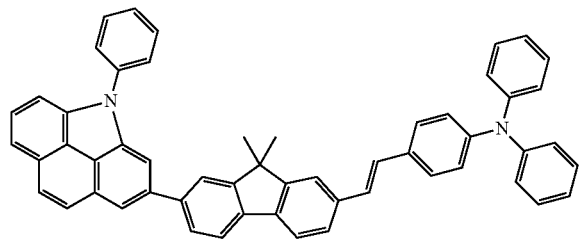
61
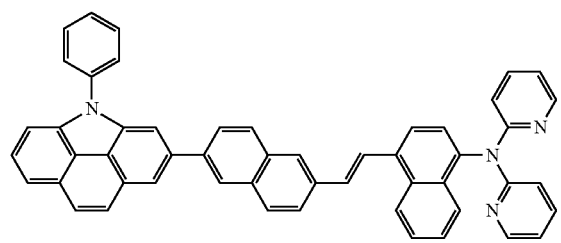
62
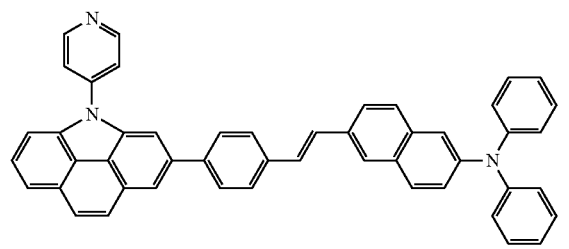
63
64
65
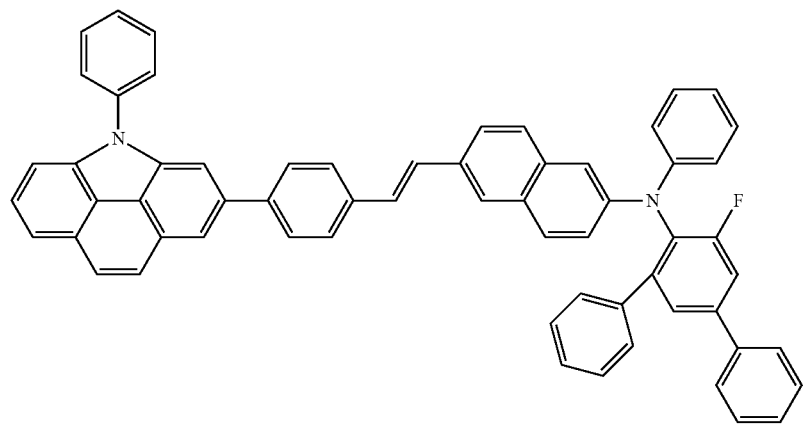

66
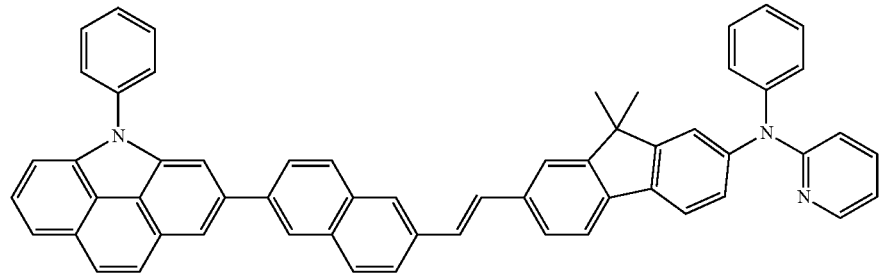
67
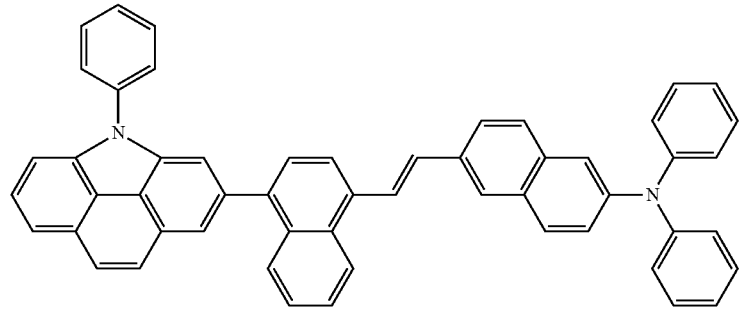
68
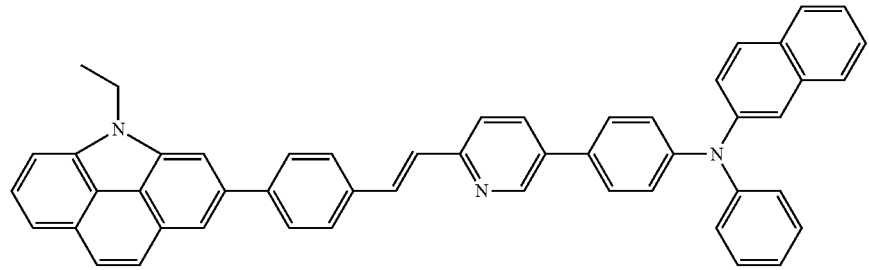
69
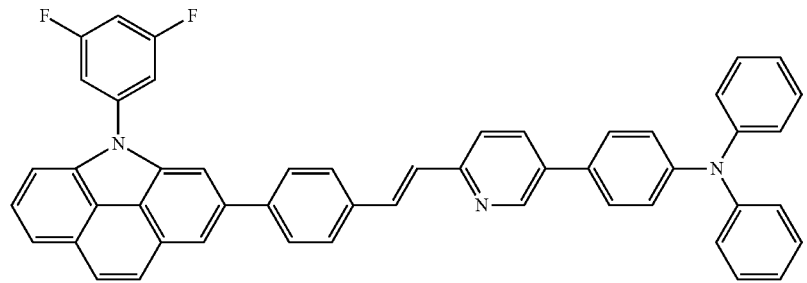
70
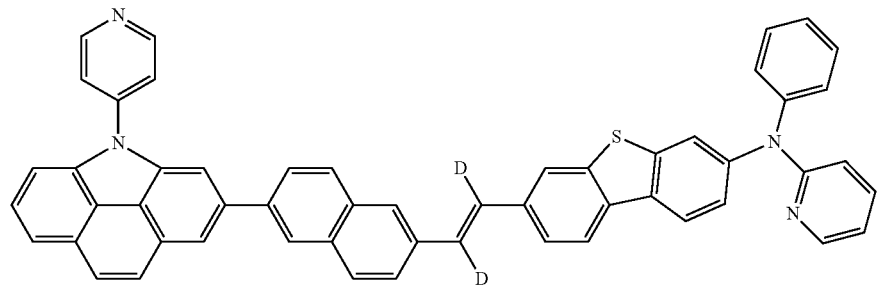

-continued
71
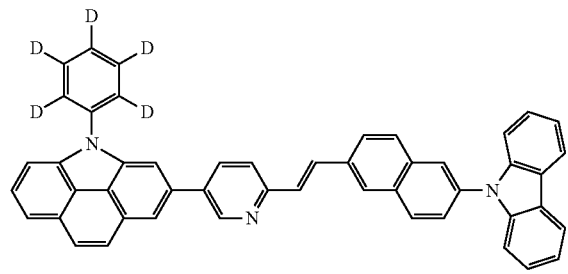
72
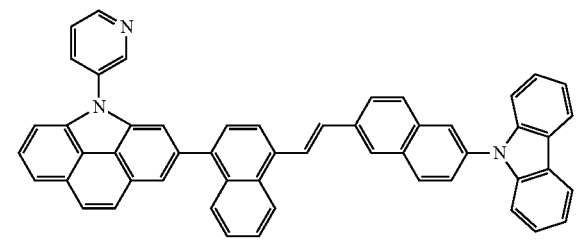
73
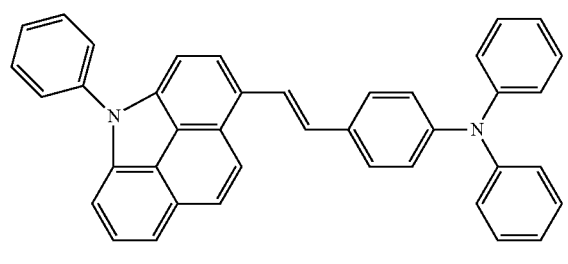
74
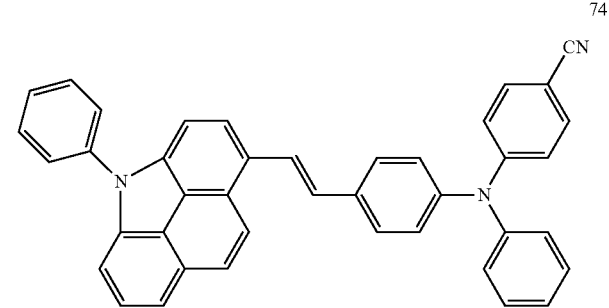
75
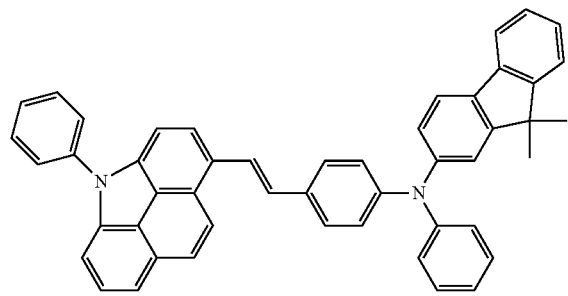
76
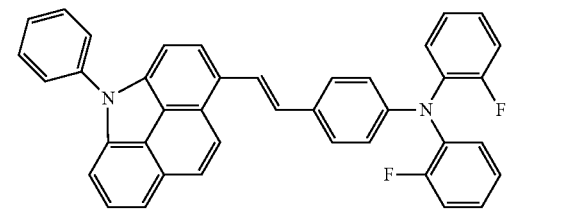
77
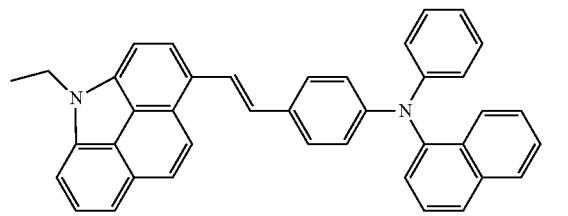
78
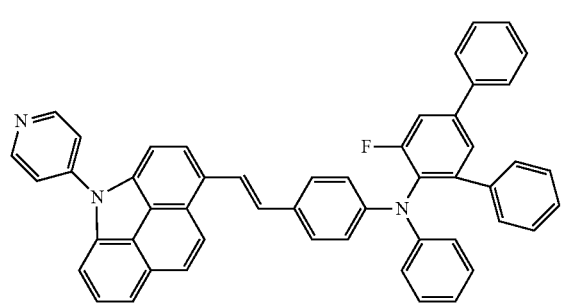
79
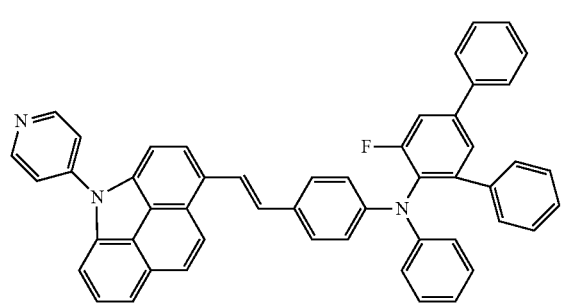
80
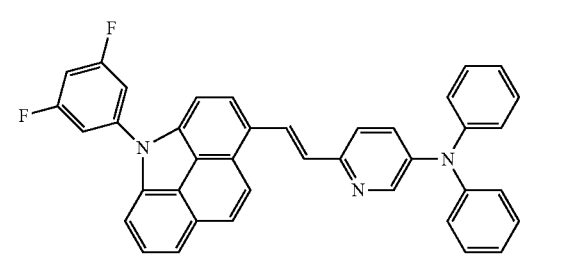

-continued
81
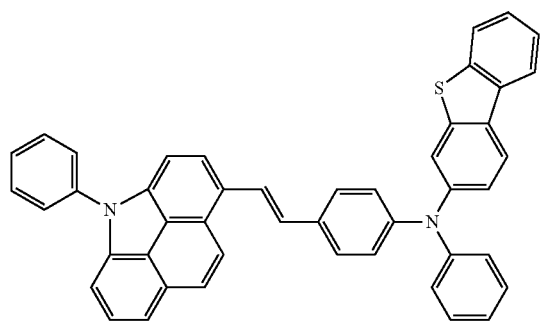
82
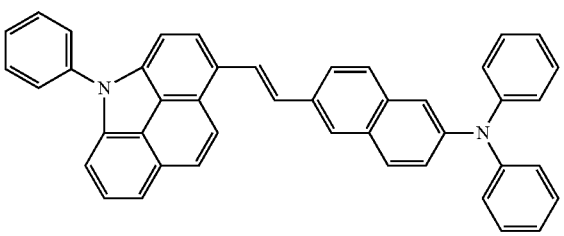
83
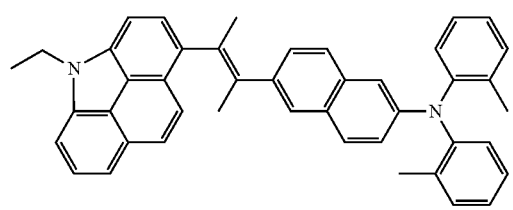
84
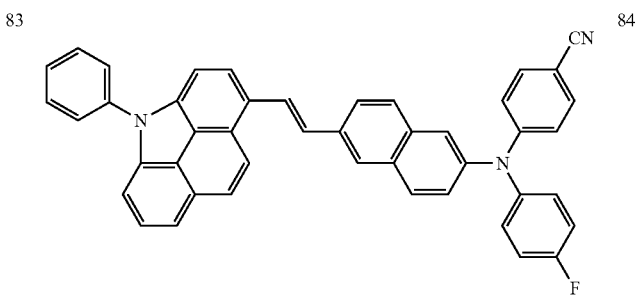
85
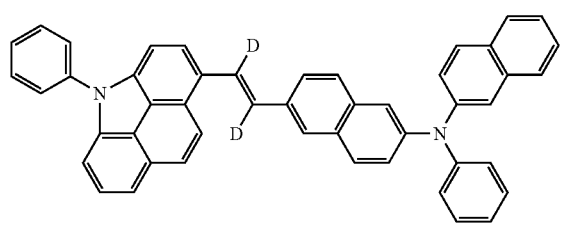
86
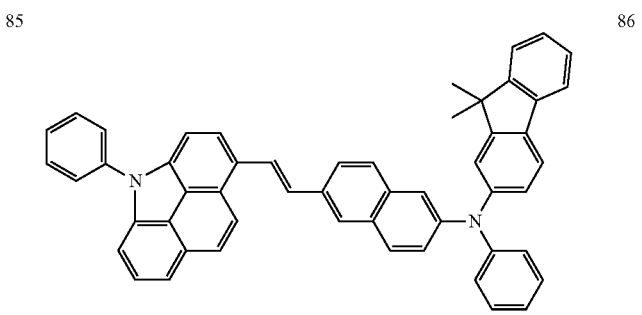
87
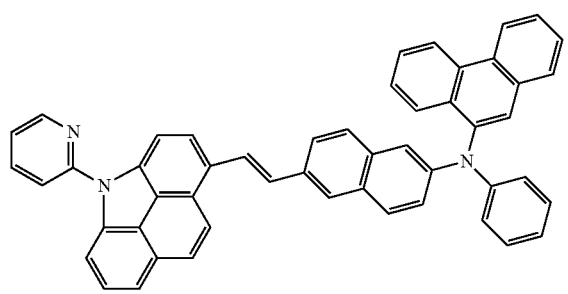
88
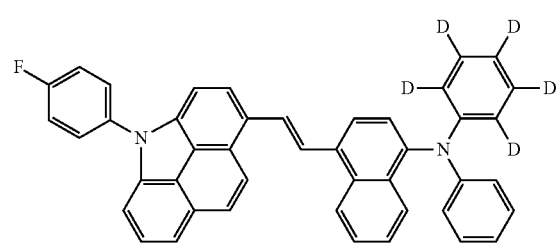
89
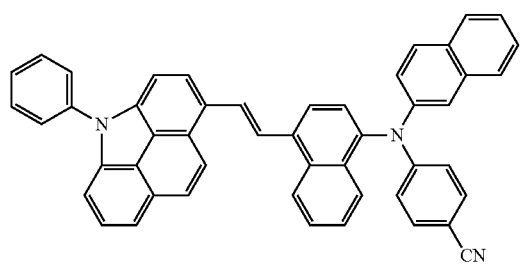
90
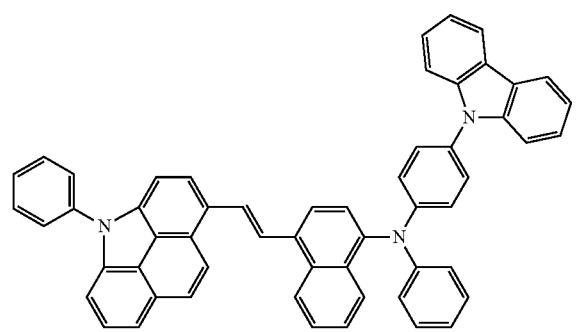

-continued
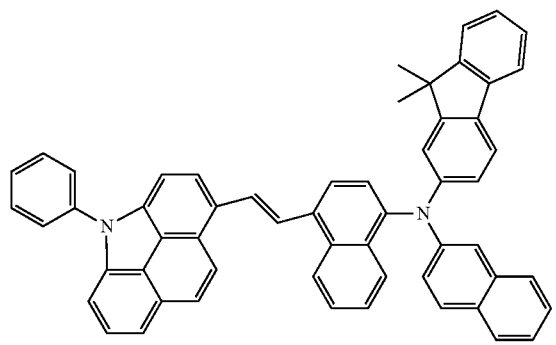
91
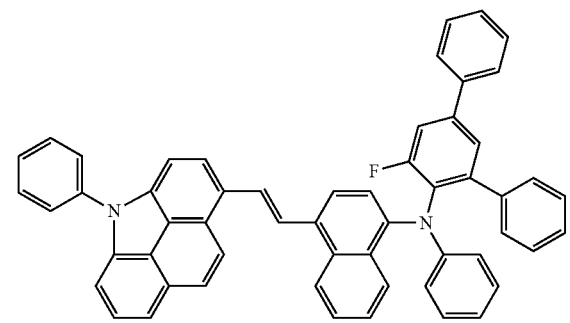
92
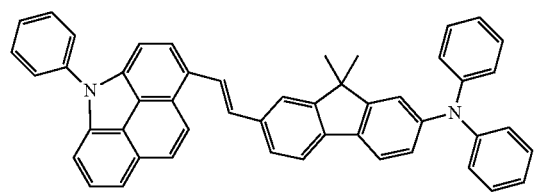
93
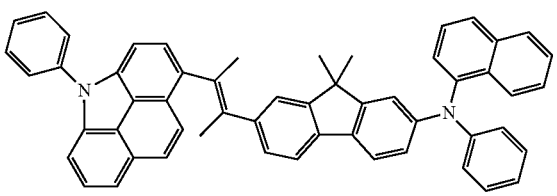
94
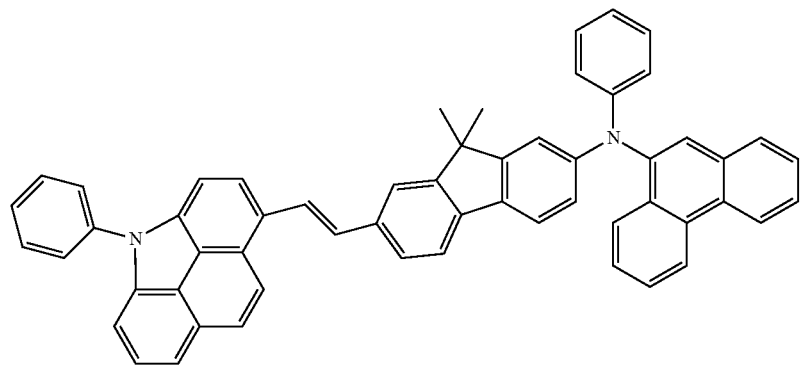
95
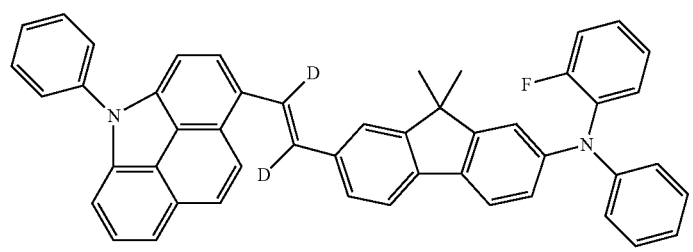
96
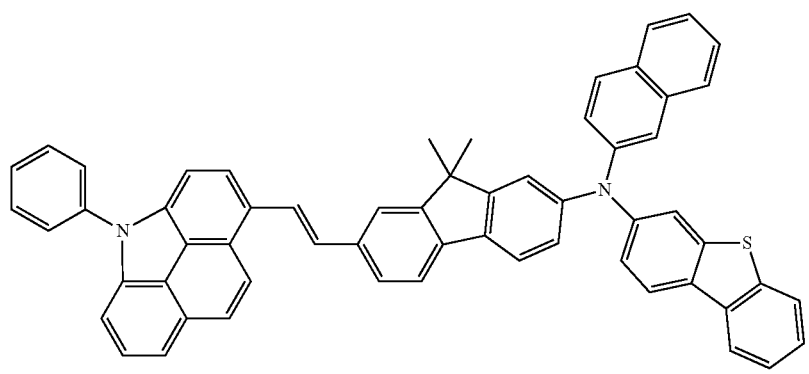
97

98
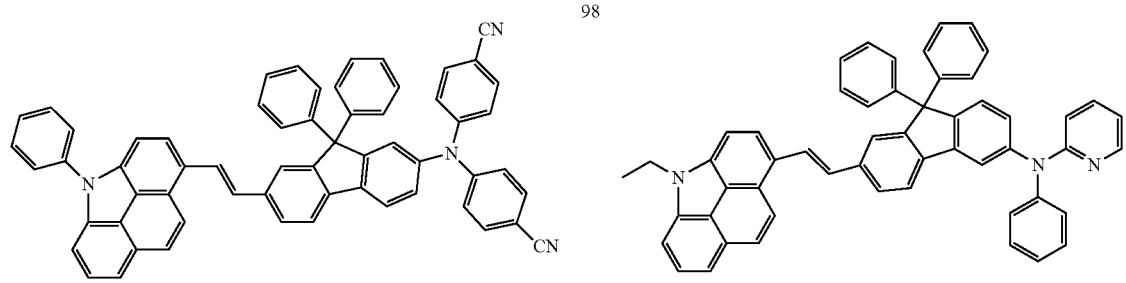
99
100
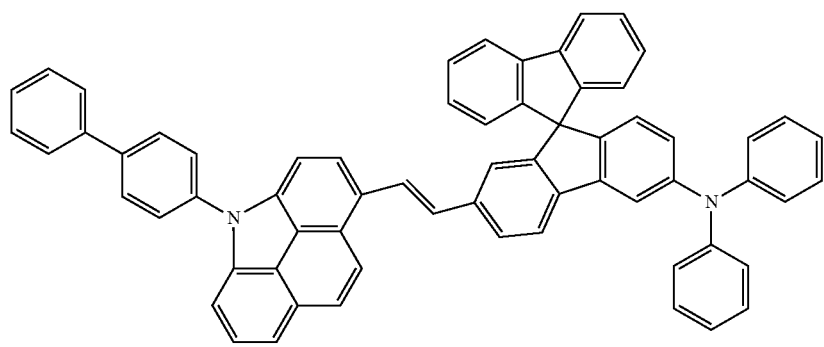
101
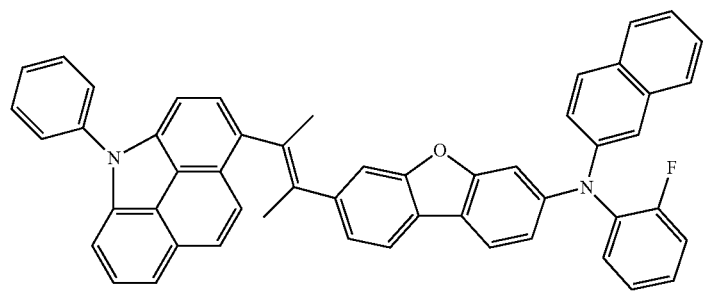
102
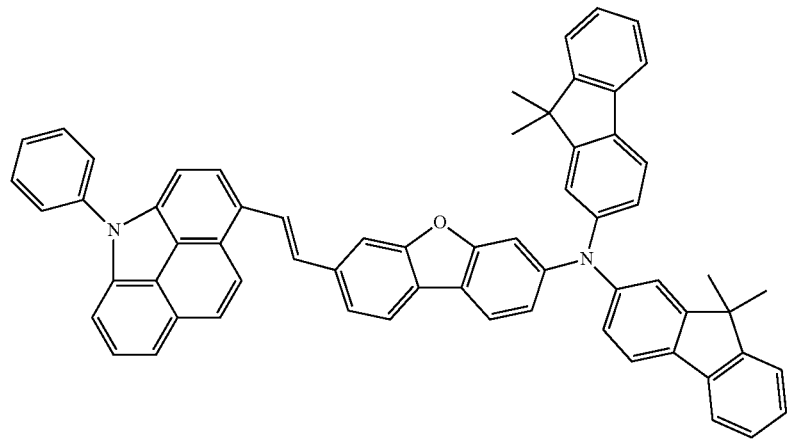

-continued
103
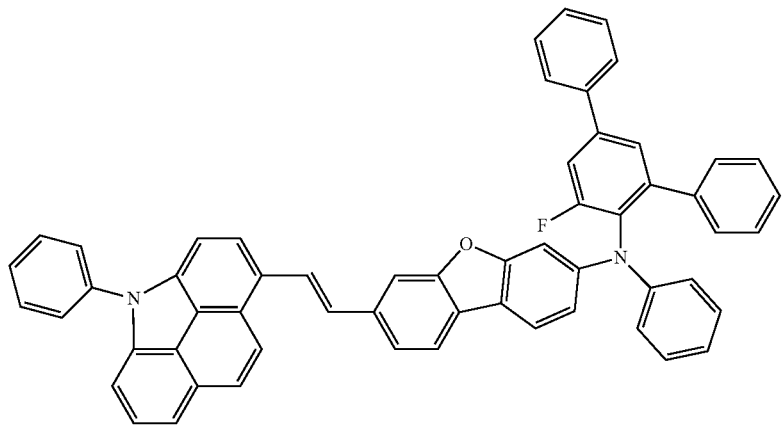
104
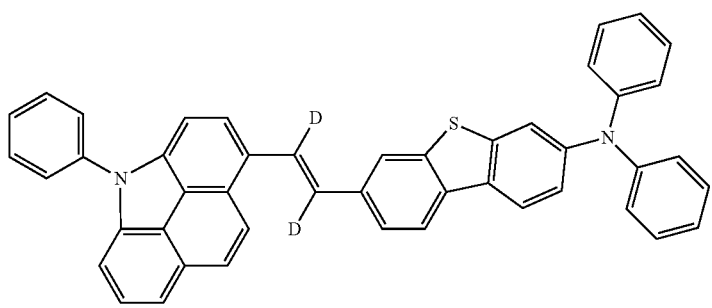
105
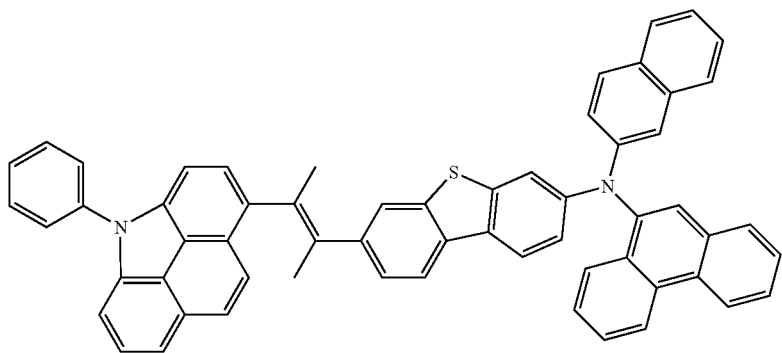
106
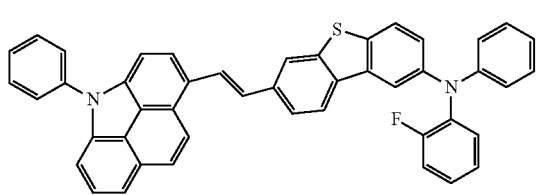
107
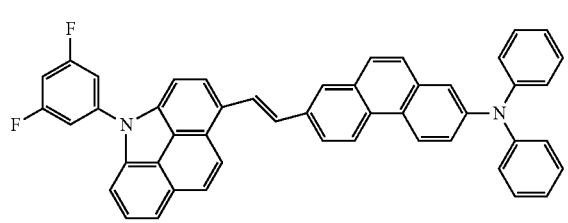

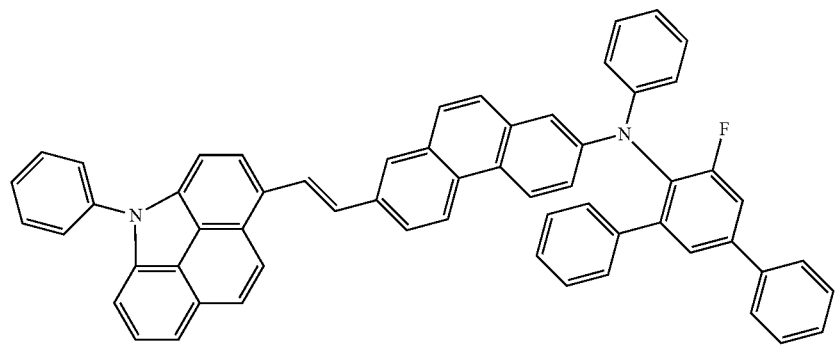
108
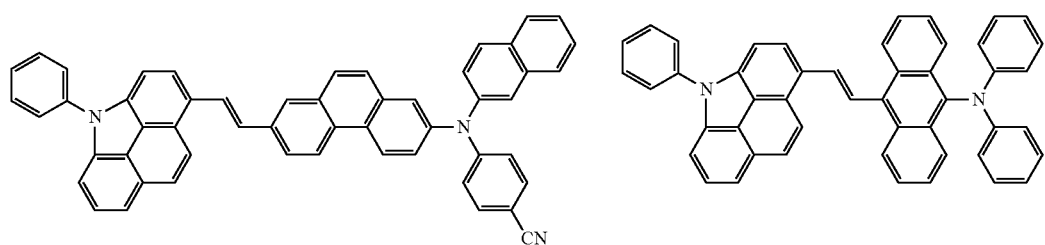
109  110
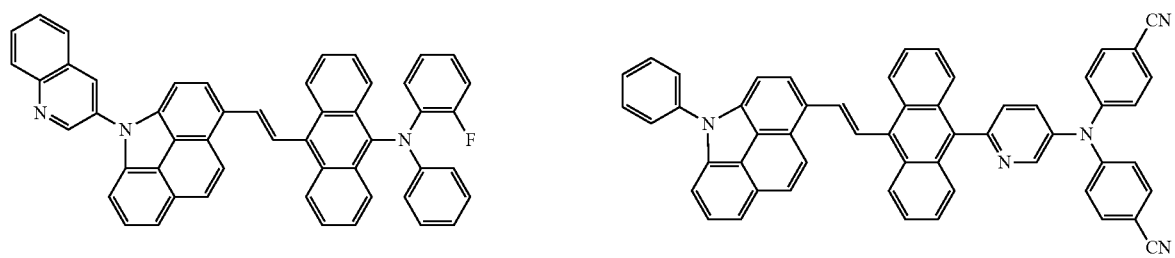
111  112
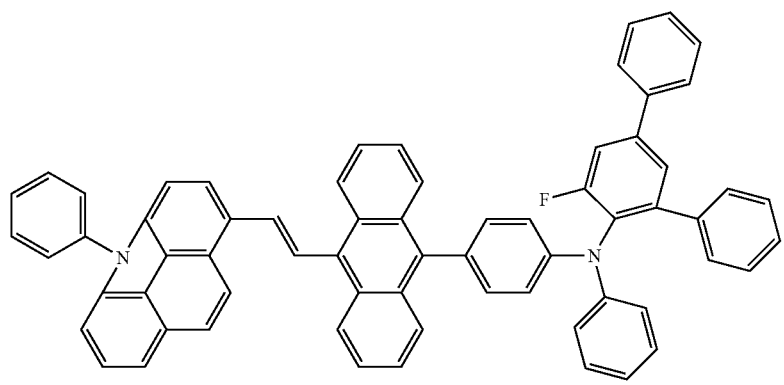
113

-continued
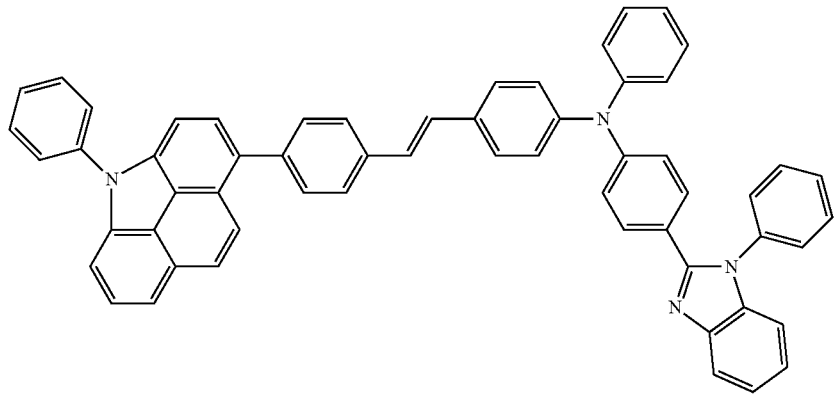
114
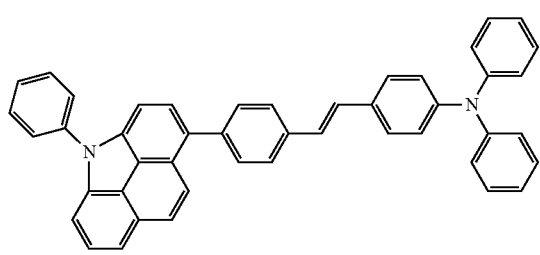
115
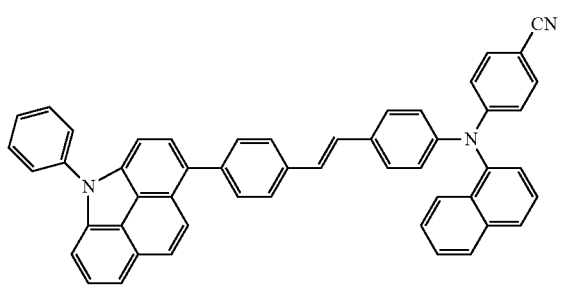
116
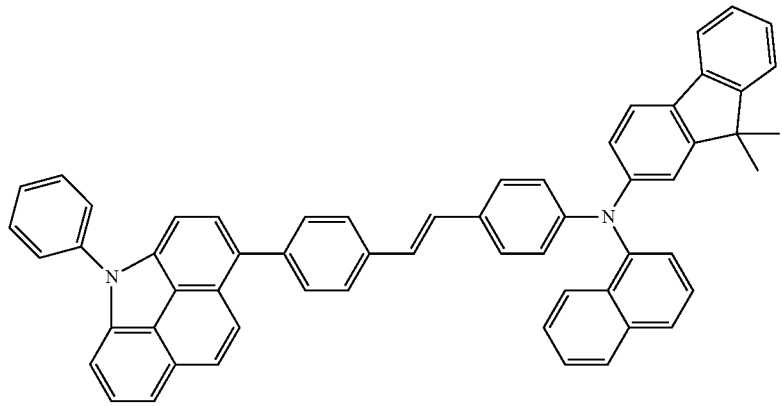
117
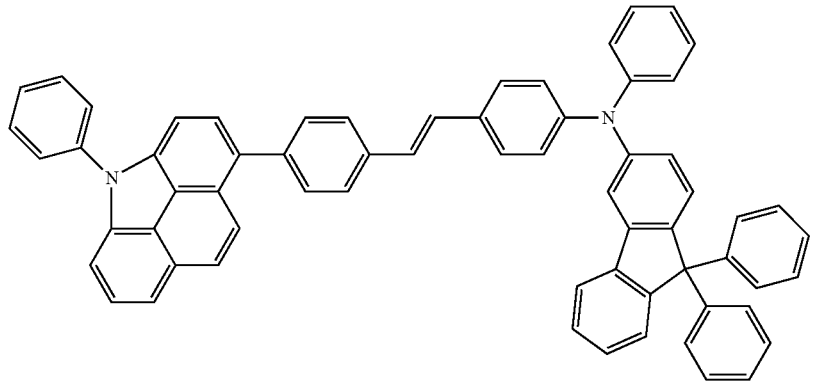
118

119
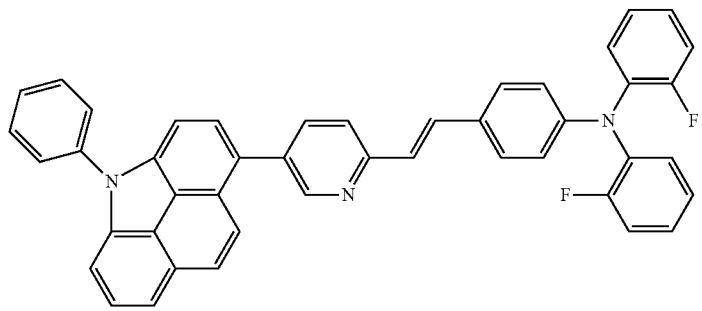
120
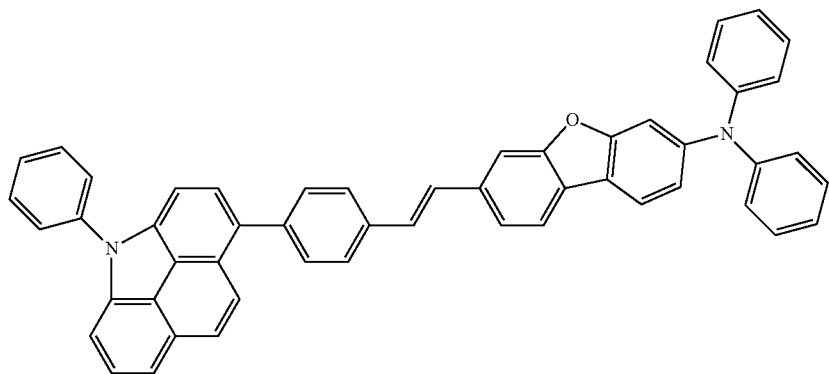
121
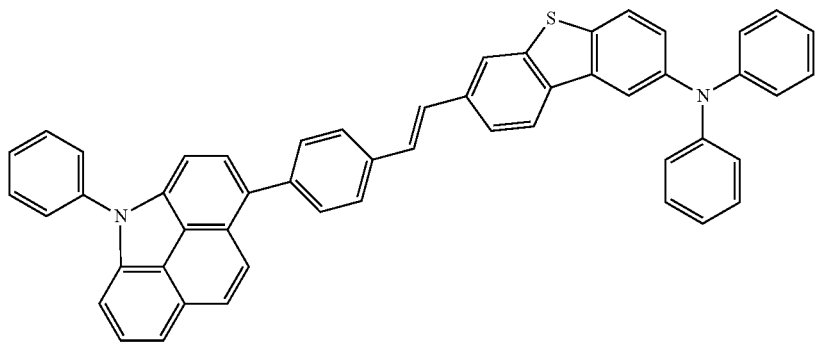
122
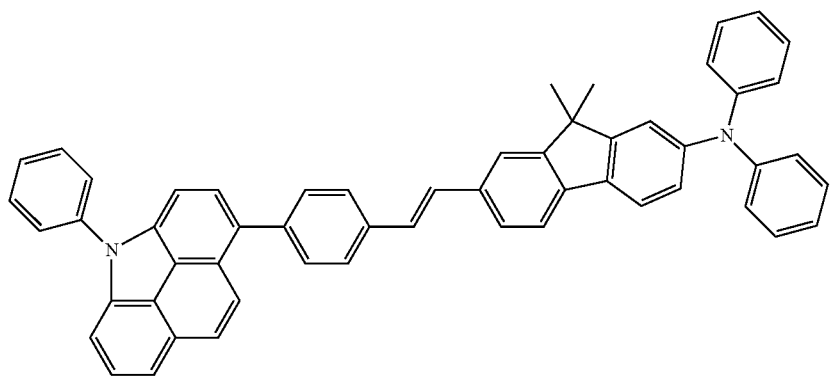

123
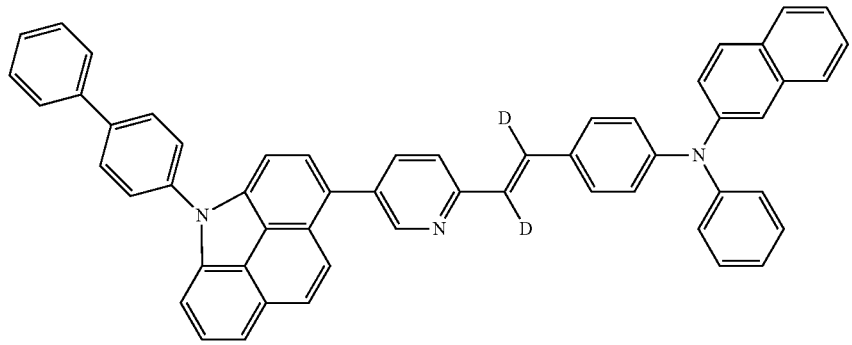
124
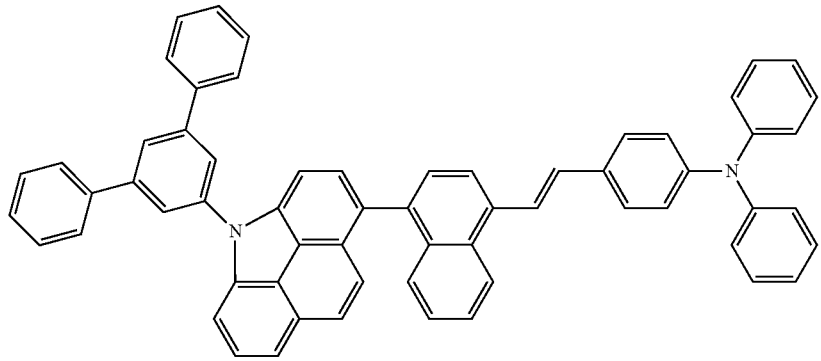
125 126
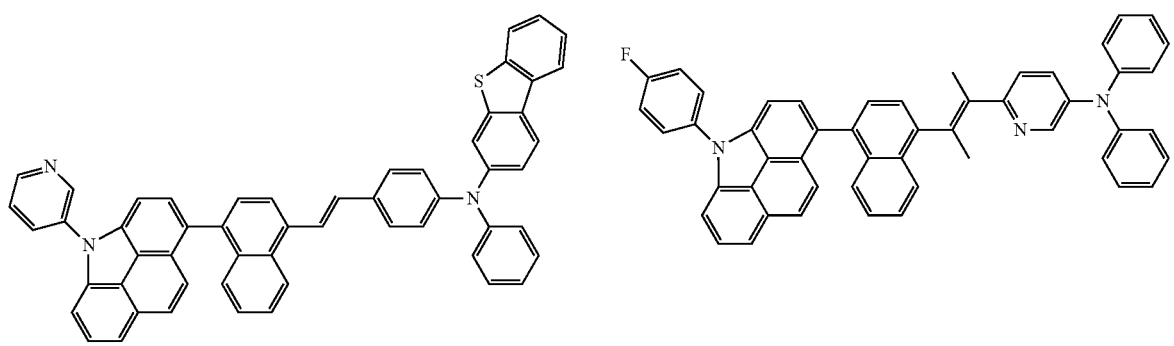
127
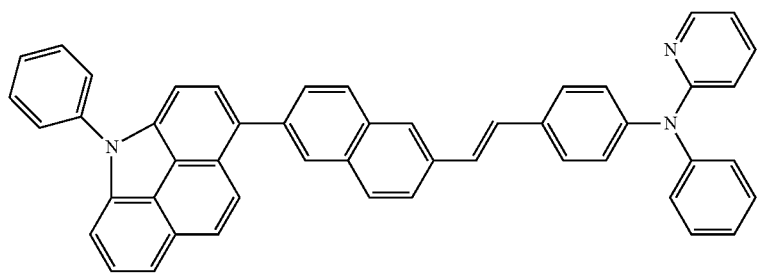
128
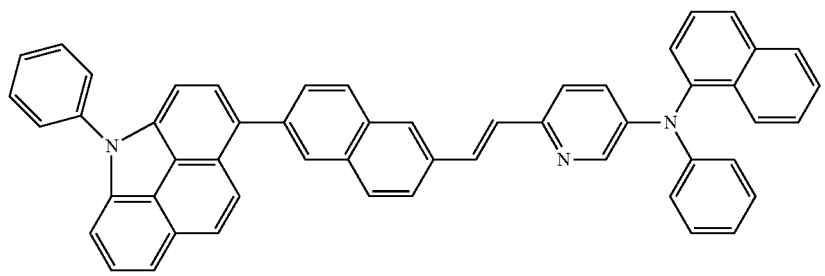

-continued
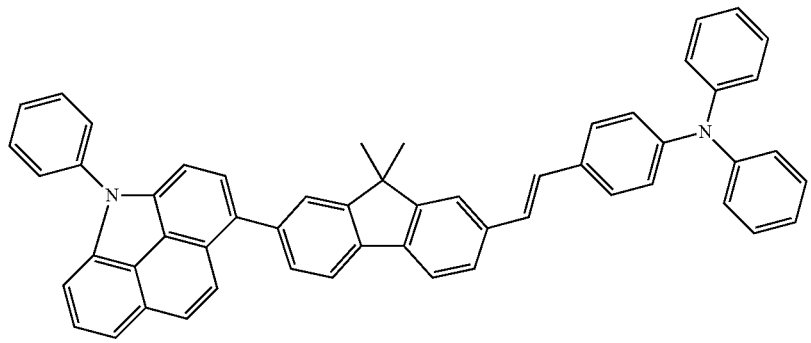
129
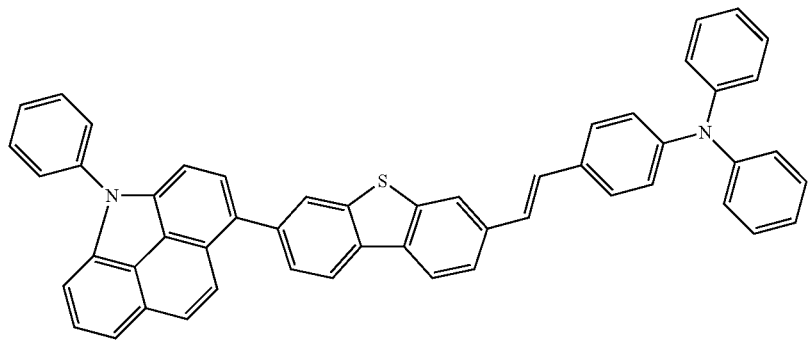
130
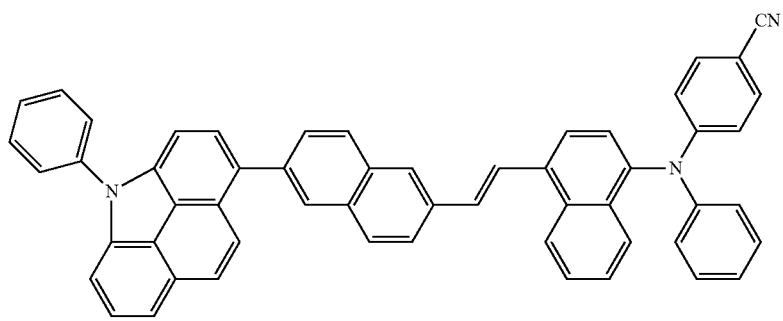
131
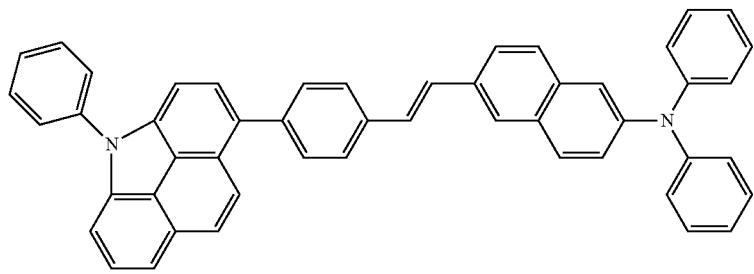
132
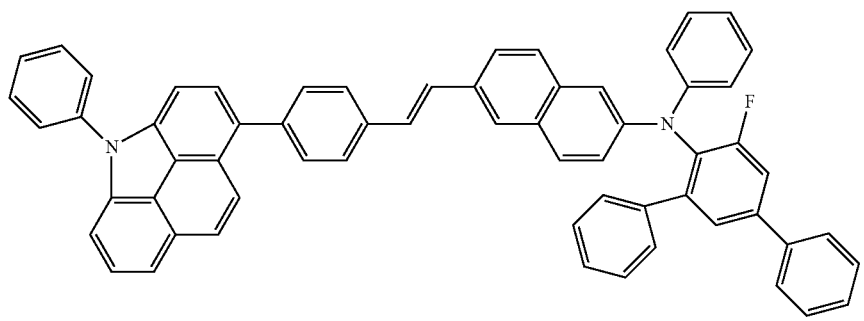
133

-continued
134
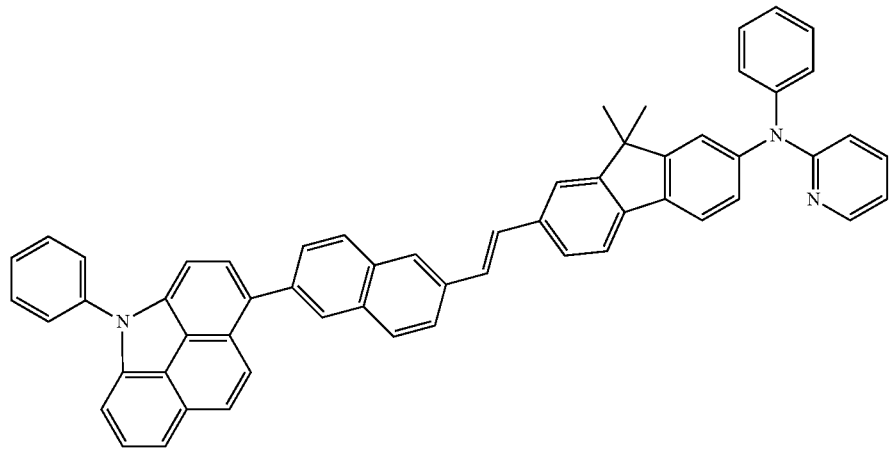
135
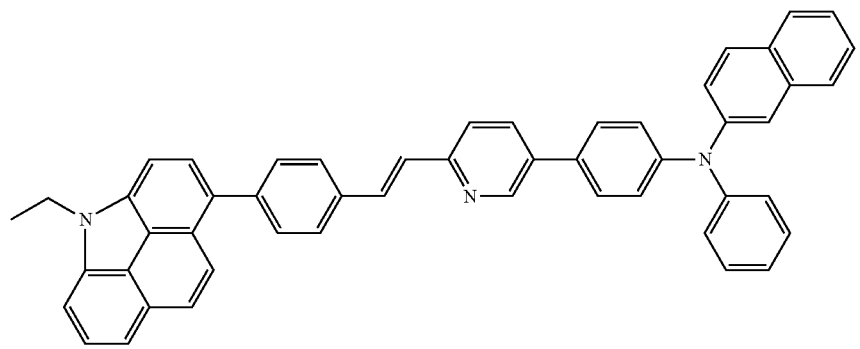
136
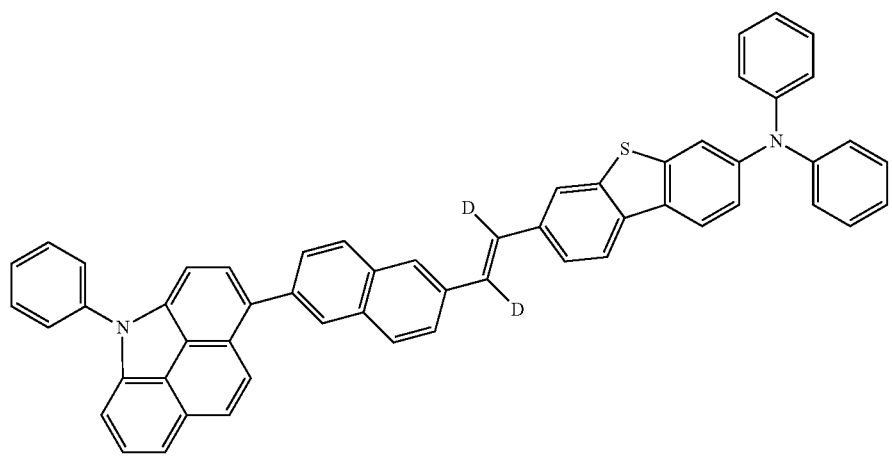
137
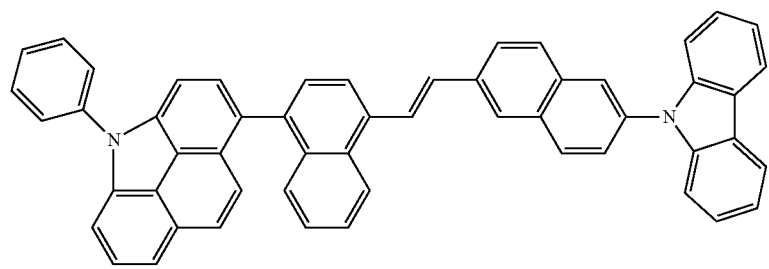

According to another aspect of the present invention, an OLED includes a first electrode, a second electrode, and an organic layer between the first electrode and the second electrode. The organic layer includes the compound of Formula 1 above.

The organic layer may include at least one layer selected from a hole injection layer (HIL), a hole transport layer (HTL), a functional layer having both hole injection and hole transport capabilities (hereinafter, referred as a "H-functional layer"), a buffer layer, an electron blocking layer (EBL), an emission layer (EML), a hole blocking layer (HBL), an electron transport layer (ETL), an electron injection layer (EIL), or a functional layer having both electron injection and electron transport capabilities (hereinafter, referred to as an "E-functional layer").

The organic layer may be used as an EML, for example a blue EML.

In some embodiments, the OLED may include an EIL, an ETL, an EML, a HIL, a HTL, or a H-functional layer having both hole injection and hole transport capabilities, and the EML may include the compound of Formula 1 above, and an anthracene-based compound, an arylamine-based compound, or a styryl-based compound.

In some other embodiments, the OLED may include an EIL, an ETL, an EML, a HIL, a HTL, or a H-functional layer having both hole injection and hole transport capabilities, and at least one of a red EML, a green EML, a blue EML, or a white EML of the EML may include a phosphorescent compound. The EML may include a compound according to an embodiment of the present invention, and may further include a charge-generating material in addition to the above-mentioned compound. The charge-generating material may be a p-dopant, and the p-dopant may be a quinone derivative, a metal oxide, or a cyano group-containing compound.

In some other embodiments, the organic layer may include an ETL, and the ETL may include an electron-transporting organic compound and a metal complex. The metal complex may be a lithium (Li) complex.

The term "organic layer," as used herein, refers to a single layer and/or a multi-layered structure disposed between the first electrode and the second electrode of the OLED.

FIG. 1 is a schematic view of a structure of an OLED according to an embodiment of the present invention. Hereinafter, a structure and manufacturing method of an OLED according to an embodiment of the present invention will be described with reference to FIG. 1.

The substrate (not illustrated) may be any substrate generally used in OLEDs, e.g., a glass substrate or transparent plastic substrate having mechanical strength, thermal stability, transparency, surface smoothness, ease of handling, and water resistance.

The first electrode may be formed by depositing or sputtering a first electrode material on the substrate. When the first electrode is an anode, the first electrode material may be selected from materials with a high work function to enable ease of hole injection. The first electrode may be a reflective electrode or a transmission electrode. The first electrode material may be a transparent material with high conductivity, and examples thereof include indium tin oxide (ITO), indium zinc oxide (IZO), tin oxide ($SnO_2$), and zinc oxide (ZnO). When magnesium (Mg), aluminum (Al), aluminum-lithium (Al—Li), calcium (Ca), magnesium-indium (Mg—In), magnesium-silver (Mg—Ag), or the like is used, the first electrode may be a reflective electrode.

The first electrode may have a single-layer structure or a multi-layered structure including at least two layers. For example, the first electrode may have a three-layered structure of ITO/Ag/ITO, but is not limited thereto.

The organic layer may be disposed on the first electrode.

The organic layer may include a HIL, a HTL, a buffer layer (not illustrated), an EML, an ETL, and/or an EIL.

The HIL may be formed on the first electrode by various methods such as vacuum deposition, spin coating, casting, and Langmuir-Blodgett (LB) deposition. When the HIL is formed using vacuum deposition, the vacuum deposition conditions may vary depending on the compound used to form the HIL, and the desired structural and thermal properties of the HIL to be formed. For example, the vacuum deposition may be performed at a temperature of about 100° C. to about 500° C., a pressure of about $10^{-8}$ torr to about $10^{-3}$ torr, and a deposition rate of about 0.01 Å/sec to about 100 Å/sec. However, the deposition conditions are not limited thereto.

When the HIL is formed using spin coating, the coating conditions may vary depending on the compound used to form the HIL, and the desired structural and thermal properties of the HIL to be formed. For example, the coating rate may be about 2,000 rpm to about 5,000 rpm, and the temperature at which heat treatment is performed to remove solvent after coating may be about 80° C. to about 200° C. However, the coating conditions are not limited thereto.

As a material for the HIL, any hole-injecting material may be used, for example, N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), or polyaniline/poly(4-styrenesulfonate) (PANI/PSS). However, the hole-injecting material is not limited thereto.

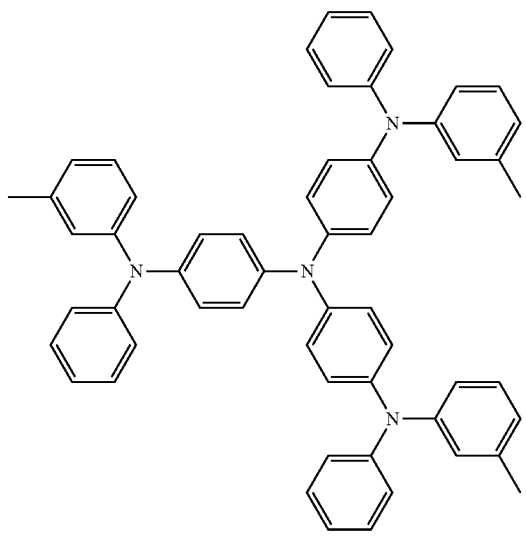

m-MTDATA

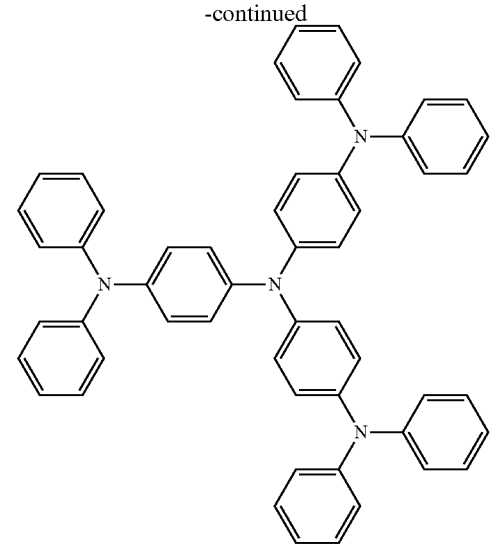

TDATA

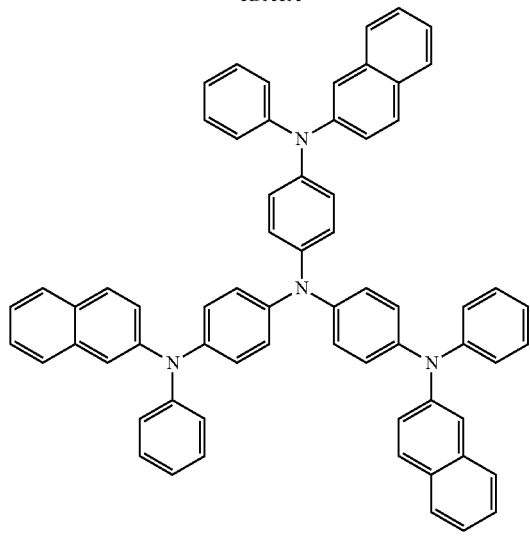

2-TNATA

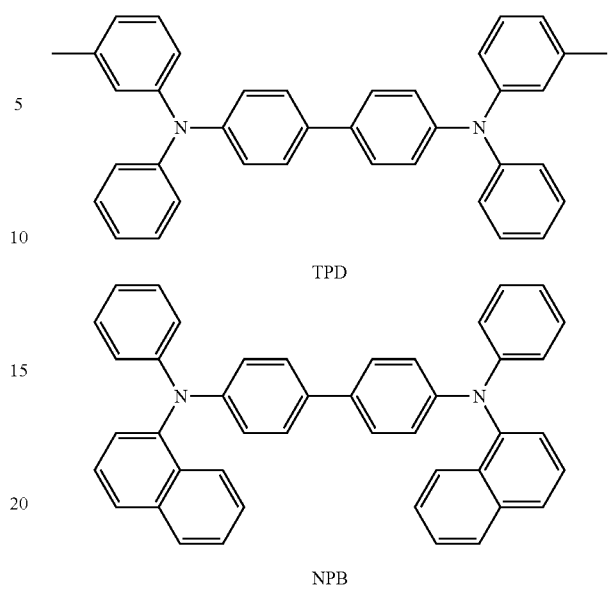

TPD

NPB

A thickness of the HIL may be about 100 Å to about 10,000 Å, for example, about 100 Å to about 1000 Å. When the thickness of the HIL is within the above ranges, the HIL may have satisfactory hole injection characteristics without a substantial increase in driving voltage.

Then, the HTL may be formed on the HIL by vacuum deposition, spin coating, casting, LB deposition, or the like. When the HTL is formed using vacuum deposition or spin coating, the deposition or coating conditions may be similar to those described above for formation of the HIL. However, the deposition and coating conditions may vary depending on the compound used to form the HTL.

As a material for the HTL, any hole-transporting material may be used, for example, a carbazole derivative such as N-phenylcarbazole or polyvinylcarbazole, N,N'-bis(3-methylphenyl)-N,N'-diphenyl-[1,1-biphenyl]-4,4'-diamine (TPD), 4,4',4''-tris(N-carbazolyl)triphenylamine (TCTA), and N,N'-di(1-naphthyl)-N,N'-diphenylbenzidine (NPB). However, the hole-transporting material is not limited thereto.

A thickness of the HTL may be about 50 Å to about 2,000 Å, for example, about 100 Å to about 1,500 Å. When the thickness of the HTL is within the above ranges, the HTL may have satisfactory hole transport characteristics without a substantial increase in driving voltage.

The H-functional layer (i.e., the functional layer having both hole injection and hole transport capabilities) may include one or more materials selected from the above-described materials for the HIL and the HTL. A thickness of the H-functional layer may be about 500 Å to about 10,000 Å, for example, about 100 Å to about 1,000 Å. When the thickness of the H-functional layer is within the above ranges, the H-functional layer may have satisfactory hole injection and transport characteristics without a substantial increase in driving voltage.

In some embodiments, at least one of the HIL, the HTL, and the H-functional layer may include at least one of the following compounds represented by Formulas 300 and 350.

<Formula 300>

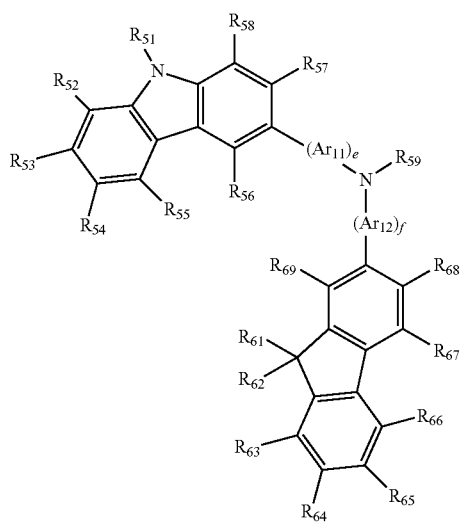

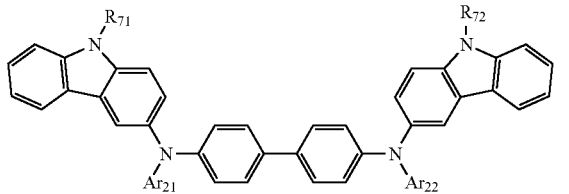

<Formula 350>

$Ar_{11}$, $Ar_{12}$, $Ar_{21}$, and $Ar_{22}$ in Formulas 300 and 350 may each independently be a substituted or unsubstituted $C_5$-$C_{60}$ arylene group.

e and f in Formula 300 may each independently be an integer from 0 to 5, for example, 0, 1, or 2. In some embodiments, e may be 1 and f may be 0, but the present invention is not limited thereto.

$R_{51}$ to $R_{58}$, $R_{61}$ to $R_{69}$ and $R_{71}$, and $R_{72}$ in Formulas 300 and 350 may each independently be a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. For example, $R_{51}$ to $R_{58}$, $R_{61}$ to $R_{69}$ and $R_{71}$, and $R_{72}$ may each independently be:

i) a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group (e.g., a methyl group, an ethyl group, a propyl group, a butyl group, a pentyl group, a hexyl group, or the like), a $C_1$-$C_{10}$ alkoxy group (e.g., a methoxy group, an ethoxy group, a propoxy group, a butoxy group, a pentoxy group, or the like); or ii) a $C_1$-$C_{10}$ alkyl group or a $C_1$-$C_{10}$ alkoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, or a phosphoric acid group or a salt thereof; or iii) a phenyl group, a naphthyl group, an anthryl group, a fluorenyl group, or a pyrenyl group; or iv) a phenyl group, a naphthyl group, an anthryl group, a fluorenyl group, or a pyrenyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, or a $C_1$-$C_{10}$ alkoxy group.

However, $R_{51}$ to $R_{58}$, $R_{61}$ to $R_{69}$ and $R_{71}$, and $R_{72}$ are not limited to the above.

$R_{59}$ in Formula 300 may be a phenyl group, a naphthyl group, an anthryl group, a biphenyl group, or a pyridyl group; or a phenyl group, a naphthyl group, an anthryl group, a biphenyl group, or a pyridyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, or a substituted or unsubstituted $C_1$-$C_{20}$ alkoxy group.

In some embodiments, the compound of Formula 300 may be represented by 300A below, but the compound is not limited thereto.

<Formula 300A>

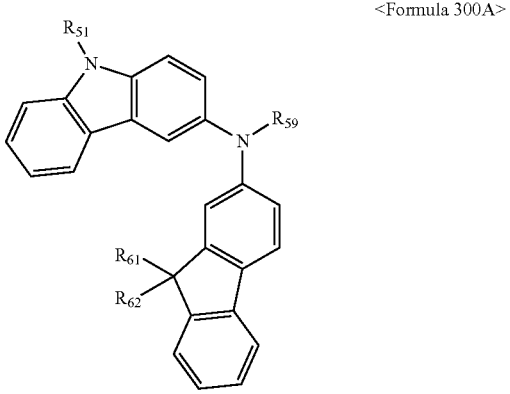

$R_{51}$, $R_{62}$, $R_{61}$, and $R_{59}$ in Formula 300A are as described above.

For example, at least one of the HIL, HTL, and the H-functional layer may include at least one of the following Compounds 301 to 320, but the HIL, HTL, and the H-functional layer are not limited thereto:

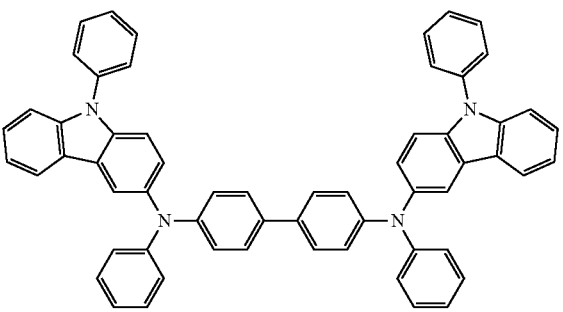

301

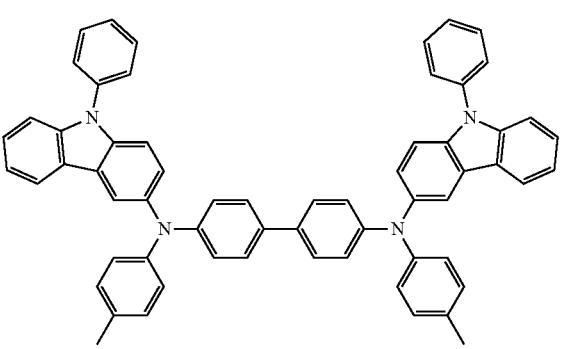

302

303
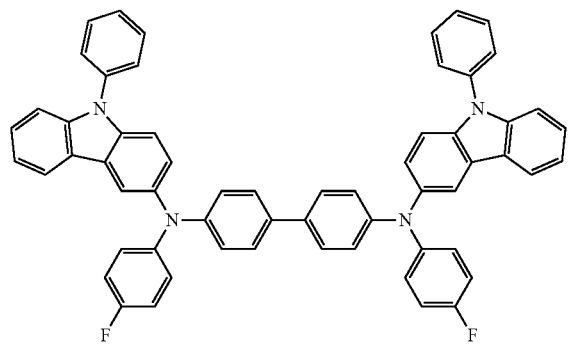
304
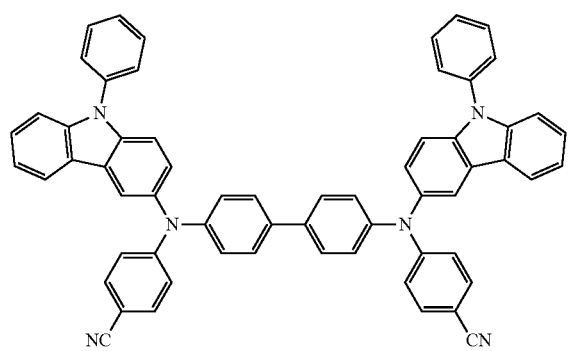
305
306
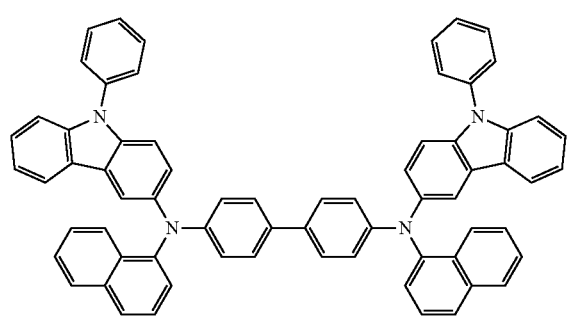
307
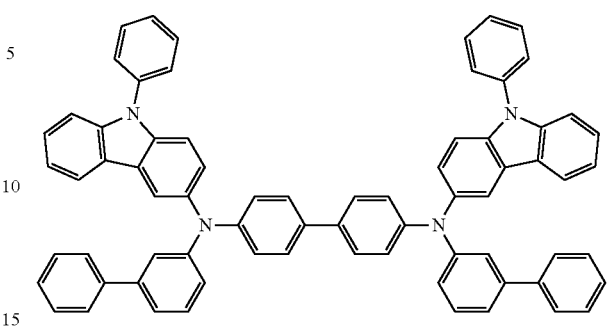
308
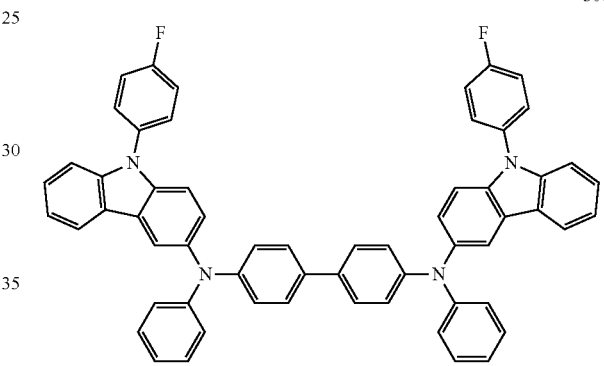
309
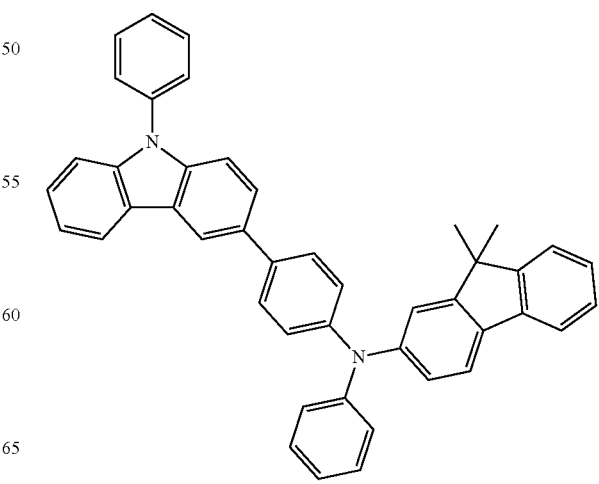

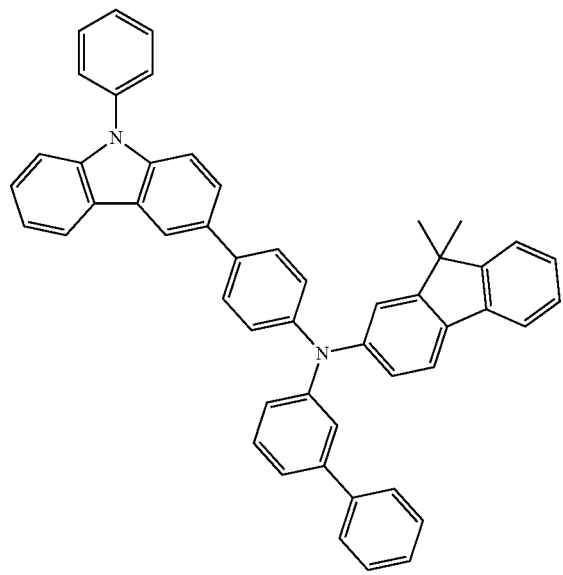
310
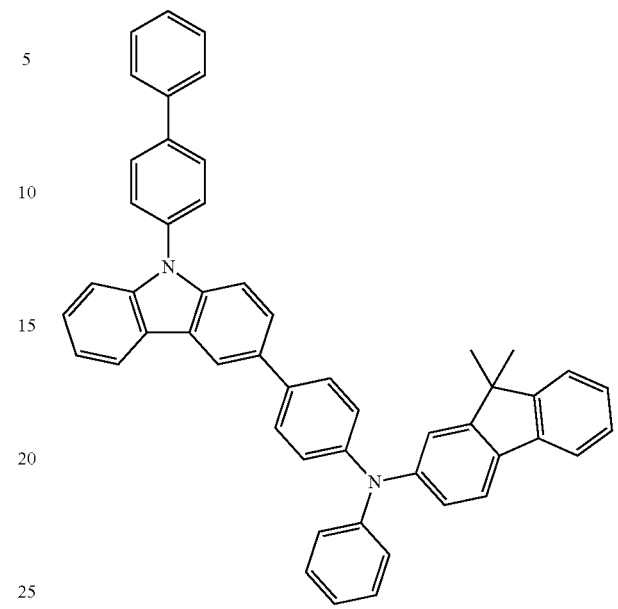
312
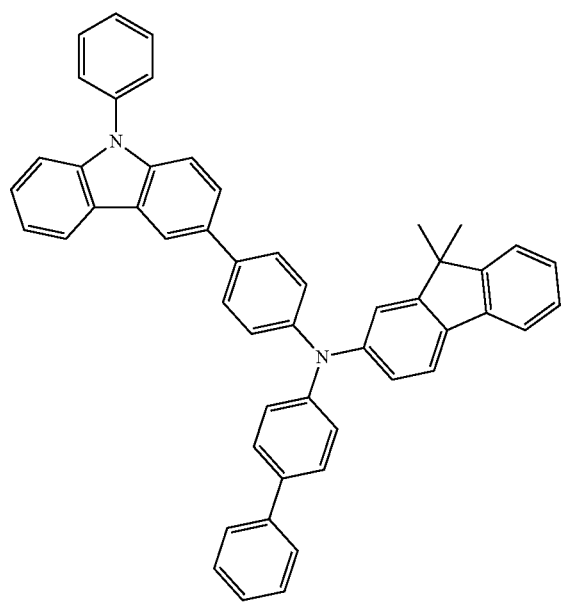
311
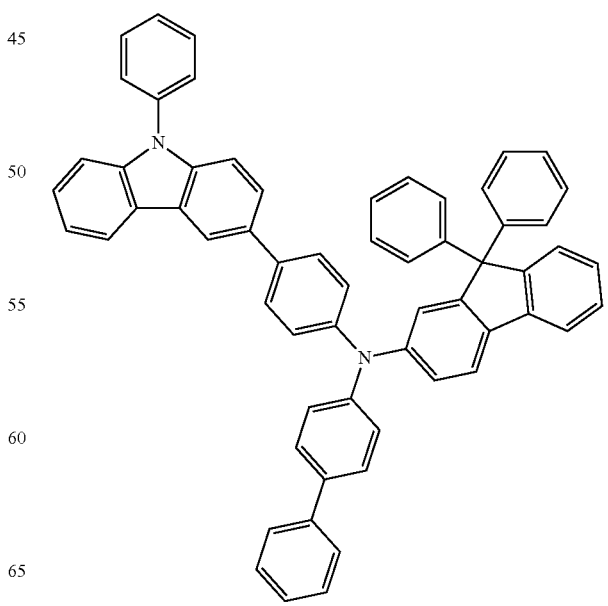
313

314
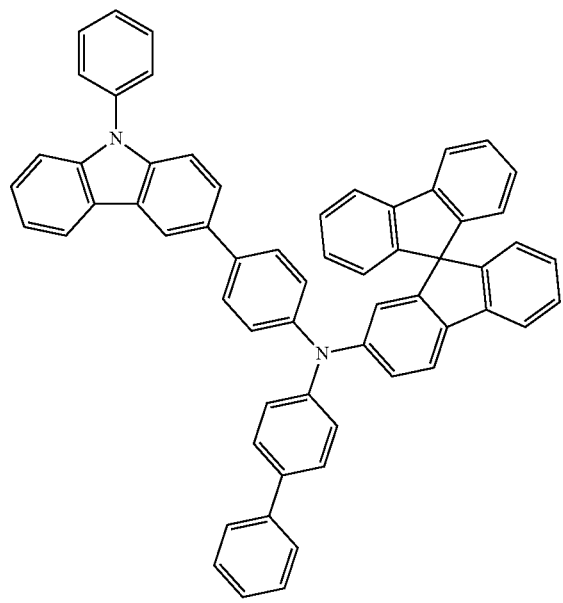
315
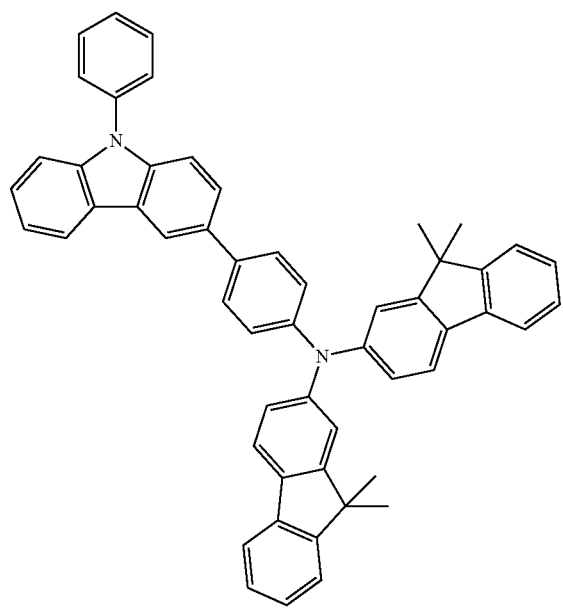
316
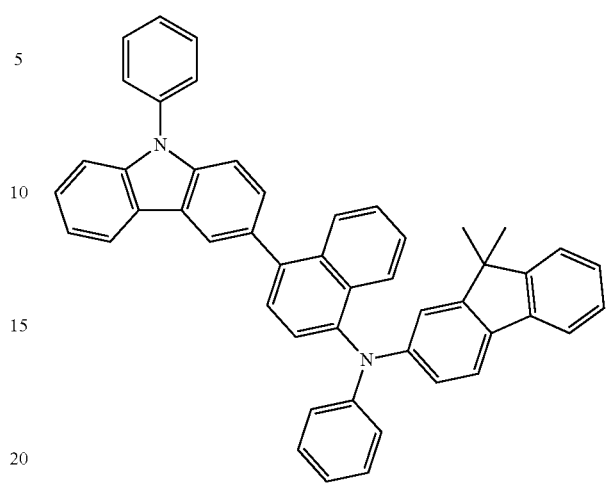
317
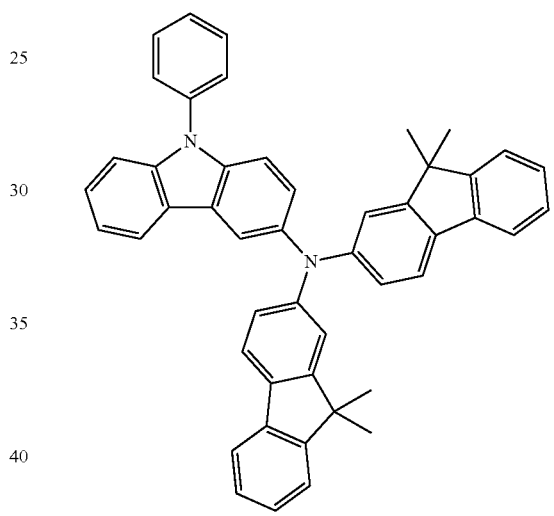
318
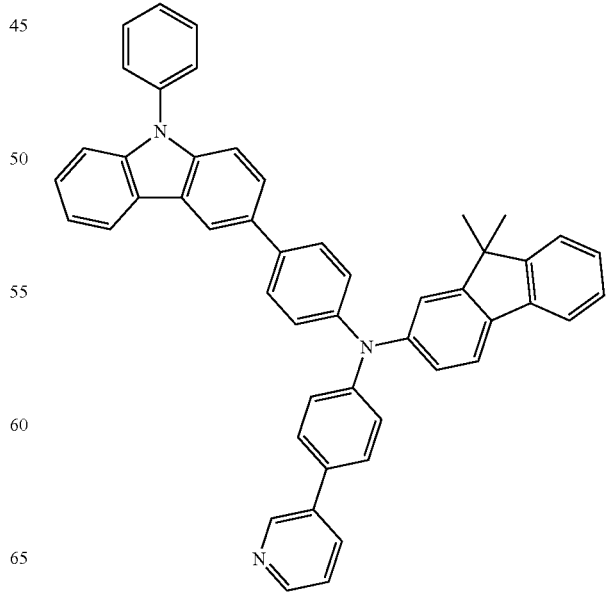

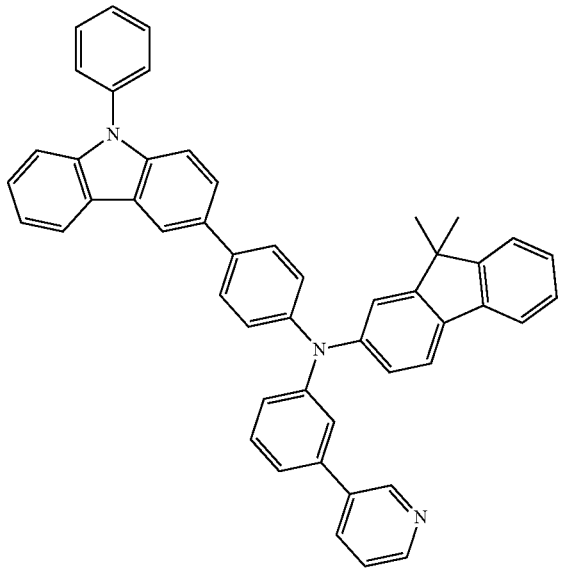

319

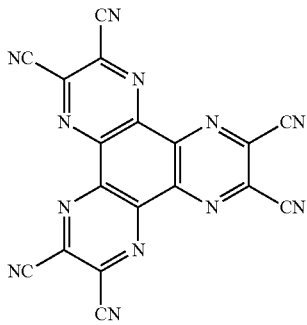

<Formula 200>

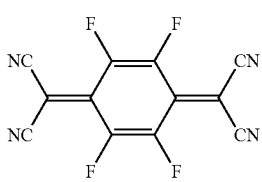

<F4-TCNQ>

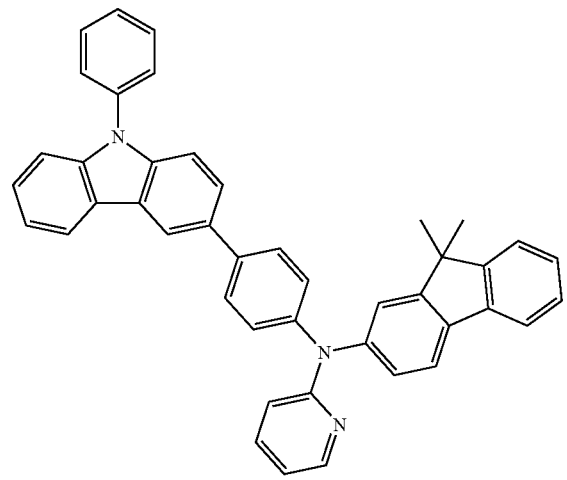

320

In addition to hole-injecting materials, hole-transporting materials, and/or H-functional materials having both hole injection and hole transport capabilities, at least one of the HIL, HTL, and the H-functional layer may further include a charge-generating material to improve the conductivity of the film.

The charge-generating material may be, for example, a p-dopant. The p-dopant may be one of a quinone derivative, a metal oxide, or a compound with a cyano group, but is not limited thereto. Non-limiting examples of the p-dopant include quinone derivatives such as tetracyanoquinodimethane (TCNQ) and 2,3,5,6-tetrafluoro-tetracyano-1,4-benzoquinodimethane (F4-TCNQ); metal oxides such as a tungsten oxide and a molybdenum oxide; and cyano group-containing compounds such as Compound 200 below.

When the HIL, the HTL, or the H-functional layer further includes the charge-generating material, the charge-generating material may be homogeneously dispersed or non-homogeneously distributed in the layer.

A buffer layer may be disposed between the EML and at least one of the HIL, HTL, and the H-functional layer. The buffer layer may compensate for an optical resonance distance of light according to a wavelength of the light emitted from the EML, and thus may increase efficiency. The buffer layer may include any hole injecting material or hole transporting material generally used in OLEDs. In some other embodiments, the buffer layer may include the same material as one of the materials included in the HIL, the HTL, or the H-functional layer that underlie the buffer layer.

Then, the EML may be formed on the HIL, the H-functional layer, or the buffer layer by vacuum deposition, spin coating, casting, LB deposition, or the like. When the EML is formed using vacuum deposition or spin coating, the deposition or coating conditions may be similar to those described above for formation of the HIL, although the conditions for deposition or coating may vary depending on the material used to form the EML.

The EML may include the compound of Formula 1 as described above. For example, the compound of Formula 1 may be used as a host or a dopant. In addition to the compound of Formula 1, the EML may be formed using a variety of light-emitting materials, for example, a host and a dopant. In regard to the dopant, both a fluorescent dopant and a phosphorescent dopant may be used Examples of the host include $Alq_3$, 4,4'-N,N'-dicarbazole-biphenyl (CBP), poly(n-vinylcarbazole) (PVK), 9,10-di (naphthylene-2-yl)anthracene (ADN), TCTA, 1,3,5-tris(N-phenylbenzimidazole-2-yl)benzene (TPBI), 3-tert-butyl-9, 10-di(naphth-2-yl)anthracene (TBADN), E3, distyrylarylene (DSA), dmCBP (see Formula below), and Compounds 501 to 509 below, but the host is not limited thereto.

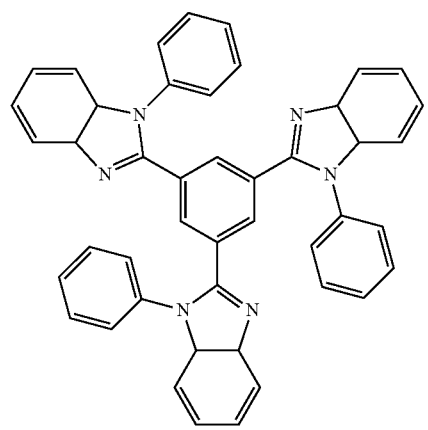
TPBI
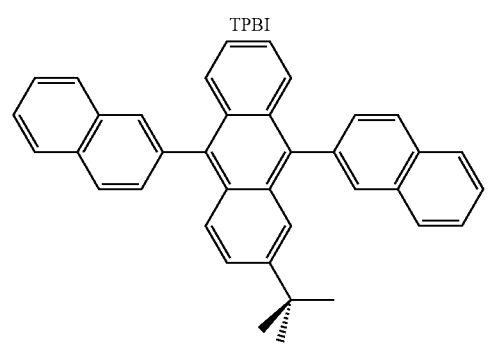
TBADN
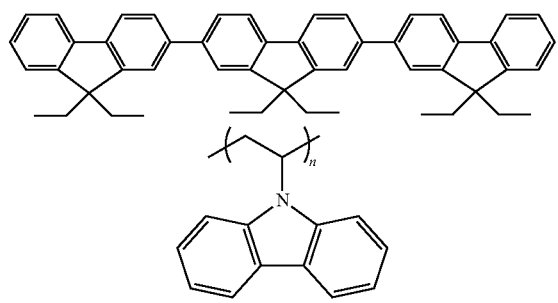
PVK
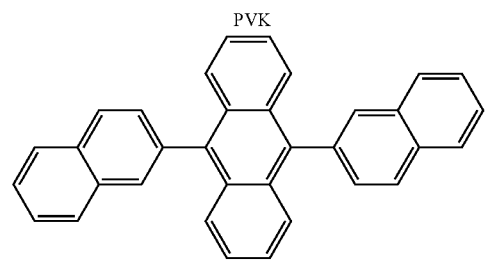
ADN
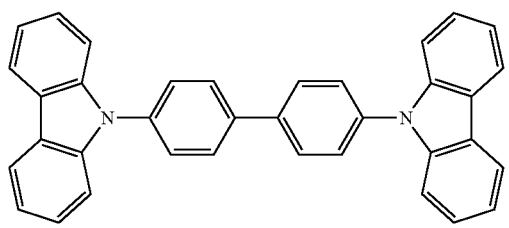
CBP
-continued
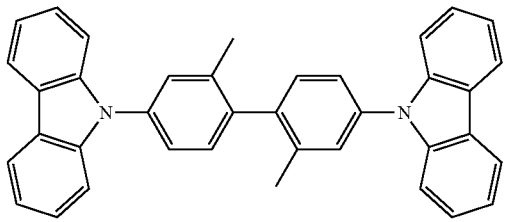
dmCBP
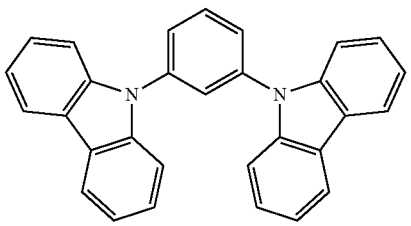
501
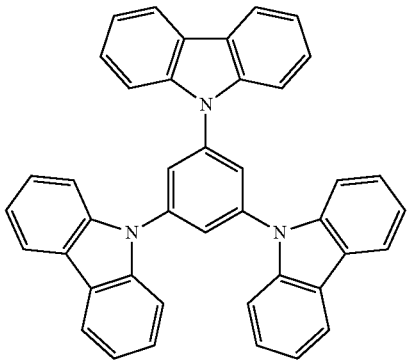
502
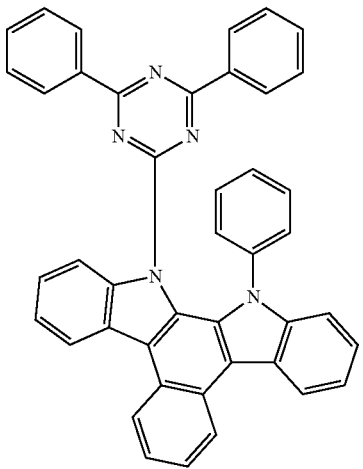
503

504
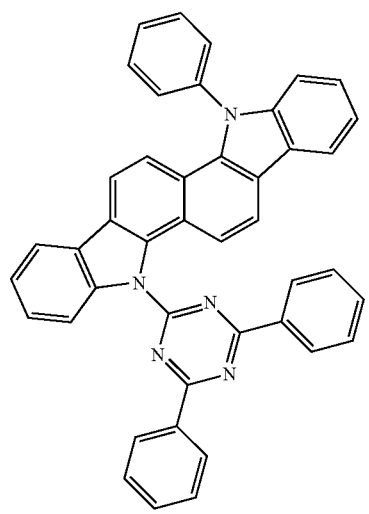

505
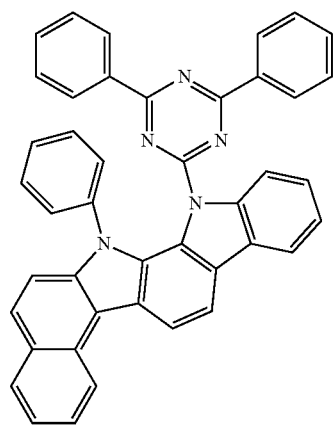

506
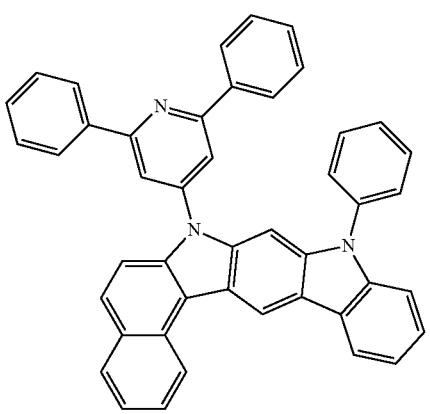

507
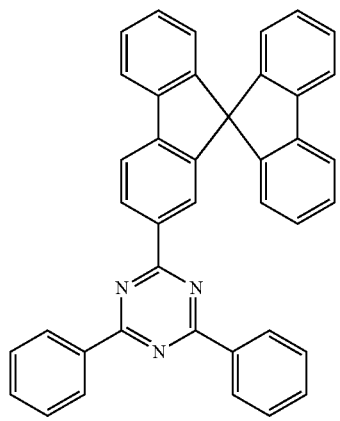

508
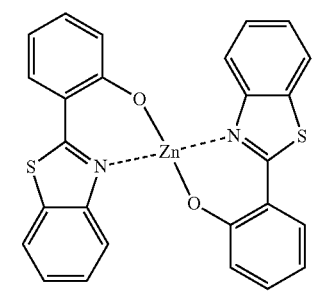

509
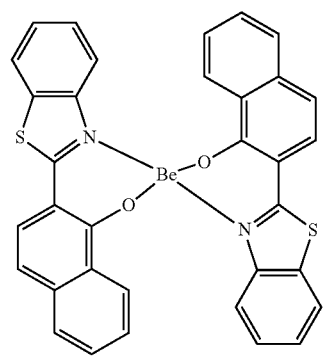

In some embodiments, an anthracene-based compound represented by Formula 400 below may be used as the host.

<Formula 400>
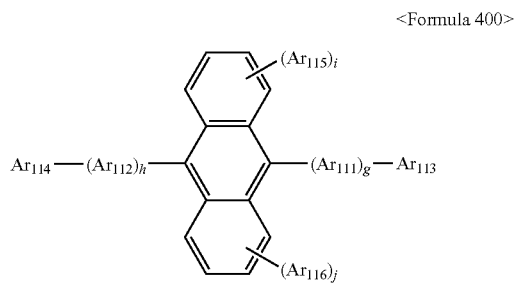

In Formula 400, $Ar_{111}$ and $Ar_{112}$ may each independently be a substituted or unsubstituted $C_5$-$C_{60}$ arylene group. $Ar_{113}$ to $Ar_{116}$ may each independently be a substituted or unsubstituted $C_1$-$C_{10}$ alkyl group or a substituted or unsubstituted $C_5$-$C_{60}$ aryl group. g, h, i and j may each independently be an integer from 0 to 4.

For example, $Ar_{111}$ and $Ar_{112}$ in Formula 400 may each independently be a phenylene group, a naphthalene group, a phenanthrenylene group, or a pyrenylene group; or a phenylene group, a naphthalene group, a phenanthrenylene group, or a pyrenylene group substituted with at least one of a phenyl group, a naphthyl group, or an anthryl group. However, $Ar_{111}$ and $Ar_{112}$ are not limited thereto.

g, h, i, and j in Formula 400 may each independently be 0, 1, or 2.

$Ar_{113}$ to $Ar_{116}$ in Formula 400 may each independently be:

i) a $C_1$-$C_{10}$ alkyl group substituted with at least one of a phenyl group, a naphthyl group, or an anthryl group; or ii) a phenyl group, a naphthyl group, an anthryl group, a pyrenyl group, a phenanthrenyl group, or a fluorenyl group; or iii) a phenyl group, a naphthyl group, an anthryl group, a pyrenyl group, a phenanthrenyl group, or a fluorenyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, or a fluorenyl group; or

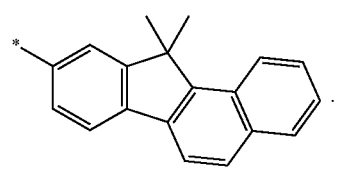 [SMILES: *c1ccc2c(c1)C(C)(C)c1c-2ccc2ccccc12]

However, $Ar_{113}$ to $Ar_{116}$ are not limited thereto.

For example, the anthracene-based compound represented by Formula 400 above may be one of the following compounds, but is not limited thereto:

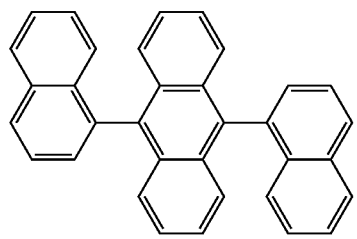

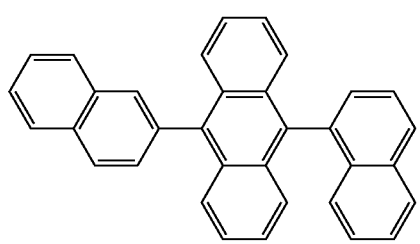

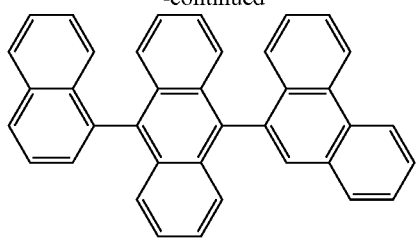

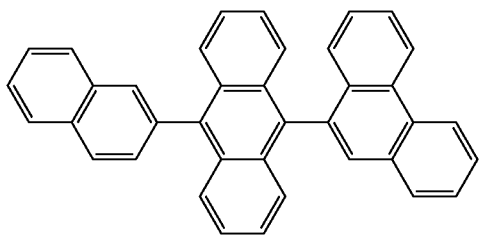

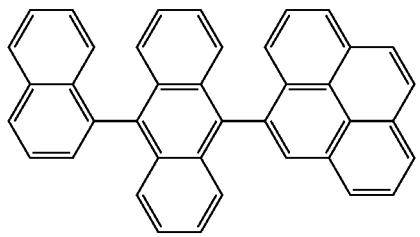

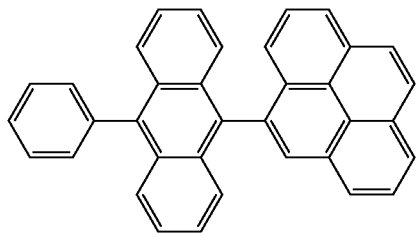

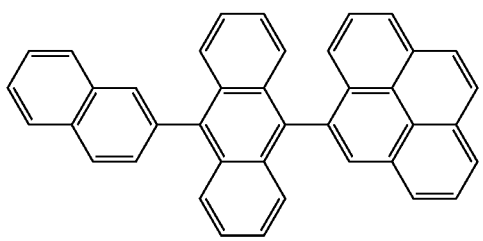

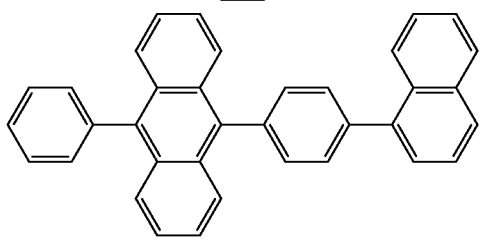

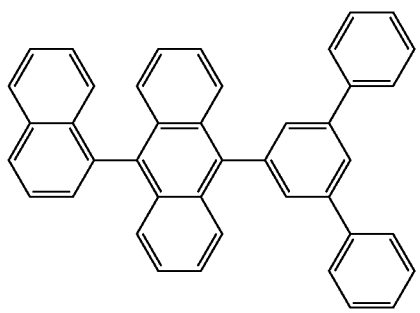

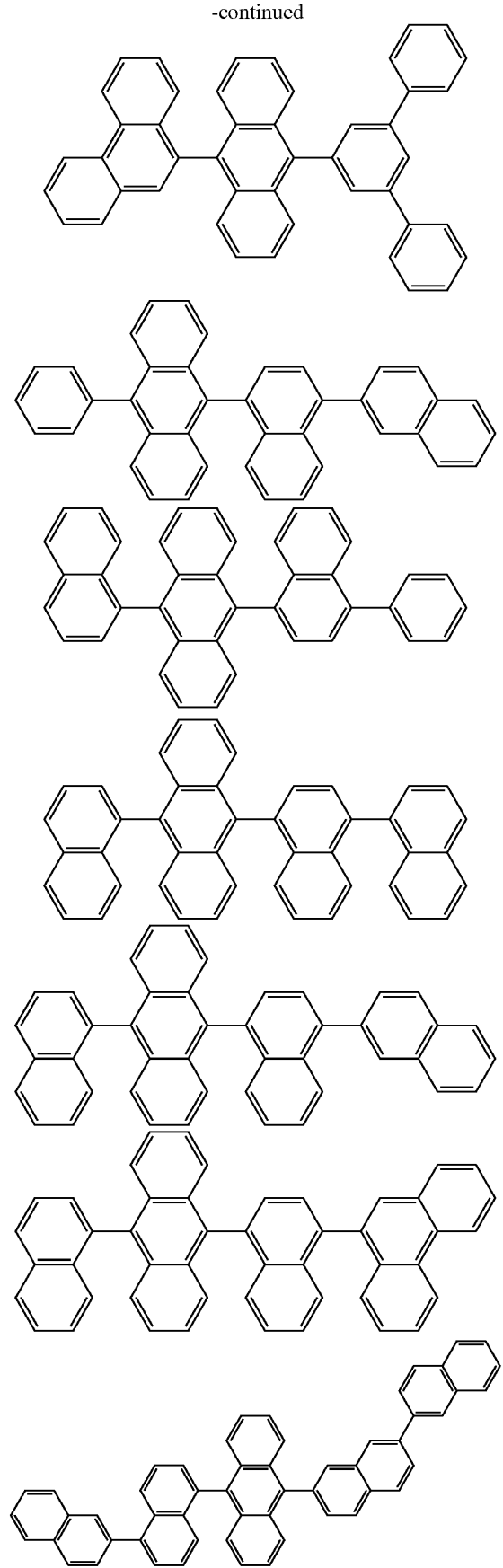
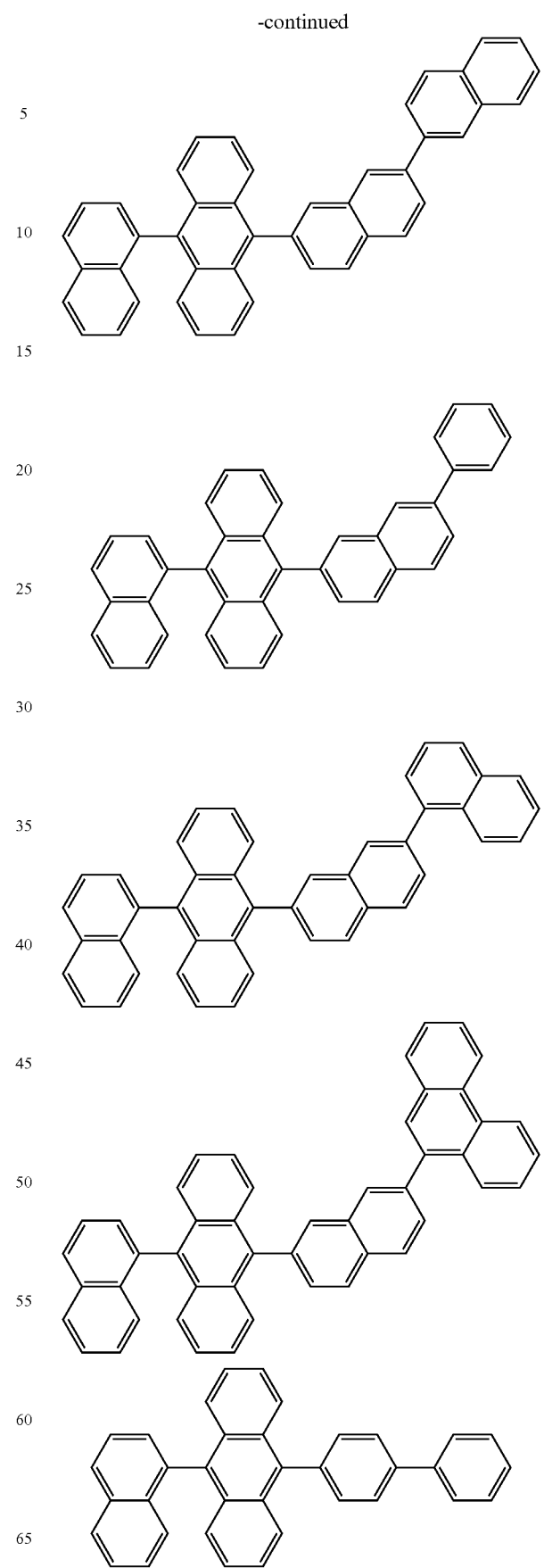

71
-continued
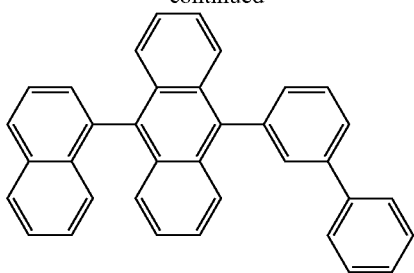
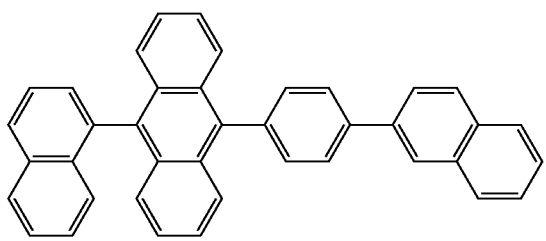
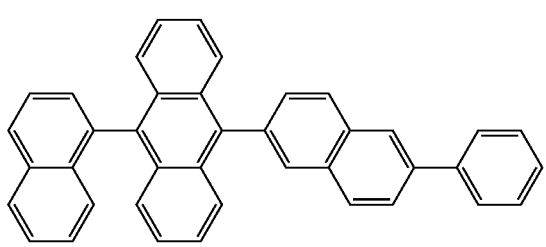
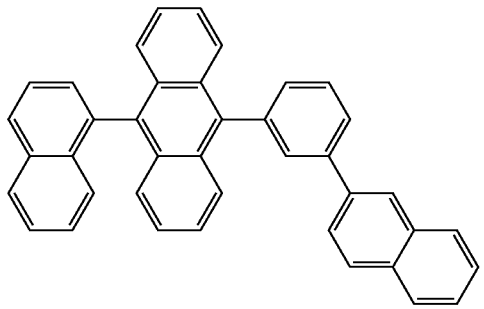
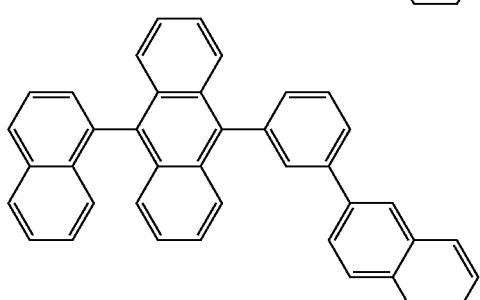
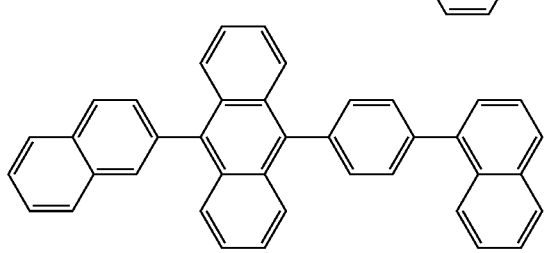
72
-continued
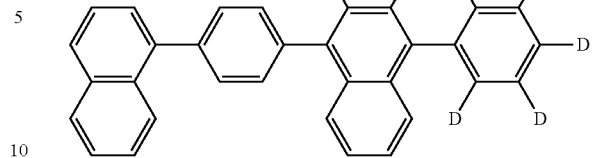
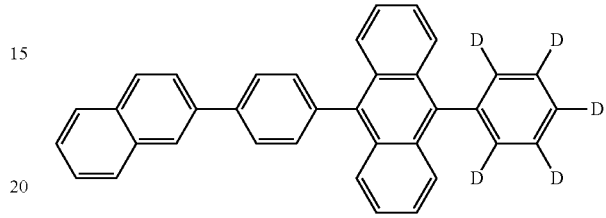
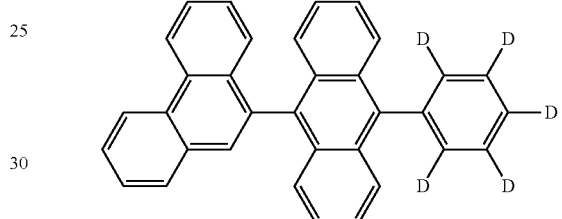
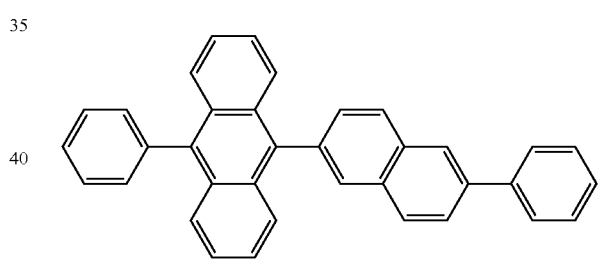
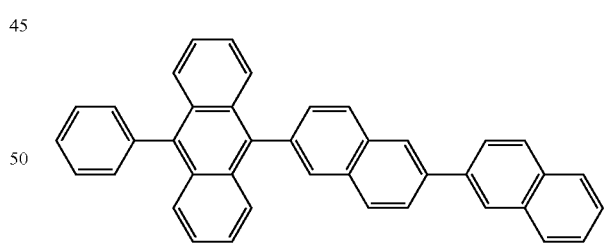
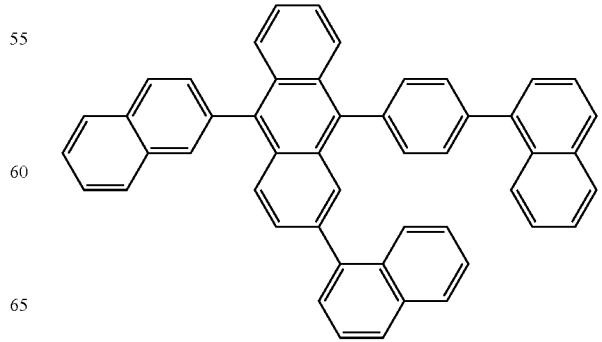

-continued

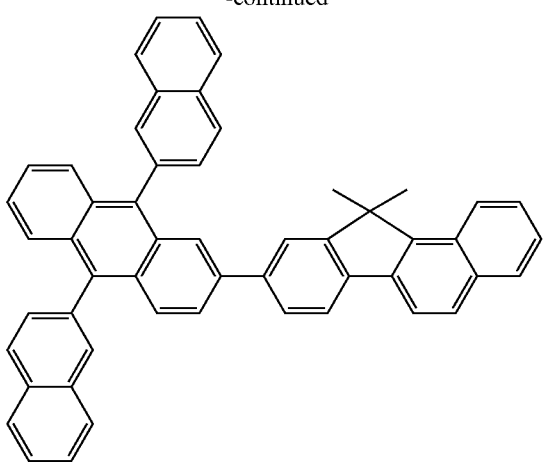

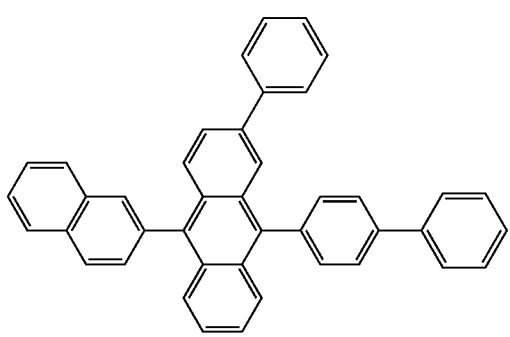

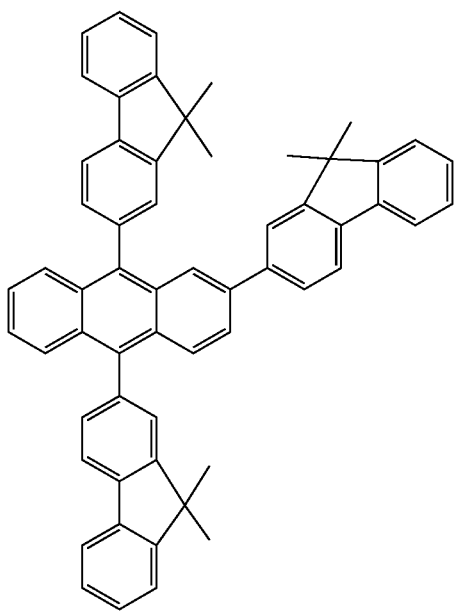

-continued

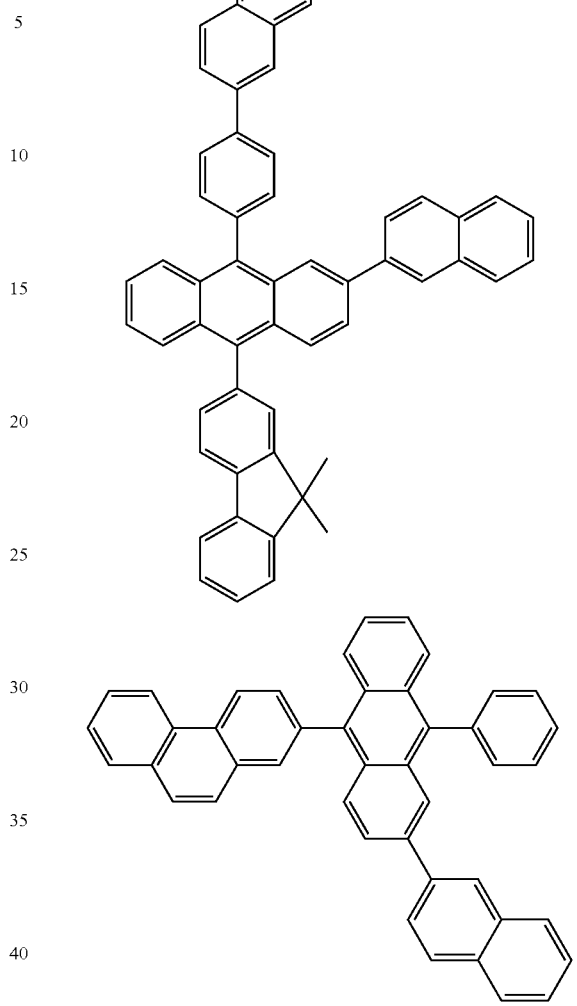

In some embodiments, an anthracene-based compound represented by Formula 401 below may be used as the host:

<Formula 401>

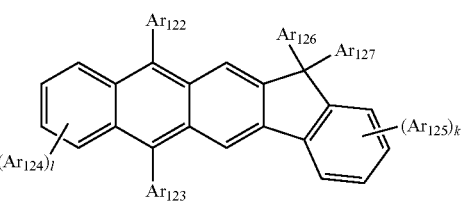

$Ar_{122}$ to $Ar_{125}$ in Formula 401 are the same as $Ar_{113}$ in Formula 400, and thus detailed descriptions thereof will not be repeated here.

$Ar_{126}$ and $Ar_{127}$ in Formula 401 may each independently be a $C_1$-$C_{10}$ alkyl group (e.g., a methyl group, an ethyl group, or a propyl group).

k and l in Formula 401 may each independently be an integer of 0 to 4. For example, k and l may be 0, 1, or 2.

In some embodiments, the anthracene-based compound represented by Formula 401 may be one of the following compounds, but is not limited thereto:

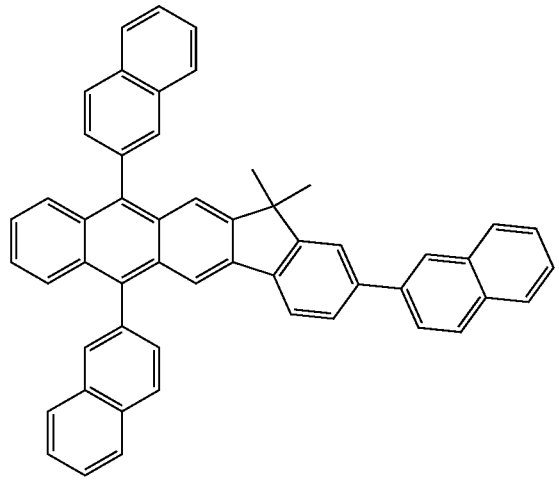

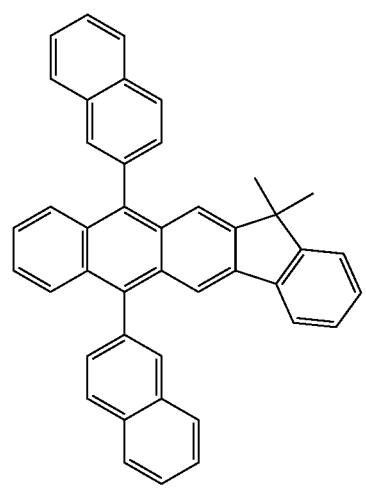

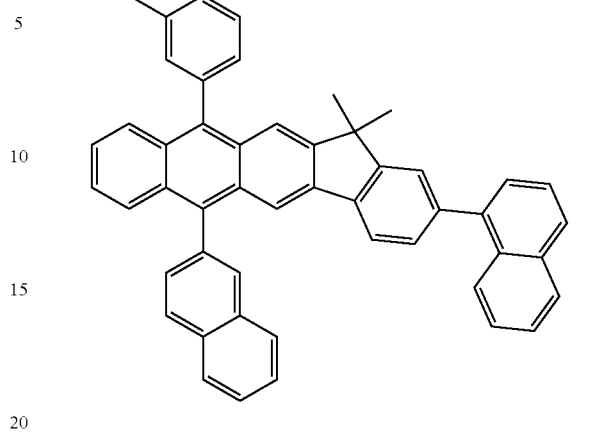

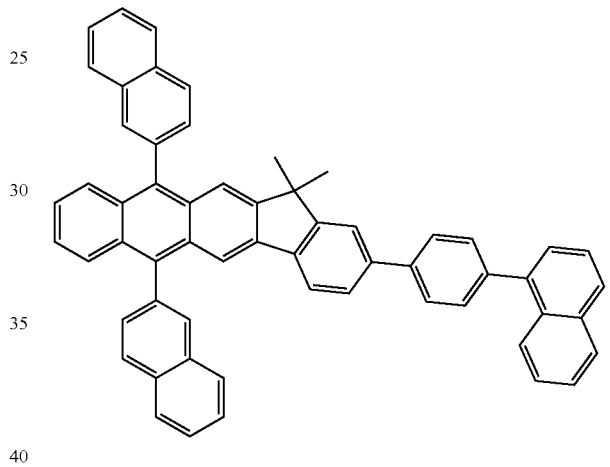

When the OLED is a full color OLED, the EML may be patterned into a red EML, a green EML, and a blue EML.

At least one of the red EML, the green EML, and the blue EML may include one of the following dopants below (ppy=phenylpyridine).

Examples of the blue dopant include the following compounds, but are not limited thereto.

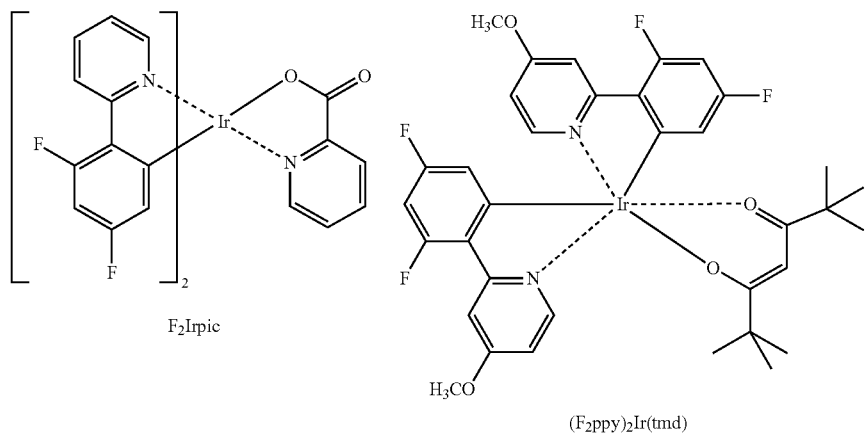

F₂Irpic (F₂ppy)₂Ir(tmd)

-continued
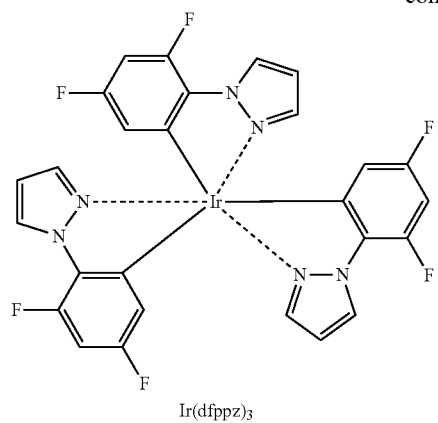
Ir(dfppz)₃
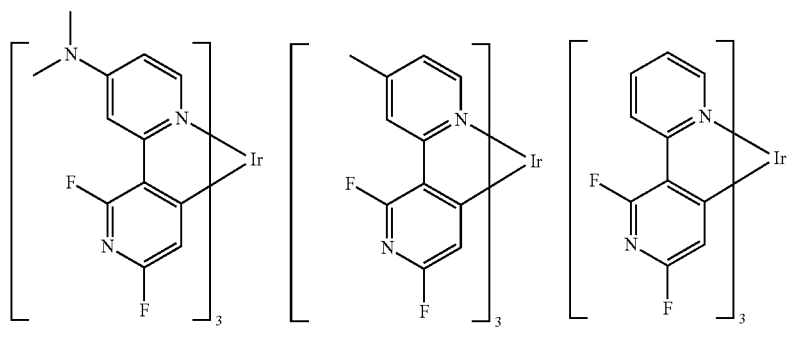
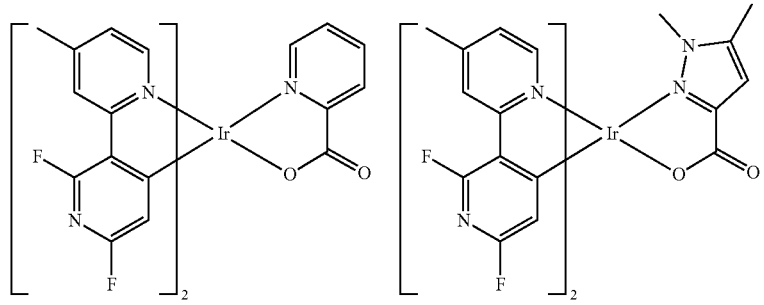
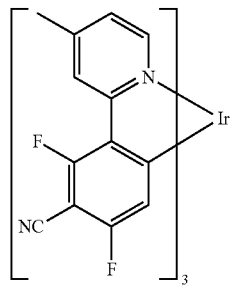
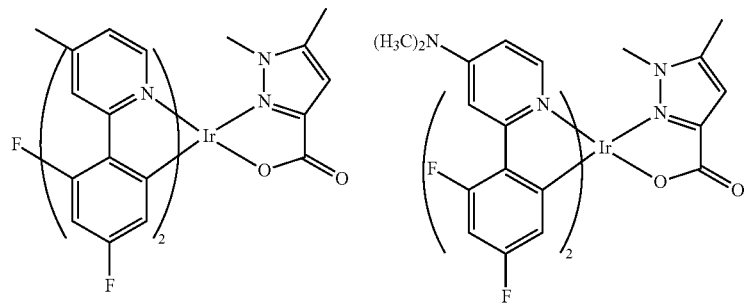

-continued
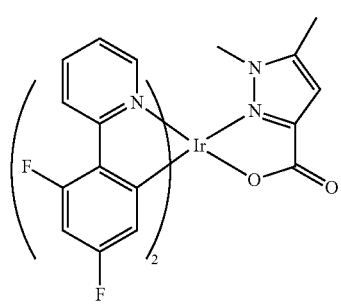
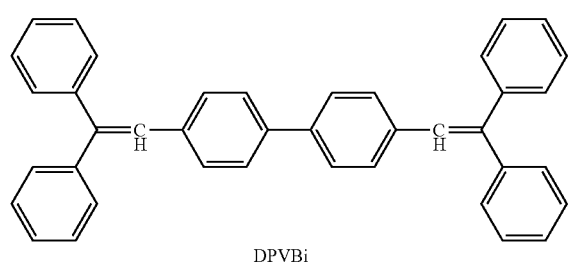
DPVBi
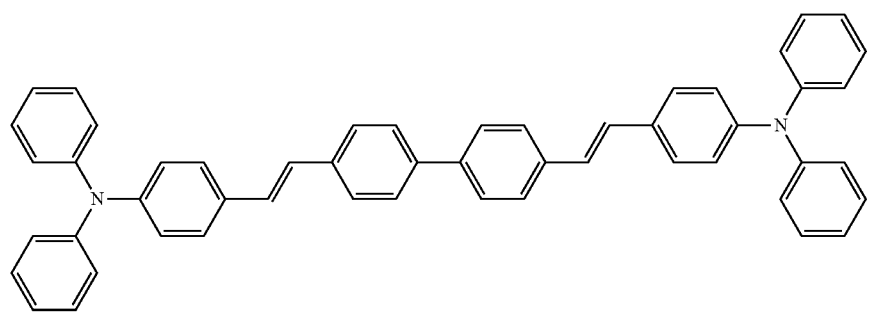
DPAVBi
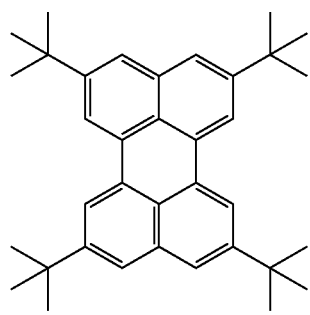
TBPe

Examples of the red dopant include the following compounds, but are not limited thereto:
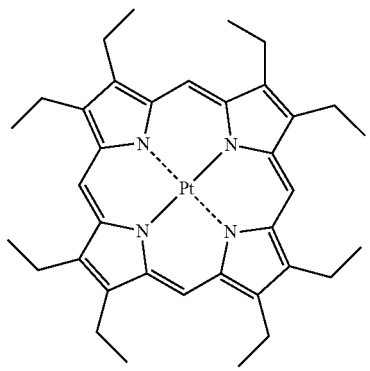
PtOEP
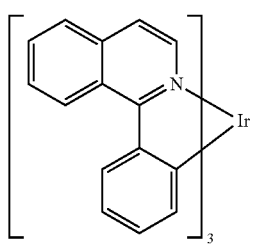
Ir(piq)₃
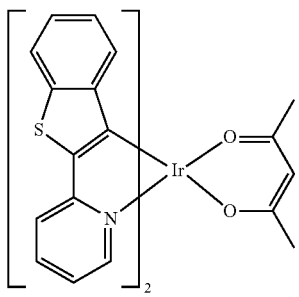
Btp₂Ir(acac)
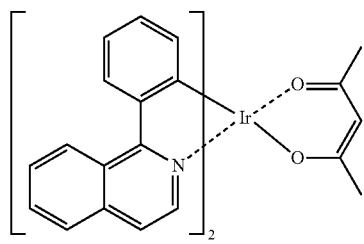
Ir(pq)₂(acac)
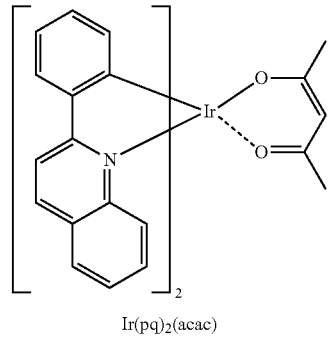
-continued
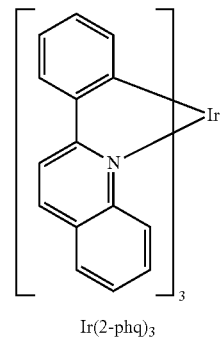
Ir(2-phq)₃
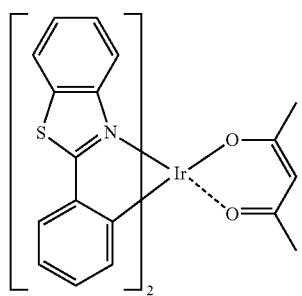
Ir(BT)₂(acac)
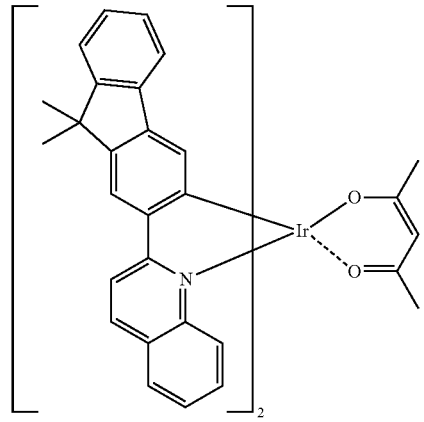
Ir(flq)₂(acac)
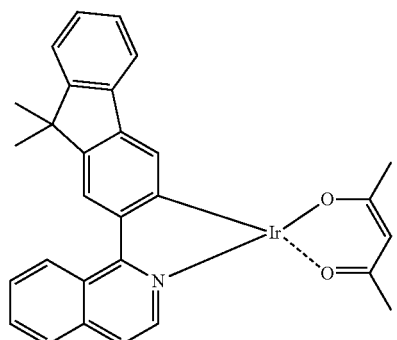
Ir(fliq)₂(acac)

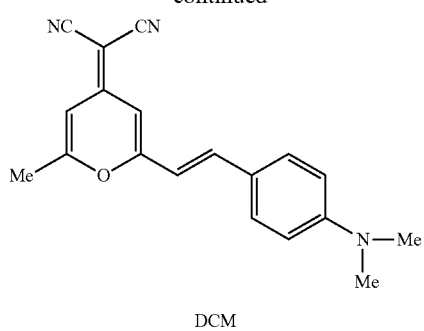
DCM
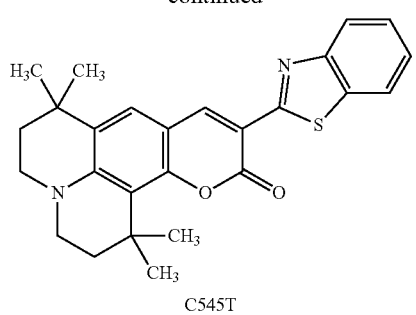
C545T
Examples of dopants that may be used in the EML include Pd-complexes or Pt-complexes represented by the below Formulas, but are not limited thereto:
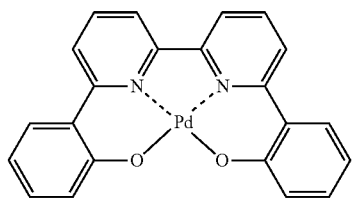
D1
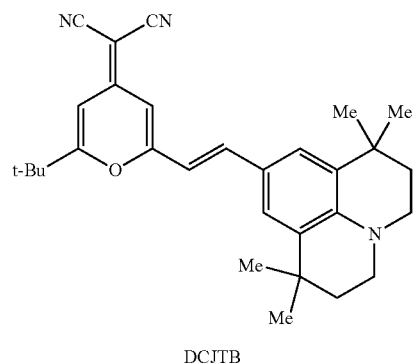
DCJTB
Examples of the green dopant include the following compounds, but are not limited thereto:
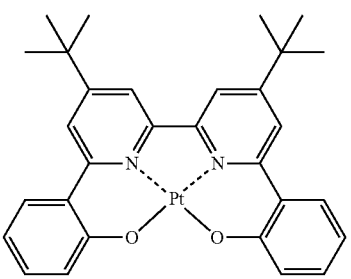
D2
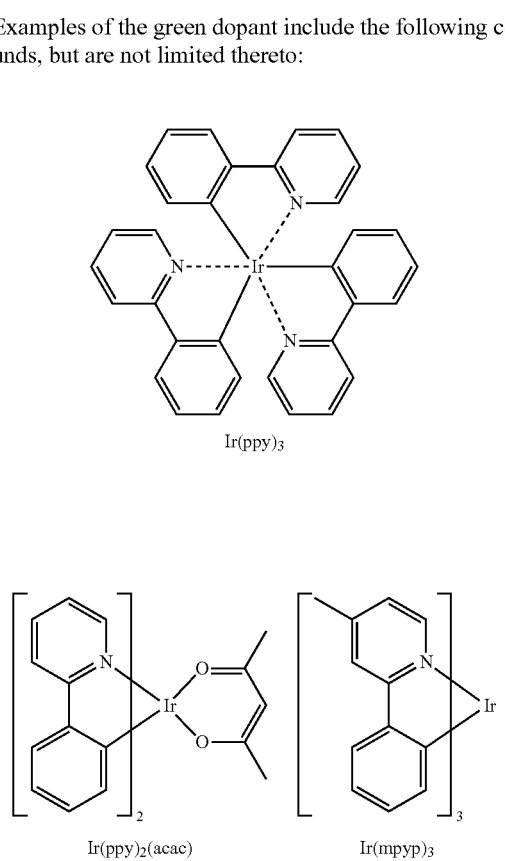
Ir(ppy)₃
Ir(ppy)₂(acac)    Ir(mpyp)₃
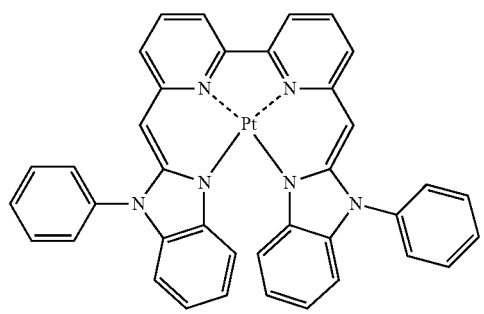
D3
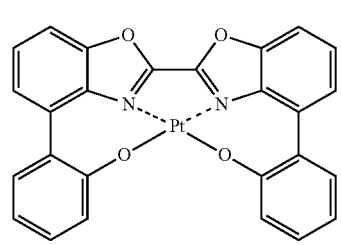
D4

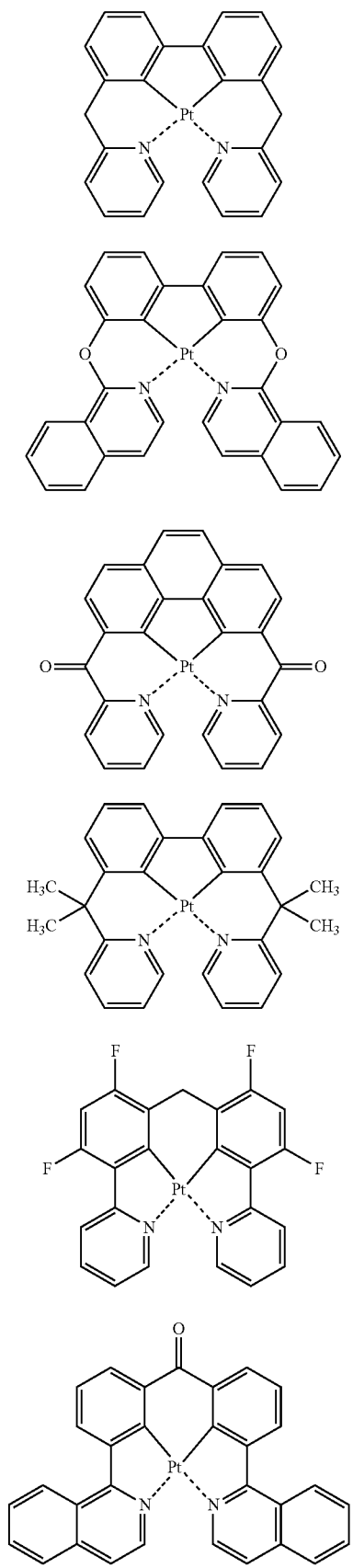
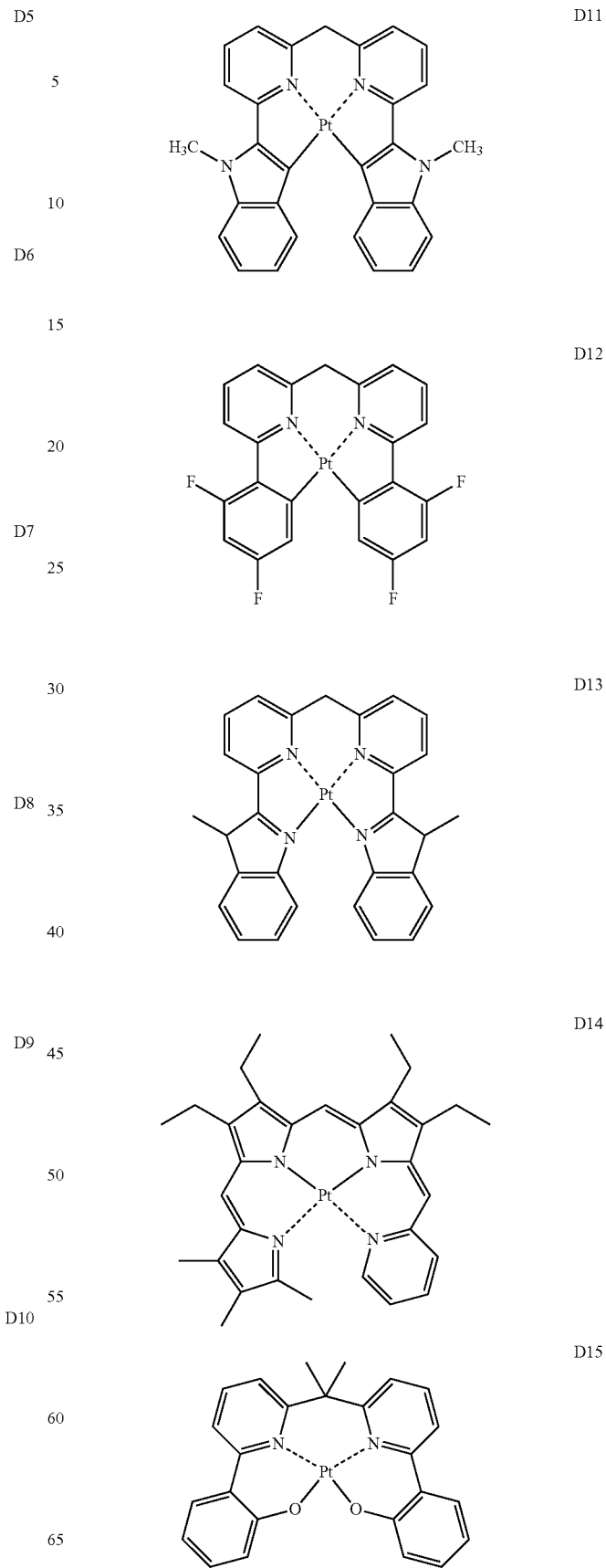

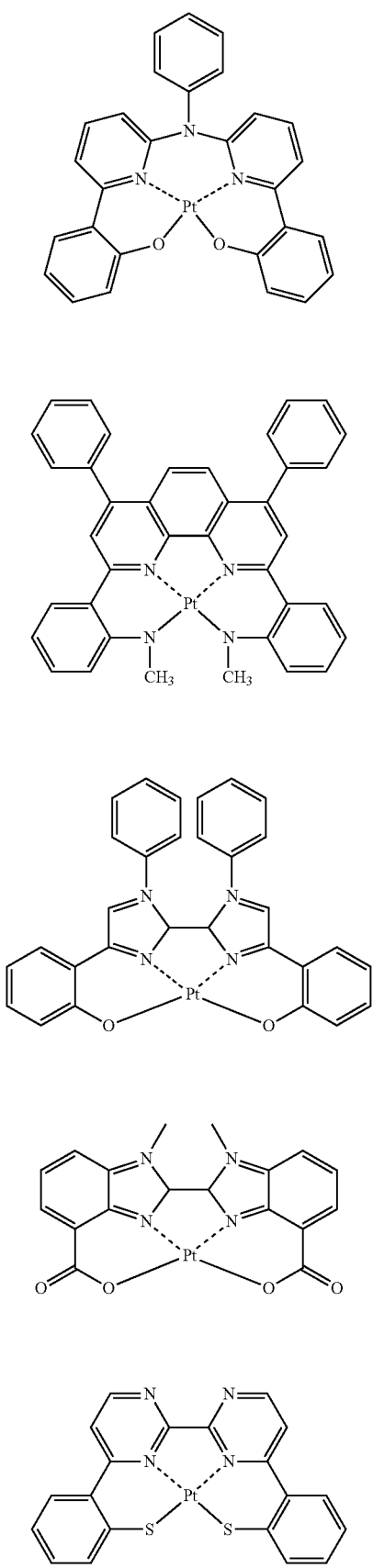
D16
D17
D18
D19
D20
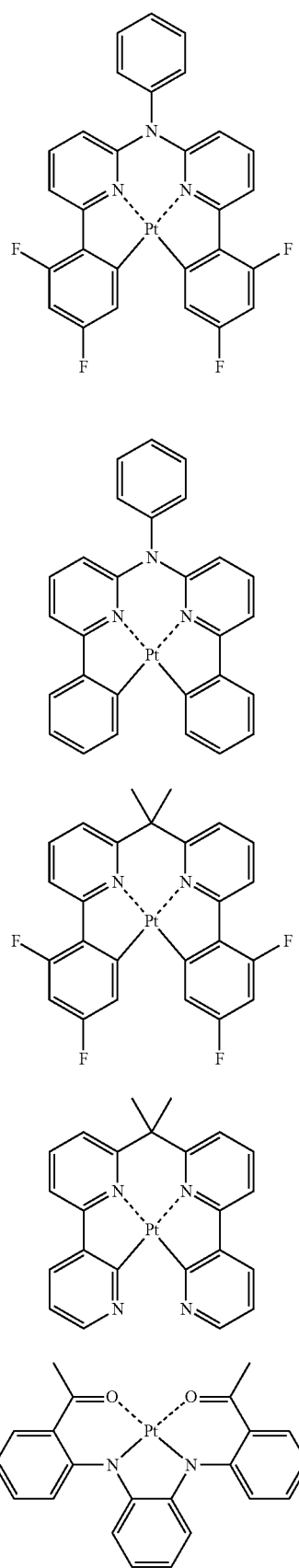
D21
D22
D23
D24
D25
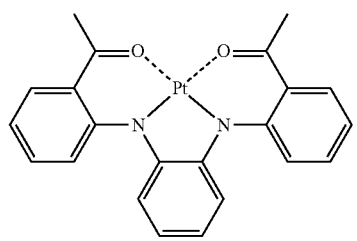

-continued
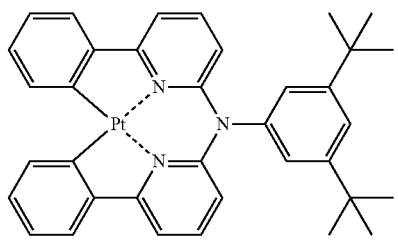 D26
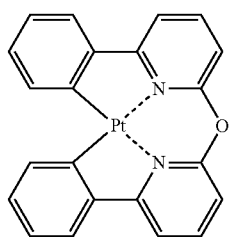 D27
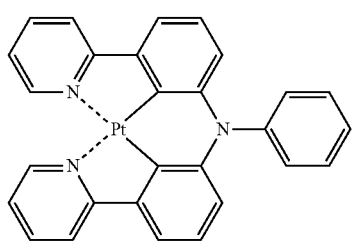 D28
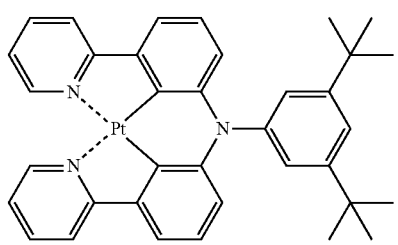 D29
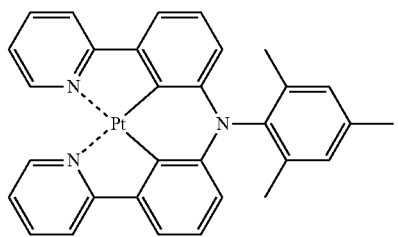 D30
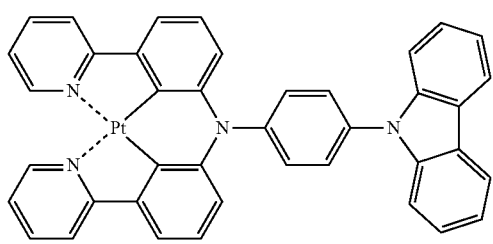 D31
-continued
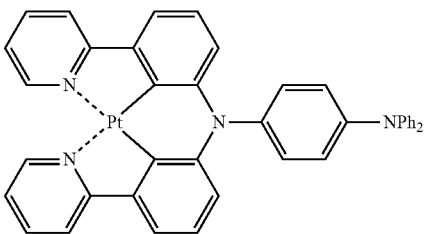 D32
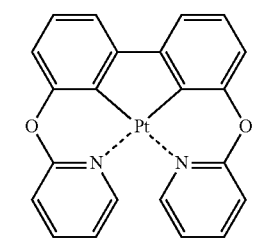 D33
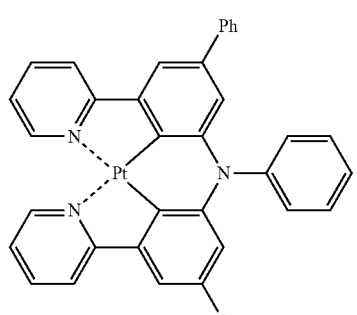 D34
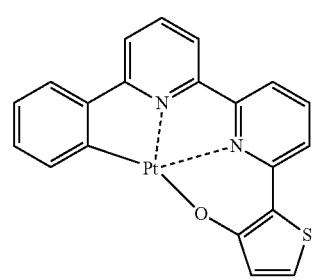 D35
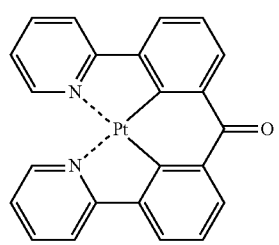 D36

D37
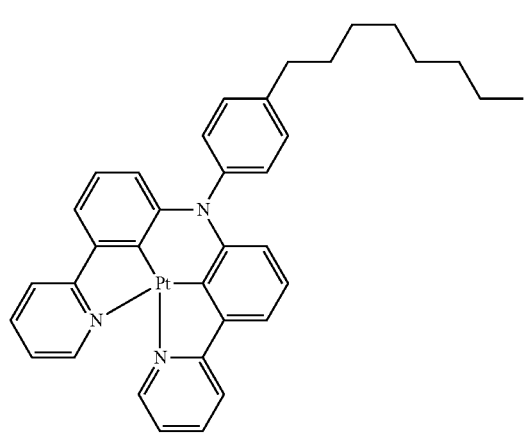
D38
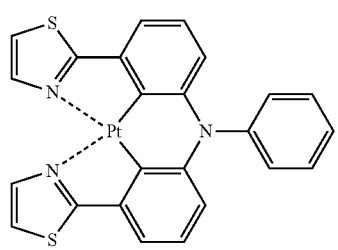
D39
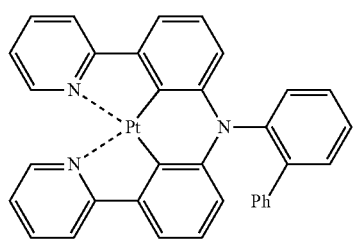
D40
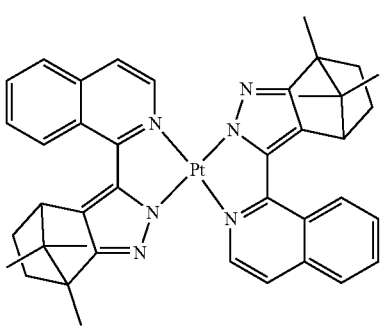
D41
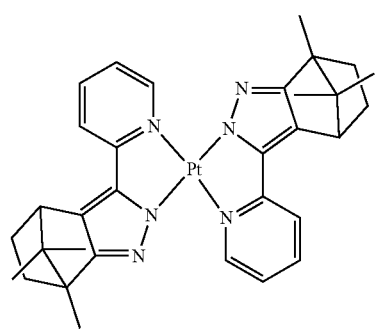
D42
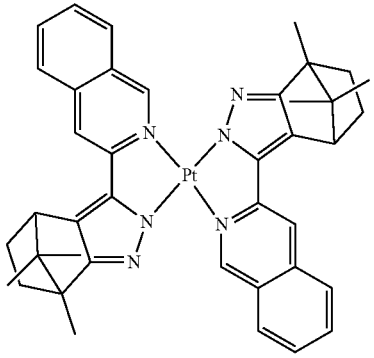
D43
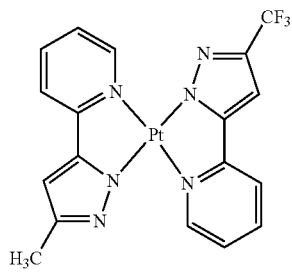
D44
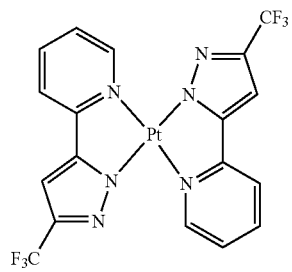
D45
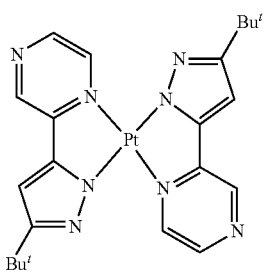
D46
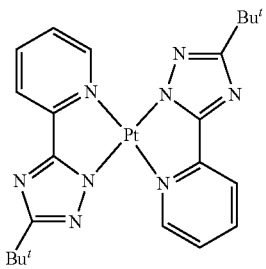

-continued

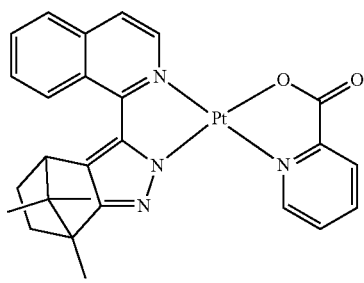
D47

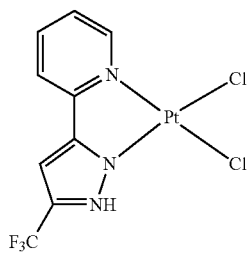
D48

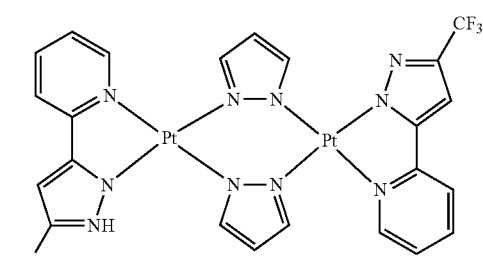
D49

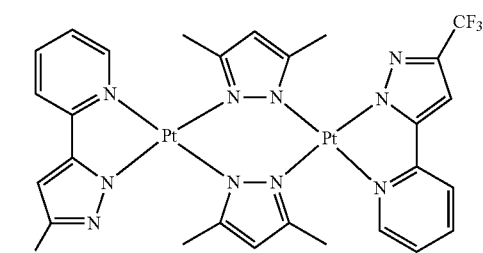
D50

Examples of dopants that may be used in the EML include Os-complexes represented by the below Formulas, but are not limited thereto:

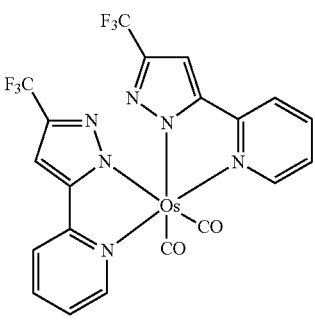

-continued

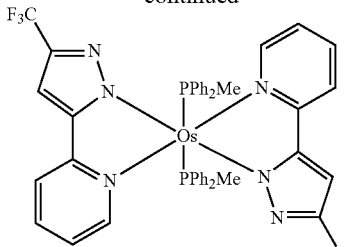

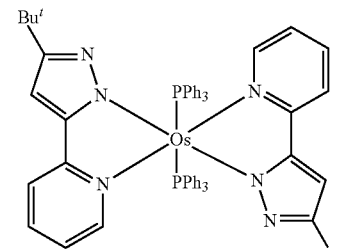

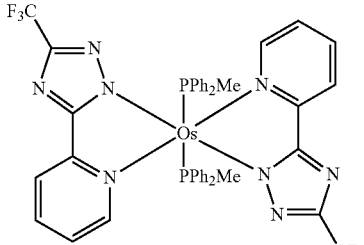

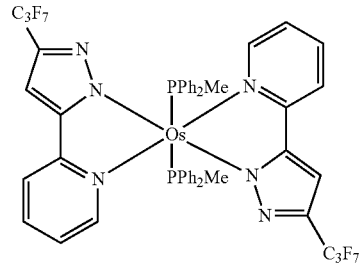

When the EML includes a host and a dopant, the amount of the dopant may be about 0.01 to about 15 parts by weight based on 100 parts by weight of the host, but the amount of the dopant is not limited thereto.

A thickness of the EML may be about 100 Å to about 1,000 Å, for example, about 200 Å to about 600 Å. When the thickness of the EML is within these ranges, the EML may have good light-emitting ability without a substantial increase in driving voltage.

Then, an ETL may be formed on the EML by vacuum deposition, spin coating, casting, or the like. When the ETL is formed using vacuum deposition or spin coating, the deposition or coating conditions may be similar to those described above for the formation of the HIL, although the deposition or coating conditions may vary depending on the compound used to form the ETL.

A material for forming the ETL may be any material that can stably transport electrons injected from an electron-injecting electrode (cathode). Examples of the materials for forming the ETL include a quinoline derivative such as tris (8-quinolinorate)aluminum ($Alq_3$), TAZ, BAlq, beryllium bis (benzoquinolin-10-olate) ($Bebq_2$), 9,10-di(naphthalene-2-yl) anthracene ADN, Compound 201, and Compound 202, but the material for forming the ETL is not limited thereto:

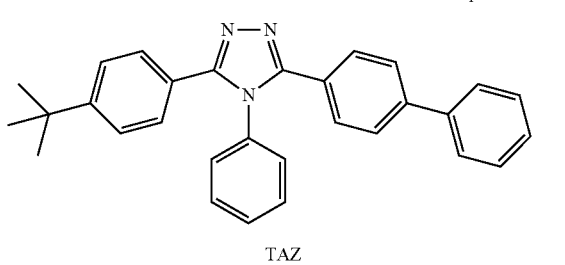

<Compound 201>

TAZ

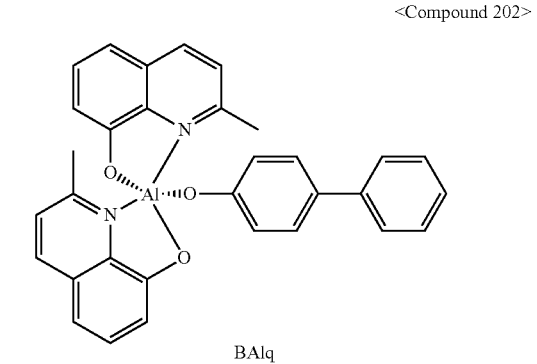

<Compound 202>

BAlq

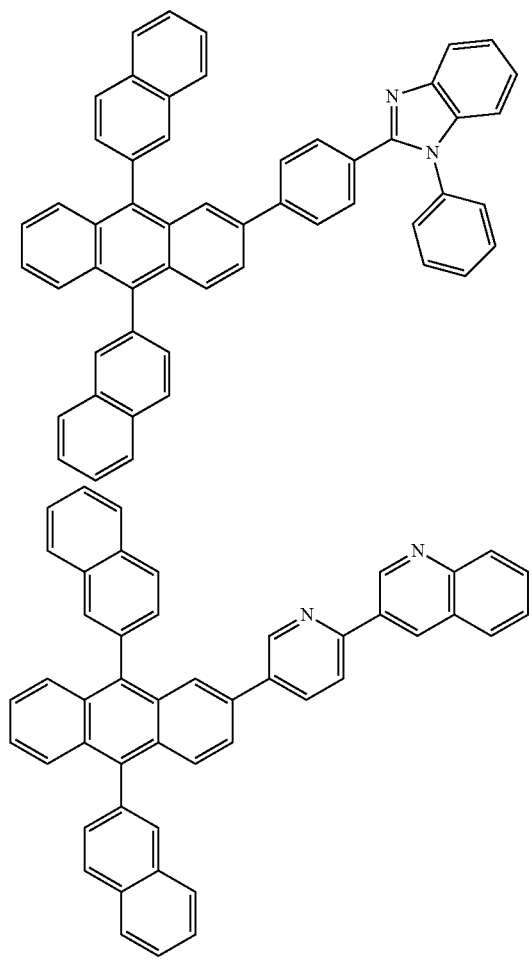

A thickness of the ETL may be about 100 Å to about 1,000 Å, for example, about 150 Å to about 500 Å. When the thickness of the ETL is within these ranges, the ETL may have satisfactory electron transporting ability without a substantial increase in driving voltage.

In some embodiments, the ETL may further include a metal-containing material in addition to the electron transporting organic compound.

The metal-containing material may include a lithium (Li) complex. Non-limiting examples of the Li complex include lithium quinolate (LiQ) and Compound 203 below:

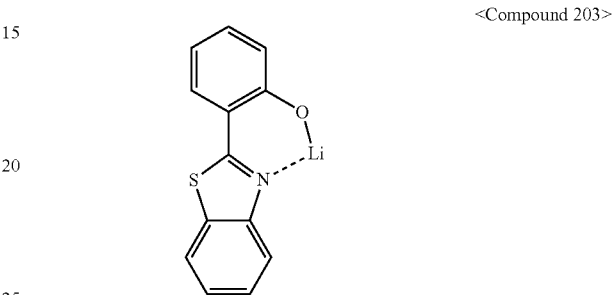

<Compound 203>

Then, an EIL, which facilitates injection of electrons from the cathode, may be formed on the ETL. Any suitable electron-injecting material may be used to form the EIL.

Examples of materials for forming the EIL include LiF, NaCl, CsF, $Li_2O$, and BaO. The deposition conditions of the EIL may be similar to those described above for the formation of the HIL, although the conditions may vary depending on the material used to form the EIL.

A thickness of the EIL may be about 1 Å to about 100 Å, for example, about 3 Å to about 90 Å. When the thickness of the EIL is within these ranges, the EIL may have satisfactory electron injection ability without a substantial increase in driving voltage.

A second electrode is disposed on the organic layer. The second electrode may be a cathode, which is an electron injection electrode. A material for forming the second electrode may be a metal, an alloy, or an electro-conductive compound (which are materials having low work functions), or a mixture thereof. For example, the second electrode may be formed of lithium (Li), magnesium (Mg), aluminum (Al), aluminum-lithium (Al—Li), calcium (Ca), magnesium-indium (Mg—In), magnesium-silver (Mg—Ag), or the like, and may be formed as a thin film type transmission electrode. In some embodiments, to manufacture a top-emission light-emitting diode, the transmission electrode may be formed of indium tin oxide (ITO) or indium zinc oxide (IZO).

Although the OLED according to embodiments of the present invention has been described with reference to FIG. 1, the OLED is not limited to the structure illustrated in FIG. 1.

In addition, when the EML is formed using a phosphorescent dopant, to prevent diffusion of triplet excitons or holes toward the ETL, a hole blocking layer (HBL) may be formed between the ETL and the EML or between the E-functional layer and the EML by, for example, vacuum deposition, spin coating, casting, LB, or the like. When the HBL is formed using vacuum deposition or spin coating, the deposition or coating conditions may be similar to those described above for the formation of the HIL, although the conditions for deposition or coating may vary depending on the material used to form the HBL. Any hole-blocking material may be used. Examples of hole-blocking materials include oxadiazole derivatives, triazole derivatives, and phenanthroline derivatives. For example, BCP (illustrated below) may be used as the material for the HBL.

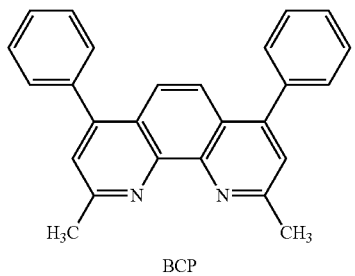 [SMILES: Cc1cc(-c2ccccc2)c2ccc3c(-c4ccccc4)cc(C)nc3c2n1 ; "BCP"]

BCP

A thickness of the HBL may be about 20 Å to about 1,000 Å, for example, about 30 Å to about 300 Å. When the thickness of the HBL is within these ranges, the HBL may have improved hole blocking ability without a substantial increase in driving voltage.

The OLED according to an embodiment of the present invention may be provided in various types of flat panel display devices, such as passive matrix OLED devices and active matrix OLED devices. In particular, when the OLED is provided in an active matrix OLED, the first electrode on the substrate, which acts as a pixel electrode, may be electrically connected to a source electrode or a drain electrode of a thin-film transistor (TFT). In addition, the OLED may be provided in a flat panel display device having double-sided screens.

In some embodiments, the organic layer of the organic light-emitting device (which includes the compound of Formula 1) may be formed by deposition or by a wet process including coating a solution of the compound of Formula 1.

Hereinafter, the present invention will be described with reference to the following synthesis examples and other examples. However, these examples are presented for illustrative purposes only and are not intended to limit the scope of the present invention.

EXAMPLE

Synthesis Example 1

Synthesis of Compound 1

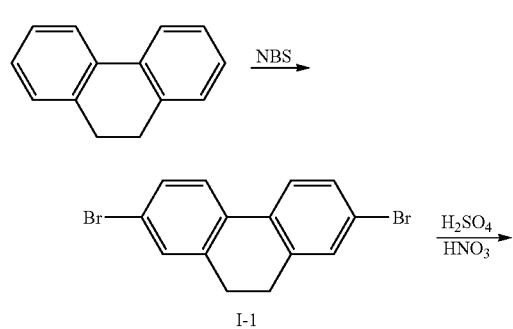

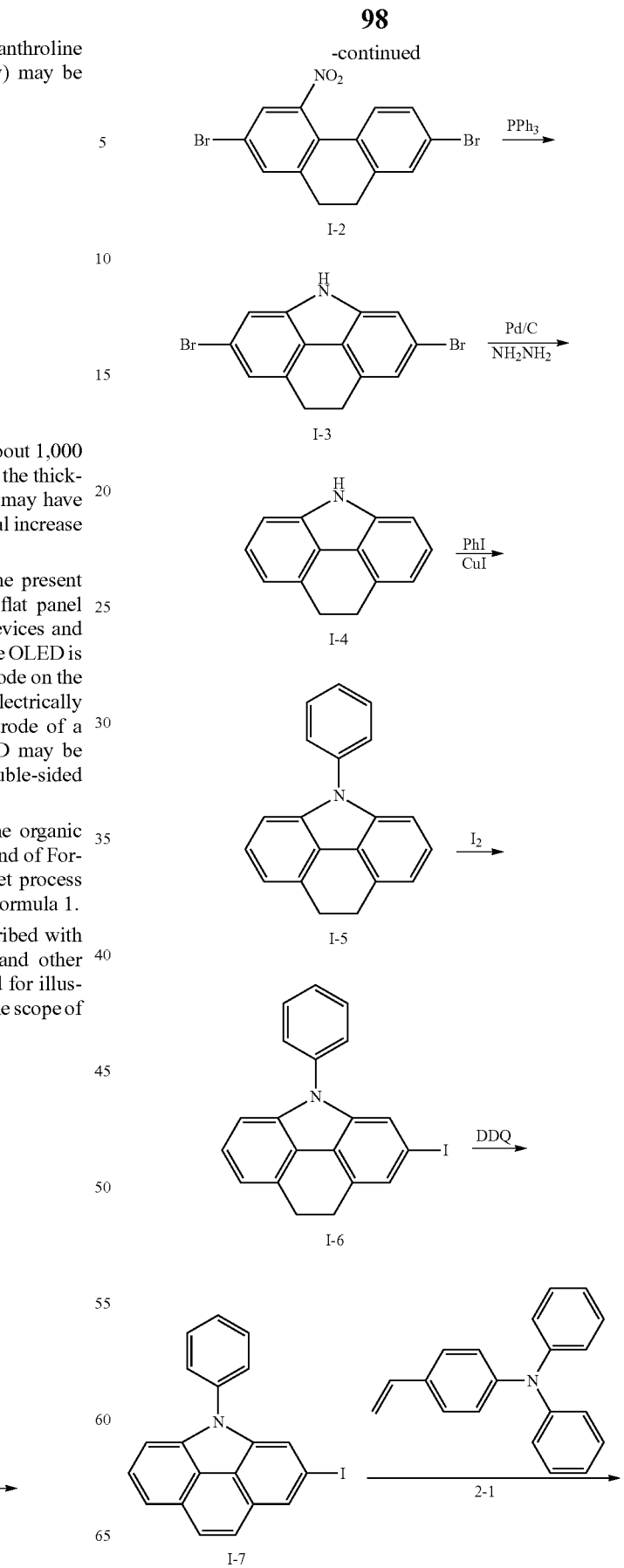

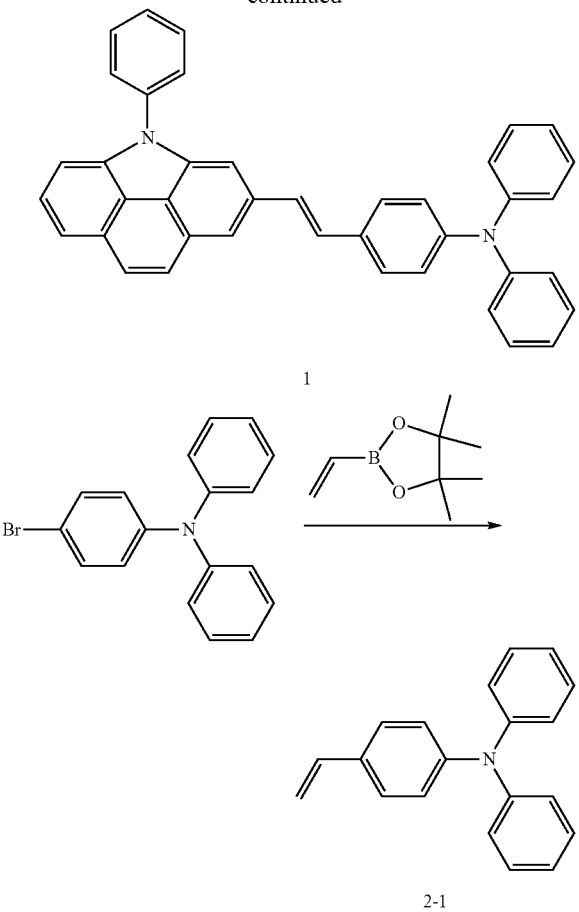

Synthesis of Intermediate I-1

After dissolving 10.0 g (55.4 mmol) of 9,10-dihydrophenanthrene, 21.8 g (121.0 mmol) of N-bromosuccinimide, and 0.5 g (2.7 mmol) of p-TsOH in 30 mL of acetonitrile, the reaction solution was stirred at a temperature of about 50° C. for about 12 hours. The reaction solution was cooled to room temperature, and then stirred for about 30 minutes to precipitate crystals. The crystals obtained by a vacuum filter were washed with methanol to obtain 8.4 g of Intermediate I-1 (Yield: 45%) which was gray in color. The obtained compound was identified by LC-MS ($C_{14}H_{10}Br_2$ $M^+$ 336.9).

Synthesis of Intermediate I-2

After completely dissolving 5.0 g of Intermediate I-1 (15.0 mmol) in 50 mL of dichloromethane, 1.7 g of nitric acid (30.0 mmol) was added thereto at room temperature. Then, 1.5 g of sulfuric acid (15.0 mmol) was slowly added thereto, and then the reaction solution was stirred at a temperature of about 30° C. for about 6 hours. After completion of the reaction, the reaction solution was cooled to room temperature, 50 mL of methanol was added thereto, and the solution was then stirred for about 2 hours to precipitate crystals. The crystals obtained by a vacuum filter were washed with methanol to obtain 5.2 g of Intermediate I-2 (Yield: 90%) which was yellow in color. The obtained compound was identified by LC-MS ($C_{14}H_9Br_2NO_2$ $M^+$ 381.9).

Synthesis of Intermediate I-3

After completely dissolving 4.6 g of Intermediate I-2 (12.0 mmol) in 30 mL of o-dichlorobenzene and heating the reaction solution, 4.7 g of triphenylphosphine (18.0 mmol) was added thereto. Then, the reaction solution was stirred at a temperature of about 180° C. for about 3 hours. After the reaction solution was cooled to room temperature, solvent was evaporated and the residue was separation-purified by silica gel column chromatography and then washed with methanol to obtain 2.9 g of Intermediate I-3 (Yield: 70%) which was white in color. The obtained compound was identified by LC-MS ($C_{14}H_9Br_2N$ $M^+$ 349.9)

Synthesis of Intermediate I-4

After dissolving 10 g of Intermediate I-3 (28.5 mmol) and 0.03 g of Pd/C (10%) (0.28 mmol) in 100 mL of ethanol, the temperature of the reaction solution was increased to 50° C. 5.48 g of hydrazine (171 mmol) was added thereto, and the solution was then stirred for about 24 hours. The reaction solution was cooled to room temperature, and washed with acetone. Then, 100 mL of ice water was added thereto to obtain 3.63 g of Intermediate I-4 (Yield: 66%) which was white in color. The obtained compound was identified by LC-MS ($C_{14}H_{11}N$ M+ 194.1).

Synthesis of Intermediate I-5

After dissolving 1.93 g of Intermediate I-4 (10.0 mmol), 2.5 g of iodobenzene (12.0 mmol), 0.2 g of 1,10-phenanthroline (1.0 mmol), 0.2 g of CuI (2.0 mmol), and 4.1 g of $K_2CO_3$ (30.0 mmol) in 30 mL of N,N-dimethylformamide (DMF), the reaction solution was stirred at a temperature of about 80° C. for about 24 hours. The reaction solution was cooled to room temperature, and then extracted three times with 30 mL of water and 40 mL of diethyl ether. The organic layer obtained therefrom was dried with magnesium sulfate, solvent was evaporated, and the residue was separation-purified by silica gel column chromatography to obtain 2.39 g of Intermediate I-5 (Yield: 89%). The obtained compound was identified by LC-MS ($C_{20}H_{15}N$ $M^+$ 270.1).

Synthesis of Intermediate I-6

After completely dissolving 10 g of Intermediate I-5 (37.1 mmol) in 100 ml of dichloromethane, 3.58 g of iodine (14.1 mmol) and 2.38 g of $KIO_3$ (11.13 mmol) were added thereto in a 1/5 split. The reaction solution was stirred for about 6 hours and then washed with methanol to obtain 8.06 g of Intermediate I-6 (Yield: 55%). The obtained compound was identified by LC-MS ($C_{20}H_{14}IN$ M+ 396.1).

Synthesis of Intermediate I-7

After dissolving 10 g of Intermediate I-6 (25.3 mmol) in 100 ml of toluene in an oxygen atmosphere, 1.57 g of 2,3-dichloro-5,6-dicyano-1,4-benzoquinone (7.6 mmol) and 0.52 g of $NaNO_2$ (7.6 mmol) were added thereto at room temperature. The reaction solution was stirred at a temperature of about 110° C. for about 6 hours, and after cooling the reaction solution to room temperature, the solvent was evaporated and the residue was separation-purified by silica gel column chromatography to obtain 8.94 g of Intermediate I-7 (Yield: 90%). The obtained compound was identified by LC-MS ($C_{20}H_{12}IN$ M+ 394.0)

Synthesis of Intermediate 2-1

After dissolving 3.24 g of 4-bromo-N,N-diphenylaniline (10 mmol), 2.310 g of vinyl-boronic acid pinacol-ester (15 mmol), 0.577 g of Pd(PPh$_3$)$_4$ (0.5 mmol), and 1.658 g of K$_2$CO$_3$ (12 mmol) in 100 mL of THF/H$_2$O (2/1 volume ratio), the reaction solution was stirred at a temperature of about 80° C. for about 5 hours. The reaction solution was cooled to room temperature, and then extracted three times with 40 mL of water and 50 mL of ethyl ether. The organic layer obtained therefrom was dried with magnesium sulfate, the solvent was evaporated, and the residue was separation-purified by silica gel column chromatography to obtain 1.6 g of Intermediate 2-1 (Yield: 59%). The obtained compound was identified by LC-MS (C$_{20}$H$_{17}$N M+ 272.1).

Synthesis of Compound 1

After dissolving 3.93 g of Intermediate I-7 (10 mmol), 2.71 g of Intermediate 2-1 (10 mmol), 0.11 g of Pd(OAc)$_2$ (0.5 mmol), 0.15 g of (p-toly)$_3$P (0.5 mmol), and 1.01 g of Et$_3$N (10 mmol) in 50 mL of dimethyl acetamide (DMAc), the reaction solution was stirred at a temperature of about 85° C. for about 4 hours. The reaction solution was cooled to room temperature, and then extracted three times with 100 mL of water and 100 mL of ethyl ether. The organic layer obtained therefrom was dried with magnesium sulfate, the solvent was evaporated, and the residue was separation-purified by silica gel column chromatography to obtain 3.53 g of Compound 1 (Yield: 66%). The obtained compound was identified by MS/FAB and $^1$H NMR.

Synthesis Example 2

Synthesis of Compound 13

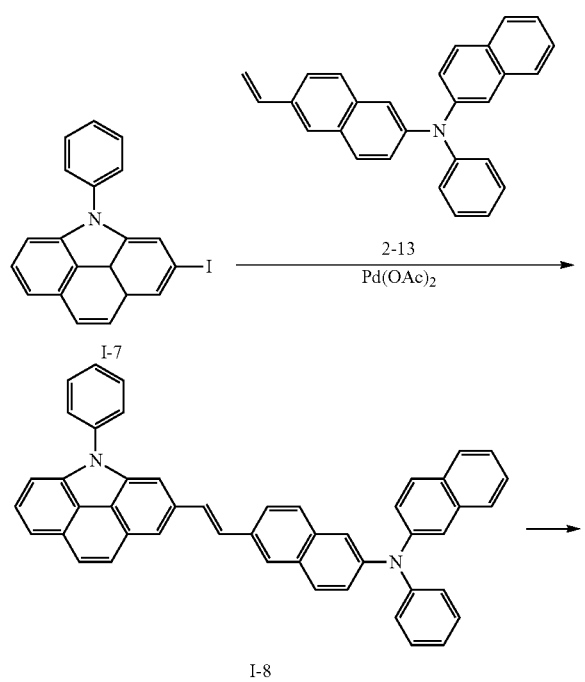

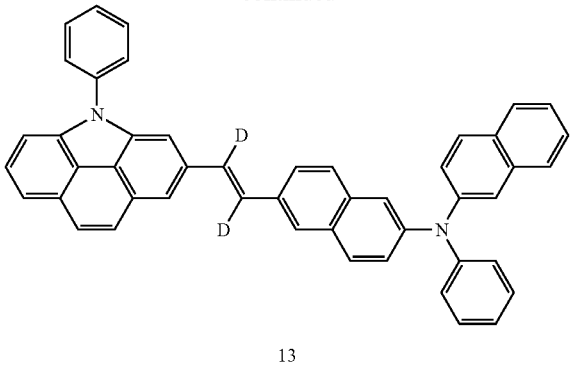

Synthesis of Intermediate I-8

3.89 g (Yield: 61%) of Intermediate I-8 was synthesized in the same manner as the synthesis of Compound 1 using Intermediate I-7 and Intermediate 2-13 (N-(naphthalene-2-yl)-N-phenyl-6-vinylnaphthalene-2-amine). The obtained compound was identified by LC-MS (C$_{48}$H$_{32}$N$_2$ M+ 637.3).

Synthesis of Compound 13

After dissolving 0.76 g (1.2 mmol) of Intermediate I-8, 0.081 g (0.08 mmol) of [(Ph$_3$)P]$_3$Ru(CO)(Cl)H (carbonyl-chloroxo-hydrido-tris (triphenylphosphine) ruthenium (II)), and 0.56 g (28.0 mmol) of D$_2$O in 30 mL of 1,4-dioxane, the reaction solution was stirred at a temperature of about 80 t for about 12 hours. The reaction solution was cooled to room temperature, and then extracted three times with 50 mL of water and 50 mL of dichloromethane. The organic layer obtained therefrom was dried with magnesium sulfate, the solvent was evaporated, and the residue was separation-purified by silica gel column chromatography to obtain 0.71 g of Compound 13 (Yield: 94%). The obtained compound was identified by MS/FAB and $^1$H NMR.

Synthesis Example 3

Synthesis of Compound 21

4.69 g of Compound 21 (Yield: 60%) was synthesized in the same manner as the synthesis of Compound 1 using Intermediate I-7 and Intermediate 2-21. The obtained compound was identified by MS/FAB and $^1$H NMR.

Synthesis Example 4

Synthesis of Compound 25

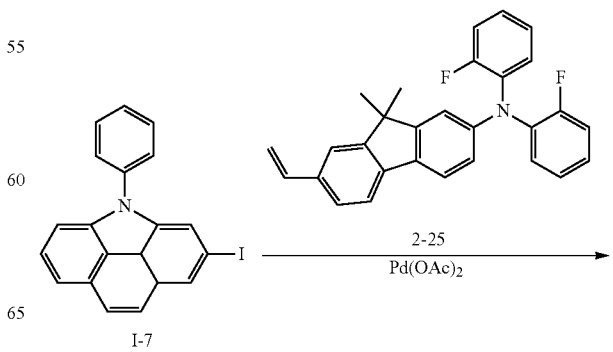

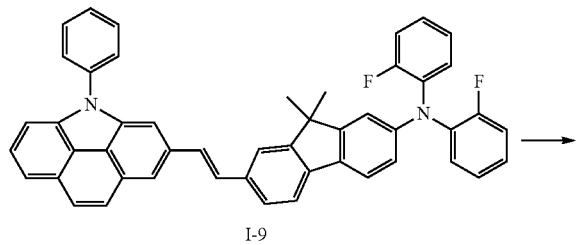

I-9

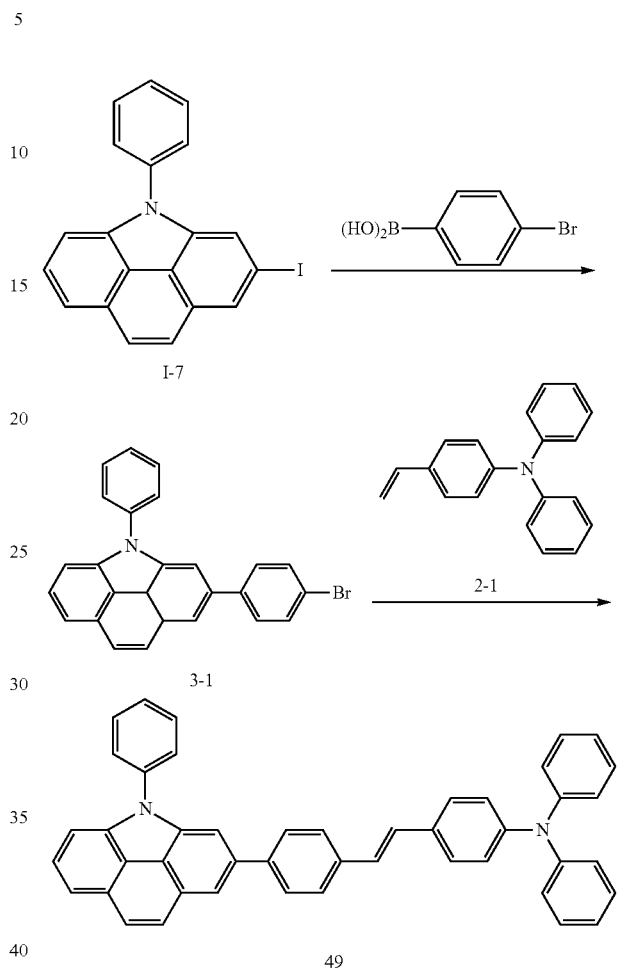

Synthesis of Intermediate I-9

4.54 g (Yield: 66%) of Intermediate I-9 was synthesized in the same manner as the synthesis Compound 1 using Intermediate I-7 and Intermediate 2-25. The obtained compound was identified by LC-MS ($C_{49}H_{34}F_2N_2$ M+ 687.3).

Synthesis of Compound 25

0.75 g (Yield: 90%) of Compound 25 was synthesized in the same manner as the synthesis of Compound 13 using Intermediate I-9. The obtained compound was identified by MS/FAB and $^1$H NMR.

Synthesis Example 5

Synthesis of Compound 35

6.01 g (Yield: 70%) of Compound 35 was synthesized in the same manner as the synthesis of Compound 1 using Intermediate I-7 and Intermediate 2-35. The obtained compound was identified by MS/FAB and $^1$H NMR.

Synthesis Example 6

Synthesis of Compound 41

5.48 g of (Yield: 68%) of Compound 41 was synthesized in the same manner as the synthesis of Compound 1 using Intermediate I-7 and Intermediate 2-41. The obtained compound was identified by MS/FAB and $^1$H NMR.

Synthesis Example 7

Synthesis of Compound 49

Synthesis of Intermediate 3-1

3.18 g (Yield: 75%) of Intermediate 3-1 was synthesized in the same manner as the synthesis of Intermediate 2-1 using Intermediate I-7 and 4-bromophenyl-boronic acid. The obtained compound was identified by LC-MS ($C_{26}H_{18}BrN$ M+ 424.1).

Synthesis of Compound 49

3.98 g (Yield: 65%) of Compound 49 was synthesized in the same manner as the synthesis of Compound 1 using Intermediate 2-1 and Intermediate 3-1. The obtained compound was identified by MS/FAB and $^1$H NMR.

Synthesis Example 8

Synthesis of Compound 52

6.14 g (Yield: 72%) of Compound 52 was synthesized in the same manner as the synthesis of Compound 49 using Intermediate 3-1 and Intermediate 2-52. The obtained compound was identified by MS/FAB and $^1$H NMR.

Synthesis Example 9

Synthesis of Compound 57

5.15 g (Yield: 67%) of Compound 57 was synthesized in the same manner as the synthesis of Compound 49 using Intermediate 3-2 and Intermediate 2-57. The obtained compound was identified by MS/FAB and $^1$H NMR.

Synthesis Example 10

Synthesis of Compound 61

5.46 g (Yield: 75%) of Compound 61 was synthesized in the same manner as the synthesis of Compound 49 using Intermediate 3-3 and Intermediate 2-1. The obtained compound was identified by MS/FAB and $^1$H NMR.

Synthesis Example 11

Synthesis of Compound 67

5.48 g (Yield: 77%) of Compound 67 was synthesized in the same manner as the synthesis of Compound 49 using Intermediate 3-4 and Intermediate 2-67. The obtained compound was identified by MS/FAB and $^1$H NMR.

Synthesis Example 12

Synthesis of Compound 71

4.20 g (Yield: 63%) of Compound 71 was synthesized in the same manner as the synthesis of Compound 49 using Intermediate 3-5 and Intermediate 2-71. The obtained compound was identified by MS/FAB and $^1$H NMR.

Synthesis Example 13

Synthesis of Compound 73

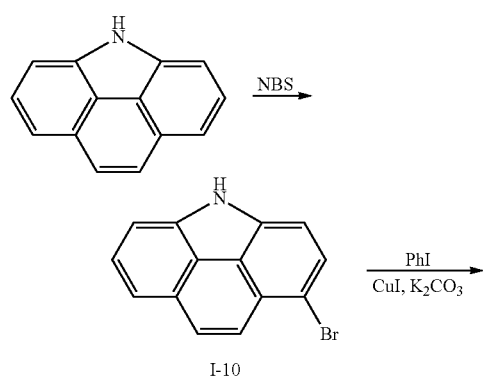

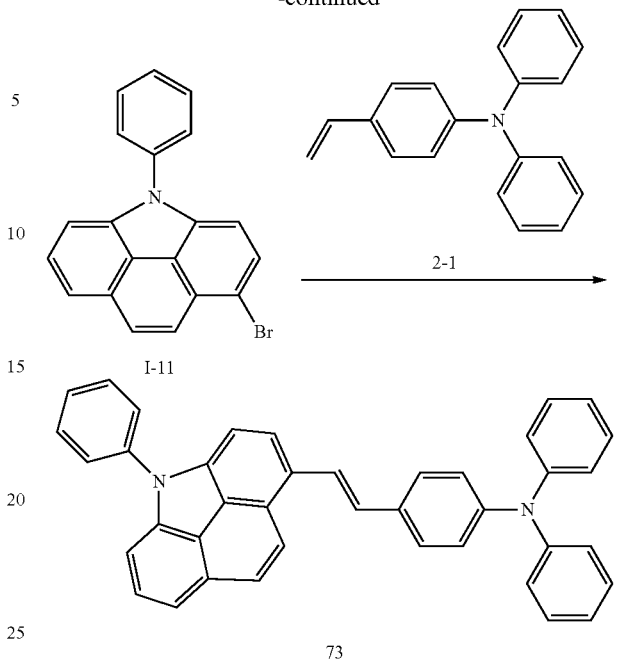

Synthesis of Intermediate I-10

After completely dissolving 1.91 g (10.0 mmol) of 6H-benzo[def]carbazole in 60 mL of carbon tetrachloride (CCl$_4$), 1.78 g (10.0 mmol) of N-bromosuccinimide was added thereto, and the reaction solution was stirred at a temperature of about 80° C. for about 30 minutes. The reaction solution was cooled to room temperature, and then stirred for about 30 minutes to precipitate crystals. The crystals obtained by a vacuum filter were washed with methanol to obtain 1.22 g (Yield: 45%) of Intermediate I-10 which was white in color. The obtained compound was identified by LC-MS (C$_{14}$H$_8$BrN M$^+$ 269.9).

Synthesis of Intermediate I-11

Intermediate I-11 was synthesized in the same manner as the synthesis of Intermediate I-5, except Intermediate I-10 was used instead of Intermediate I-4. The obtained compound was identified by LC-MS (C$_{20}$H$_{12}$BrN M$^+$ 346.0).

Synthesis of Compound 73

3.86 g (Yield: 72%) of Compound 73 was synthesized in the same manner as the synthesis of Compound 1 using Intermediate 2-1 and Intermediate I-11. The obtained compound was identified by MS/FAB and $^1$H NMR.

Synthesis Example 14

Synthesis of Compound 75

4.83 g (Yield: 74%) of Compound 75 was synthesized in the same manner as the synthesis of Compound 73 using Intermediate I-11 and Intermediate 2-75. The obtained compound was identified by MS/FAB and $^1$H NMR.

Synthesis Example 15

Synthesis of Compound 84

4.34 g (Yield: 69%) of Compound 84 was synthesized in the same manner as the synthesis of Compound 73 using Intermediate I-11 and Intermediate 2-84. The obtained compound was identified by MS/FAB and $^1$H NMR.

Synthesis Example 16

Synthesis of Compound 85

0.69 g (Yield: 91%) of Compound 85 was synthesized in the same manner as the synthesis of Compound 13 using Intermediate I-11 and Intermediate 2-13. The obtained compound was identified by MS/FAB and $^1$H NMR.

Synthesis Example 17

Synthesis of Compound 90

5.48 g (Yield: 73%) of Compound 90 was synthesized in the same manner as the synthesis of Compound 73 using Intermediate I-11 and Intermediate 2-90. The obtained compound was identified by MS/FAB and $^1$H NMR.

Synthesis Example 18

Synthesis of Compound 92

5.29 g (Yield: 70%) of Compound 92 was synthesized in the same manner as the synthesis of Compound 73 using Intermediate I-11 and Intermediate 2-21. The obtained compound was identified by MS/FAB and $^1$H NMR.

Synthesis Example 19

Synthesis of Compound 93

5.09 g (Yield: 78%) of Compound 93 was synthesized in the same manner as the synthesis of Compound 73 using Intermediate I-11 and Intermediate 2-93. The obtained compound was identified by MS/FAB and $^1$H NMR.

Synthesis Example 20

Synthesis of Compound 103

5.26 g (Yield: 66%) of Compound 103 was synthesized in the same manner as the synthesis of Compound 73 using Intermediate I-11 and Intermediate 2-103. The obtained compound was identified by MS/FAB and $^1$H NMR.

Synthesis Example 21

Synthesis of Compound 104

0.68 g (Yield: 88%) of Compound 104 was synthesized in the same manner as the synthesis of Compound 85 using Intermediate I-11 and Intermediate 2-104. The obtained compound was identified by MS/FAB and $^1$H NMR.

Synthesis Example 22

Synthesis of Compound 110

4.77 g (Yield: 75%) of Compound 110 was synthesized in the same manner as the synthesis of Compound 73 using Intermediate I-11 and Intermediate 2-110. The obtained compound was identified by MS/FAB and $^1$H NMR.

Synthesis Example 23

Synthesis of Compound 115

4.84 g (Yield: 79%) of Compound 115 was synthesized in the same manner as the synthesis of Compound 73 using Intermediate 3-6 and Intermediate 2-1. The obtained compound was identified by MS/FAB and $^1$H NMR.

Synthesis Example 24

Synthesis of Compound 118

6.05 g (Yield: 71%) of Compound 118 was synthesized in the same manner as the synthesis of Compound 73 using Intermediate 3-6 and Intermediate 2-52. The obtained compound was identified by MS/FAB and $^1$H NMR.

Synthesis Example 25

Synthesis of Compound 122

4.95 g (Yield: 68%) of Compound 122 was synthesized in the same manner as the synthesis of Compound 73 using Intermediate 3-6 and Intermediate 2-93. The obtained compound was identified by MS/FAB and $^1$H NMR.

Synthesis Example 26

Synthesis of Compound 124

5.37 g (Yield: 66%) of Compound 124 was synthesized in the same manner as the synthesis of Compound 73 using Intermediate 3-7 and Intermediate 2-1. The obtained compound was identified by MS/FAB and $^1$H NMR.

Synthesis Example 27

Synthesis of Compound 129

4.59 g (Yield: 63%) of Compound 129 was synthesized in the same manner as the synthesis of Compound 73 using Intermediate 3-8 and Intermediate 2-1. The obtained compound was identified by MS/FAB and $^1$H NMR.

Synthesis Example 28

Synthesis of Compound 133

5.83 g (Yield: 70%) of Compound 133 was synthesized in the same manner as the synthesis of Compound 73 using Intermediate 3-6 and Intermediate 2-133. The obtained compound was identified by MS/FAB and $^1$H NMR.

Synthesis Example 29

Synthesis of Compound 135

4.15 g (Yield: 60%) of Compound 135 was synthesized in the same manner as the synthesis of Compound 73 using Intermediate 3-9 and Intermediate 2-135. The obtained compound was identified by MS/FAB and $^1$H NMR.

Synthesis Example 30
Synthesis of Compound 136
0.83 g (Yield: 89%) of Compound 136 was synthesized in the same manner as the synthesis of Compound 85 using Intermediate 3-10 and Intermediate 2-104. The obtained compound was identified by MS/FAB and $^1$H NMR.
Intermediates
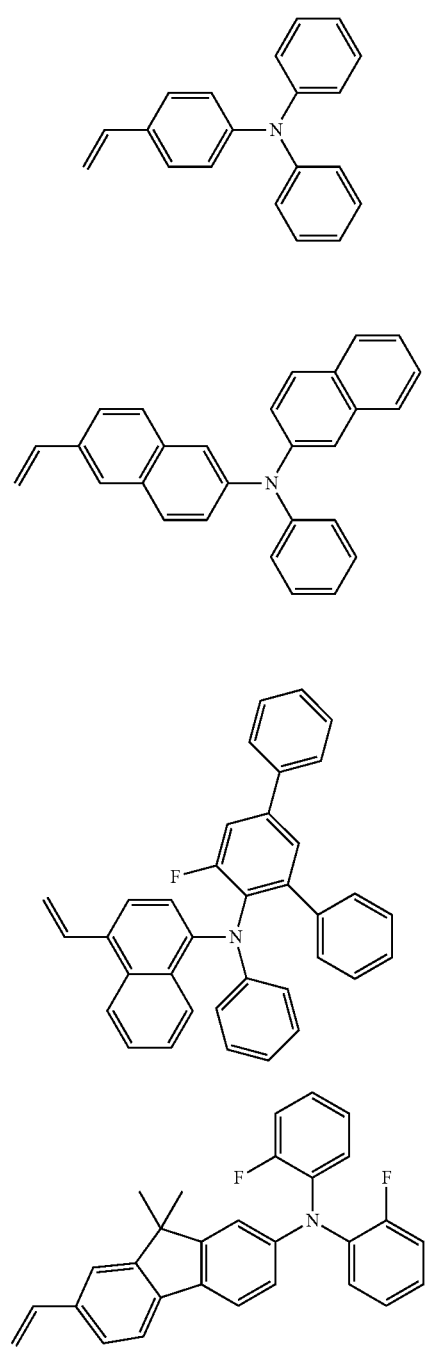
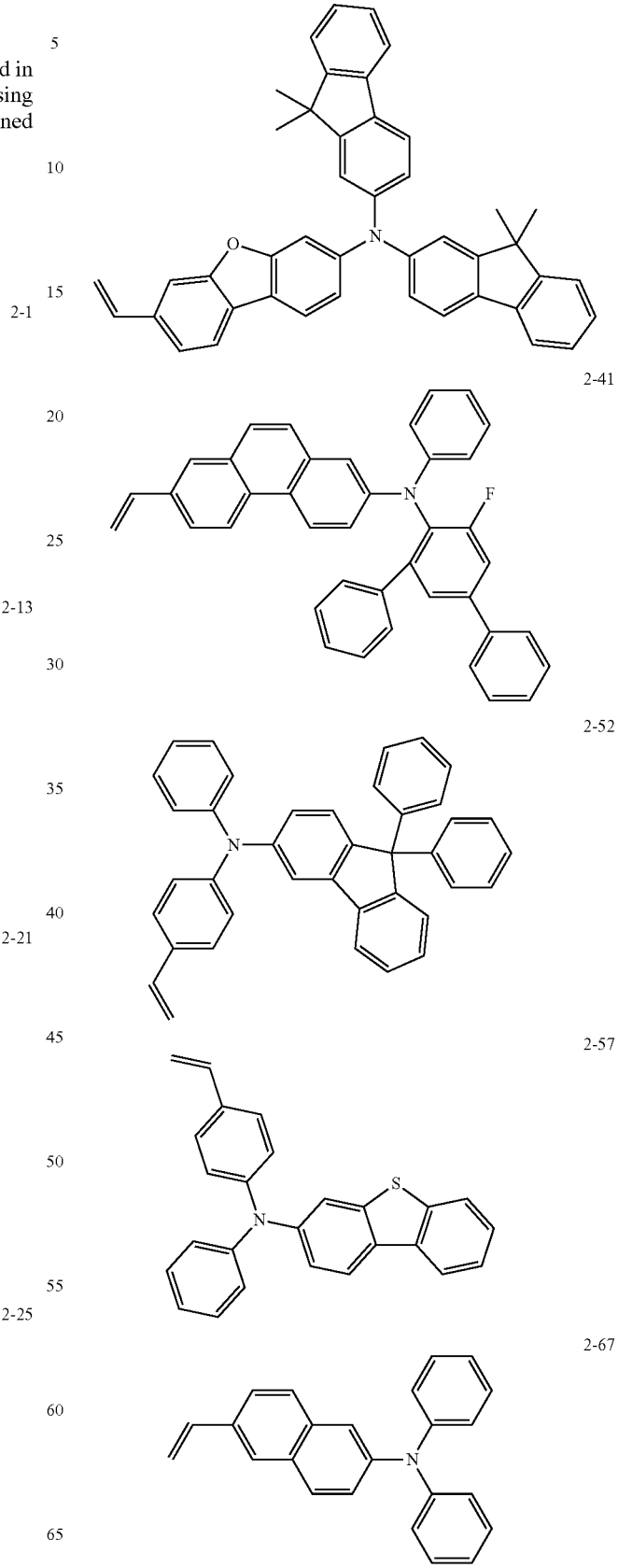

-continued
2-71
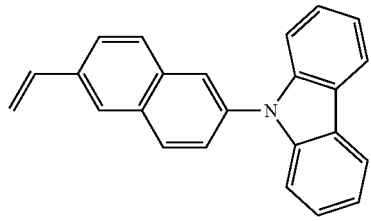
2-75
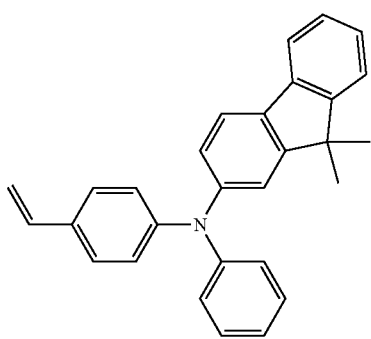
2-84
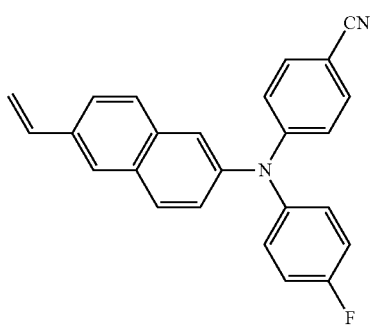
2-90
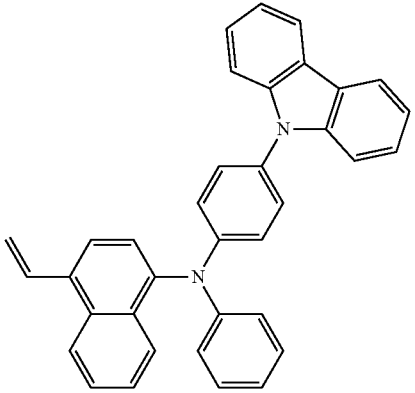
2-93
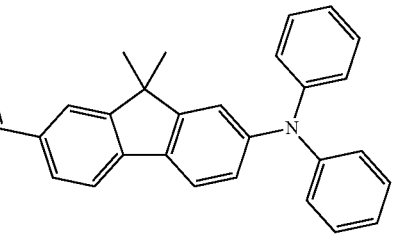
-continued
2-103
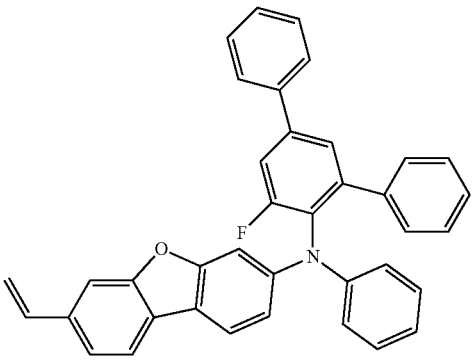
2-104
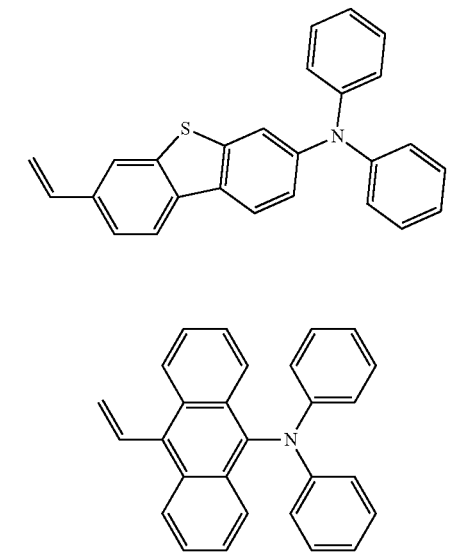
2-110
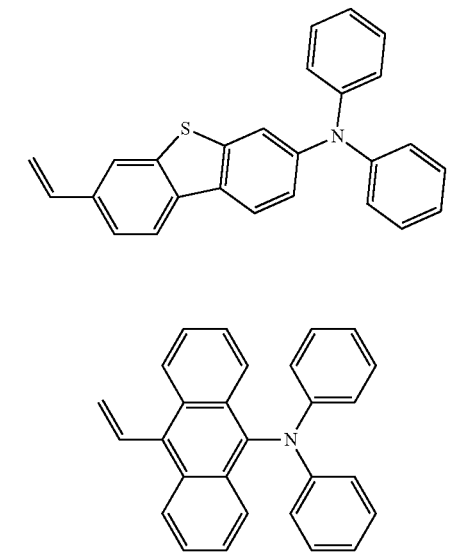
2-133
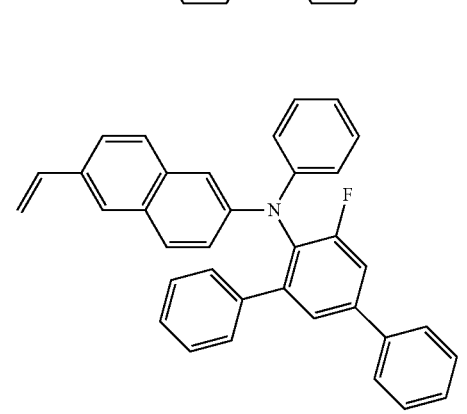
2-135
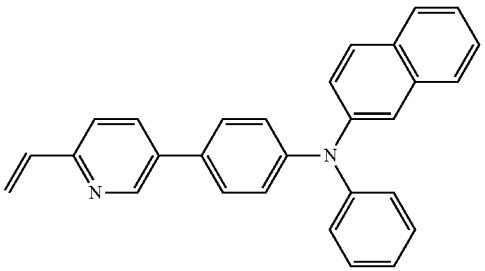

-continued
3-1
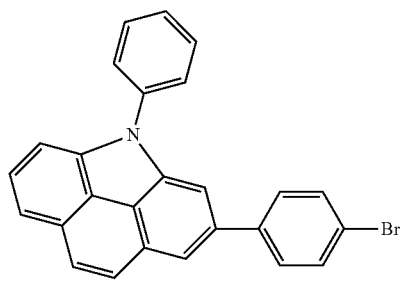
3-2
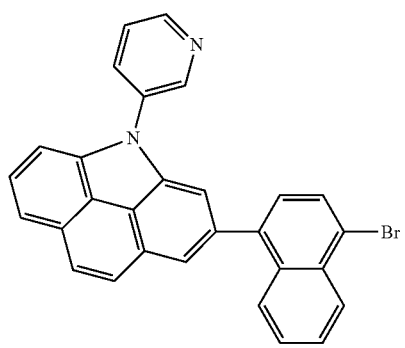
3-3
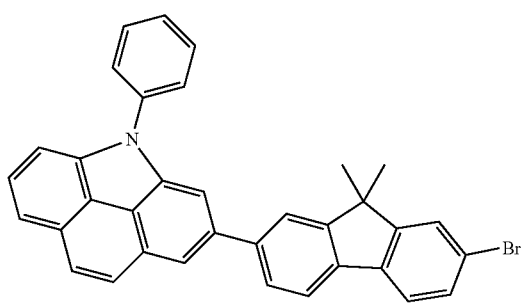
3-4
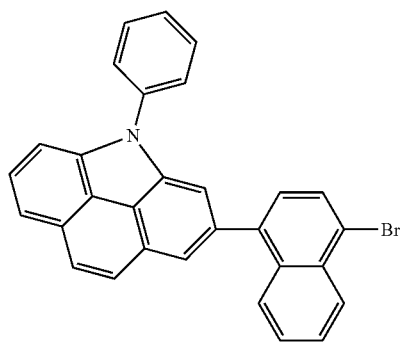
3-5
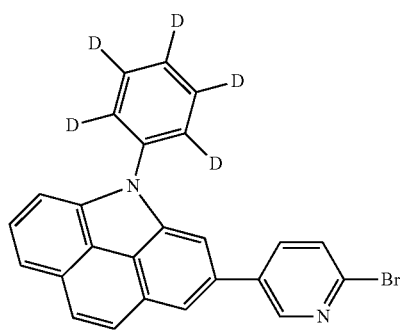
-continued
3-6
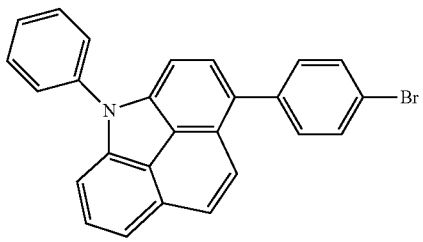
3-7
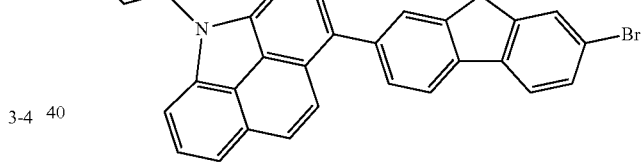
3-8
3-9
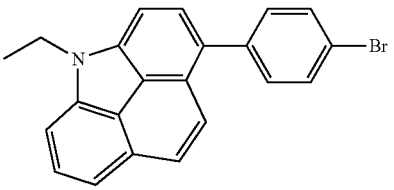
3-10
The results of ¹H NMR and MS/FAB of the synthesized compounds are shown in Table 1 below.

TABLE 1

| Comp. | ¹H NMR (CDCl₃, 400 MHz) | MS/FAB found | MS/FAB calc. |
|---|---|---|---|
| 1 | δ = 7.77-7.76 (m, 1H), 7.66 (s, 1H), 7.62-7.61 (m, 1H), 7.57-7.42 (m, 10H), 7.38-7.36 (m, 2H), 7.31-7.27 (ss, 1H), 7.08-7.03 (m, 4H), 6.70-6.62 (m, 4H), 6.16-6.13 (m, 4H) | 537.23 | 536.23 |
| 13 | δ = 7.91 (m, 1H), 7.78-7.64 (m, 8H), 7.57-7.36 (m, 13H), 7.28 (d, 1H), 7.14 (dd, 1H), 7.09-7.05 (m, 2H), 6.98-6.95 (m, 1H), 6.67-6.62 (m, 1H), 6.24-6.20 (m, 2H) | 639.27 | 638.27 |
| 21 | δ = 7.77-7.69 (m, 4H), 7.65-7.61 (m, 5H), 7.59-7.49 (m, 12H), 7.42-7.34 (m, 5H), 7.32 (s, 1H), 7.28-7.24 (m, 2H), 7.06-7.02 (m, 3H), 6.96-6.92 (m, 1H), 6.46-6.44 (ss, 1H), 6.05-6.01 (m, 2H) | 757.29 | 756.29 |
| 25 | δ = 7.78-7.75 (m, 1H), 7.68 (s, 1H), 7.66-7.64 (m, 2H), 7.62 (s, 1H), 7.58-7.42 (m, 8H), 7.40-7.35 (m, 2H), 7.28 (d, 1H), 7.15-7.07 (m, 2H), 7.01-6.93 (m, 4H), 6.69-6.66 (m, 2H), 6.61-6.59 (dd, 1H), 6.47-6.46 (d, 1H), 1.61 (s, 6H) | 691.28 | 690.28 |
| 35 | δ = 8.05-8.04 (m, 1H), 8.00-7.98 (m, 1H), 7.78-7.76 (m, 3H), 7.62 (m, 1H), 7.61 (ss, 2H), 7.55-7.53 (m, 3H), 7.51-7.45 (m, 5H), 7.42-7.28 (m, 8H), 7.14-7.08 (m, 4H), 7.00-6.95 (m, 2H), 6.90-6.89 (d, 1H), 6.88-6.87 (d, 1H), 6.53 (d, 2H), 1.61 (s, 12H) | 859.36 | 858.36 |
| 41 | δ = 8.48-8.46 (m, 1H), 8.05-8.03 (ss, 1H), 7.97 (m, 1H), 7.77-7.36 (m, 27H), 7.28 (d, 2H), 7.14-7.13 (d, 1H), 7.10 (d, 1H), 7.06-7.04 (m, 1H), 6.77-6.74 (m, 1H), 6.63-6.60 (m, 1H), 6.12-6.10 (m, 2H) | 807.31 | 806.31 |
| 49 | δ = 8.05 (d, 1H), 7.77-7.75 (m, 1H), 7.60-7.53 (m, 5H), 7.50-7.38 (m, 9H), 7.31-7.30 (m, 2H), 7.26 (s, 1H), 7.08-7.03 (m, 4H), 6.91-6.87 (ss, 1H), 6.70-6.63 (m, 4H), 6.16-6.13 (m, 4H) | 613.26 | 612.26 |
| 52 | δ = 8.06 (m, 1H), 7.85-7.84 (m, 1H), 7.77-7.75 (m, 1H), 7.60-7.53 (m, 6H), 7.51-7.45 (m, 8H), 7.40-7.38 (m, 2H), 7.31 (m, 2H), 7.26 (s, 1H), 7.18-7.04 (m, 13H), 6.87-6.79 (m, 4H), 6.66-6.63 (m, 1H), 6.46-6.43 (dd, 2H), 6.31-6.29 (m, 2H) | 853.35 | 852.35 |
| 57 | δ = 8.93-8.91 (m, 1H), 8.61 (m, 1H), 8.50-8.49 (m, 1H), 8.19-8.17 (ss, 1H), 8.13-8.11 (m, 2H), 7.91-7.81 (m, 4H), 7.77-7.75 (m, 1H), 7.66-7.65 (ss, 2H), 7.57-7.54 (m, 2H), 7.48-7.33 (m, 10H), 7.20-7.16 (m, 1H), 7.10-7.04 (m, 4H), 6.97-6.95 (m, 2H), 6.66-6.63 (m, 1H), 6.39-6.37 (m, 2H) | 770.26 | 769.26 |
| 61 | δ = 8.03 (m, 1H), 7.81 (m, 1H), 7.77-7.75 (m, 1H), 7.74-7.71 (ss, 1H), 7.66-7.64 (m, 2H), 7.62-7.60 (dd, 1H), 7.57-7.53 (m, 3H), 7.47-7.35 (m, 9H), 7.32-7.30 (m, 1H), 7.24 (d, 1H), 7.08-7.03 (m, 5H), 6.70-6.62 (m, 4H), 6.16-6.13 (m, 4H), 1.60 (s, 6H) | 729.32 | 728.32 |
| 67 | δ = 8.93-8.91 (m, 1H), 8.15-8.13 (m, 2H), 8.03 (m, 1H), 7.86-7.84 (m, 1H), 7.77 (ss, 1H), 7.72-7.70 (ss, 2H), 7.66-7.62 (m, 3H), 7.57-7.53 (m, 3H), 7.50-7.38 (m, 7H), 7.32-7.30 (m, 1H), 7.21-7.18 (m, 2H), 7.08-7.04 (m, 4H), 6.98-6.94 (m, 2H), 6.66-6.63 (m, 2H), 6.19-6.16 (m, 4H) | 713.29 | 712.29 |
| 71 | δ = 9.00-8.99 (m, 1H), 8.19-8.15 (m, 2H), 8.12-8.10 (m, 2H), 8.05-8.01 (m, 2H), 7.95-7.93 (dd, 1H), 7.88-7.86 (m, 1H), 7.78-7.69 (m, 4H), 7.64-7.59 (m, 2H), 7.51-7.47 (t, 1H), 7.37-7.25 (m, 10H) | 667.28 | 666.28 |
| 73 | δ = 8.17-8.15 (dd, 1H), 7.81-7.80 (ss, 1H), 7.70-7.68 (ss, 1H), 7.55-7.35 (m, 12H), 7.20-7.16 (ss, 1H), 7.08-7.03 (m, 4H), 6.76-6.73 (m, 2H), 6.66-6.63 (m, 2H), 6.16-6.13 (m, 4H) | 537.23 | 536.23 |
| 75 | δ = 8.17-8.15 (m, 1H), 7.81-7.76 (m, 2H), 7.70-7.68 (ss, 1H), 7.62 (m, 1H), 7.58-7.30 (m, 13H), 7.20-7.16 (ss, 1H), 7.11-7.04 (m, 4H), 6.76-6.74 (m, 2H), 6.69-6.63 (m, 2H), 6.39-6.38 (d, 1H), 6.24-6.21 (m, 2H), 1.61 (s, 6H) | 653.29 | 652.29 |
| 84 | δ = 8.17-8.13 (m, 2H), 8.03-8.02 (m, 1H), 7.81-7.79 (m, 1H), 7.72-7.68 (t, 3H), 7.63-7.60 (m, 2H), 7.55-7.47 (m, 7H), 7.45-7.43 (m, 2H), 7.40-7.35 (m, 3H), 6.97-6.89 (m, 3H), 6.82-6.78 (m, 2H), 6.55-6.50 (m, 2H) | 630.23 | 629.23 |
| 85 | δ = 8.17-8.15 (d, 1H), 7.89 (m, 1H), 7.82-7.64 (m, 8H), 7.57-7.35 (m, 13H), 7.14-7.05 (m, 3H), 6.98-6.95 (m, 1H), 6.67-6.63 (m, 1H), 6.24-6.20 (m, 2H) | 639.27 | 638.27 |
| 90 | δ = 8.20-8.18 (m, 1H), 8.12-8.10 (m, 2H), 7.89-7.86 (m, 1H), 7.66-7.60 (m, 1H), 7.55-7.44 (m, 12H), 7.38-7.26 (m, 7H), 7.22-7.14 (m, 2H), 7.06-7.01 (m, 4H), 6.94-6.91 (m, 1H), 6.83-6.79 (m, 2H), 6.65-6.61 (m, 1H), 6.13-6.11 (m, 2H) | 752.30 | 751.30 |
| 92 | δ = 8.20-8.18 (m, 1H), 7.81-7.79 (m, 1H), 7.75-7.36 (m, 26H), 7.21-7.19 (d, 1H), 7.06-7.01 (m, 3H), 6.96-6.92 (m, 1H), 6.62-6.58 (m, 2H), 6.04-6.01 (m, 2H) | 757.29 | 756.29 |
| 93 | δ = 8.17-8.15 (m, 1H), 7.81-7.79 (d, 1H), 7.75-7.73 (ss, 1H), 7.70-7.68 (ss, 1H), 7.66-7.64 (m, 2H), 7.55-7.36 (m, 11H), 7.24-7.20 (ss, 1H), 7.09-7.04 (m, 4H), 6.67-6.63 (m, 3H), 6.46-6.45 (d, 1H), 6.15-6.13 (m, 4H), 1.61 (s, 6H) | 653.29 | 652.29 |
| 103 | δ = 8.17-8.15 (dd, 1H), 8.05-8.03 (ss, 1H), 7.83-7.80 (m, 2H), 7.72-7.69 (m, 3H), 7.65-7.60 (m, 3H), 7.57-7.34 (m, 19H), 7.14-7.10 (dd, 3H), 7.07-7.01 (m, 3H), 6.81-6.79 (dd, 1H), 6.63-6.60 (m, 1H), 6.26-6.22 (m, 2H) | 797.29 | 796.29 |
| 104 | δ = 8.18-8.16 (m, 2H), 8.15 (s, 1H), 8.03-8.01 (d, 1H), 7.81-7.76 (m, 2H), 7.70-7.68 (ss, 1H), 7.61-7.59 (dd, 1H), 7.53-7.35 (m 9H), 7.12-7.04 (m, 5H), 6.94-6.91 (dd, 1H), 6.66-6.63 (m, 2H), 6.33-6.30 (m, 3H) | 645.23 | 644.23 |
| 110 | δ = 8.21-8.19 (dd, 1H), 7.91-7.89 (m, 2H), 7.82-7.80 (m, 1H), 7.72 (s, 2H), 7.62-7.36 (m, 12H), 7.04-6.98 (m, 6H), 6.88-6.84 (m, 2H), 6.63-6.60 (m, 2H), 5.97-5.94 (m, 4H) | 637.26 | 636.26 |
| 115 | δ = 7.77 (s, 1H), 7.75-7.72 (m, 3H), 7.60-7.35 (m, 13H), 7.32-7.30 (m, 1H), 7.13 (s, 1H), 7.09-7.03 (m, 4H), 6.91-6.87 (ss, 1H), 6.70-6.62 (m, 4H), 6.16-6.13 (m, 4H) | 613.26 | 612.26 |

TABLE 1-continued

| Comp. | $^1$H NMR (CDCl$_3$, 400 MHz) | MS/FAB found | MS/FAB calc. |
|---|---|---|---|
| 118 | δ = 7.85-7.84 (m, 1H), 7.77 (s, 1H), 7.75-7.72 (m, 3H), 7.60-7.44 (m, 14H), 7.40-7.36 (m, 1H), 7.32-7.30 (m, 1H), 7.18-7.16 (dd, 1H), 7.14-7.04 (m, 13H), 6.91 (s, 1H), 6.84-6.79 (m, 3H), 6.66-6.63 (m, 1H), 6.46-6.43 (dd, 1H), 6.38-6.36 (dd, 1H), 6.32-6.29 (m, 2H) | 853.35 | 852.35 |
| 122 | δ = 7.77 (s, 1H), 7.75-7.72 (m, 4H), 7.68-7.66 (ss, 1H), 7.64 (m, 1H), 7.60-7.46 (m, 9H), 7.44-7.30 (m, 4H), 7.09-7.04 (m, 6H), 6.67-6.62 (m, 3H), 6.46-6.45 (d, 1H), 6.16-6.13 (m, 4H), 1.61 (s, 6H) | 729.32 | 728.32 |
| 124 | δ = 8.08-8.05 (m, 1H), 8.00-7.98 (ss, 1H), 7.82-7.73 (m, 8H), 7.61-7.58 (ss, 1H), 7.54-7.32 (m, 16H), 7.08-7.04 (m, 6H), 7.00-6.96 (m, 1H), 6.76-6.73 (m, 2H), 6.66-6.62 (m, 2H), 6.16-6.13 (m, 4H) | 815.33 | 814.33 |
| 129 | δ = 7.95 (d, 1H), 7.92-7.86 (m, 2H), 7.75-7.73 (m, 1H), 7.66-7.60 (m, 3H), 7.55-7.30 (m, 14H), 7.08-7.03 (m, 5H), 6.70-6.63 (m, 4H), 6.16-6.13 (m, 4H), 1.64 (s, 6H) | 729.32 | 728.32 |
| 133 | δ = 8.08-8.05 (m, 1H), 7.95 (m, 1H), 7.77 (s, 1H), 7.75-7.38 (m, 27H), 7.32-7.29 (m, 3H), 7.19 (s, 1H), 7.14 (d, 1H), 7.10-7.03 (m, 3H), 6.63-6.60 (m, 1H), 6.12 (m, 2H) | 833.33 | 832.33 |
| 135 | δ = 8.89 (d, 1H), 8.09-8.07 (dd, 1H), 7.83 (t, 1H), 7.80-7.76 (m, 4H), 7.71-7.48 (m, 11H), 7.40-7.38 (m, 4H), 7.30-7.28 (m, 2H), 7.13-7.04 (m, 4H), 6.72-6.63 (m, 3H), 6.24-6.22 (m, 2H), 1.29 (s, 3H) | 692.30 | 691.30 |
| 136 | δ = 8.10-8.08 (m, 2H), 8.02-8.01 (m, 2H), 7.97-7.94 (m, 2H), 7.89-7.87 (m, 2H), 7.78-7.73 (m, 2H), 7.60 (s, 1H), 7.58-7.47 (m, 8H), 7.40-7.36 (m, 2H), 7.32-7.30 (dd, 1H), 7.12-7.04 (m, 5H), 6.94-6.91 (dd, 1H), 6.66-6.63 (m, 2H), 6.33-6.29 (m, 4H) | 771.27 | 770.27 |

Example 1

An anode was prepared by cutting a Corning 15Ω/cm$^2$ (1,200 Å) ITO glass substrate to a size of 50 mm×50 mm×0.7 mm, sonicating the cut substrate in isopropyl alcohol for about 5 minutes and in pure water for about 5 minutes, and then cleaning the substrate by irradiation of ultraviolet rays for about 30 minutes, and exposing the substrate to ozone.

2-TNATA was vacuum deposited on the anode to a thickness of about 600 Å to form an HIL, and 4'-bis[N-(1-naphthyl)-N-phenylamino]biphenyl (hereinafter, NPB) as a hole transporting compound was vacuum-deposited on the HIL to a thickness of about 300 Å.

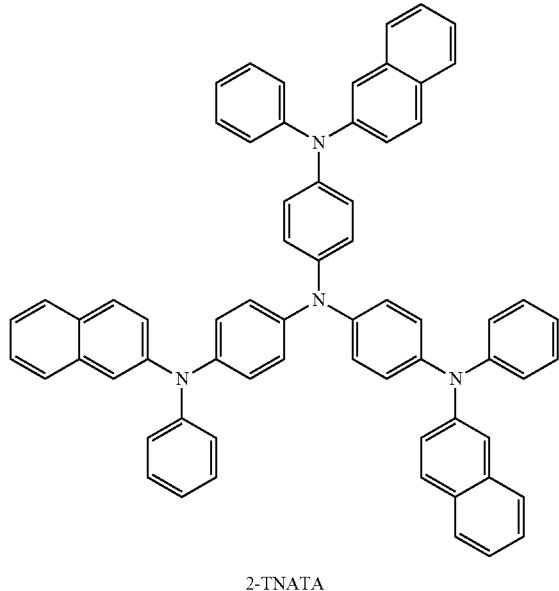

2-TNATA

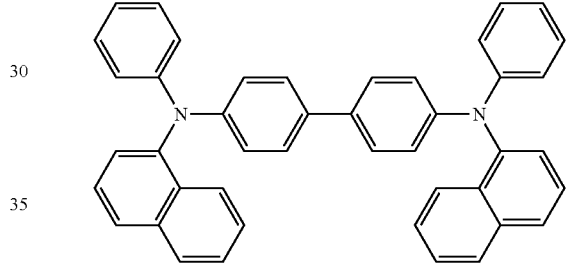

NPB

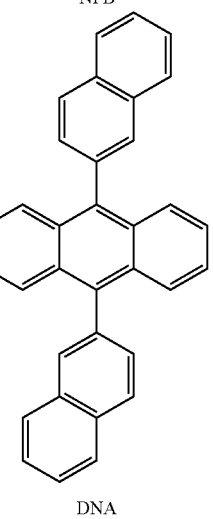

DNA 9,10-di-naphthalene-2-yl-anthracene (hereinafter, DNA) as a blue fluorescent host, and Compound 1 as a blue fluorescent dopant, were co-deposited at a weight ratio of about 98:2 on the HTL to form an EML having a thickness of 300 Å.

Next, Alq$_3$ was deposited on the EML to form an ETL having a thickness of about 300 Å, and then LiF, which is a halogenated alkali metal, was deposited on the ETL to form an EIL having a thickness of about 10 Å. Then, Al was vacuum-deposited on the EIL to form a cathode having a thickness of about 3,000 Å, thereby forming a LiF/Al electrode and completing the manufacture of an OLED.

The OLED had a driving voltage of about 6.43 V at a current density of 50 mA/cm$^2$, a luminosity of 2,280 cd/m$^2$, a luminescent efficiency of 4.56 cd/A, and a half life-span (hr @100 mA/cm$^2$) of about 217 hours.

Example 2

An OLED was manufactured as in Example 1, except that Compound 13 was used instead of Compound 1 to form the EML.

The OLED had a driving voltage of about 6.43 V at a current density of 50 mA/cm$^2$, a luminosity of 2,420 cd/m$^2$, a luminescent efficiency of 4.84 cd/A, and a half life-span (hr @100 mA/cm$^2$) of about 258 hours.

Example 3

An OLED was manufactured as in Example 1, except that Compound 25 was used instead of Compound 1 to form the EML.

The OLED had a driving voltage of about 6.58 V at a current density of 50 mA/cm$^2$, a luminosity of 2,705 cd/m$^2$, a luminescent efficiency of 5.41 cd/A, and a half life-span (hr @100 mA/cm$^2$) of about 236 hours.

Example 4

An OLED was manufactured as in Example 1, except that Compound 41 was used instead of Compound 1 to form the EML.

The OLED had a driving voltage of about 6.45 V at a current density of 50 mA/cm$^2$, a luminosity of 2,675 cd/m$^2$, a luminescent efficiency of 5.35 cd/A, and a half life-span (hr @100 mA/cm$^2$) of about 277 hours.

Example 5

An OLED was manufactured as in Example 1, except that Compound 49 was used instead of Compound 1 to form the EML.

The OLED had a driving voltage of about 6.05 V at a current density of 50 mA/cm$^2$, a luminosity of 2,885 cd/m$^2$, a luminescent efficiency of 5.77 cd/A, and a half life-span (hr @100 mA/cm$^2$) of about 296 hours.

Example 6

An OLED was manufactured as in Example 1, except that Compound 61 was used instead of Compound 1 to form the EML.

The OLED had a driving voltage of about 6.24 V at a current density of 50 mA/cm$^2$, a luminosity of 2,765 cd/m$^2$, a luminescent efficiency of 5.53 cd/A, and a half life-span (hr @100 mA/cm$^2$) of about 262 hours.

Example 7

An OLED was manufactured as in Example 1, except that Compound 71 was used instead of Compound 1 to form the EML.

The OLED had a driving voltage of about 6.61 V at a current density of 50 mA/cm$^2$, a luminosity of 2,530 cd/m$^2$, a luminescent efficiency of 5.06 cd/A, and a half life-span (hr @100 mA/cm$^2$) of about 243 hours.

Example 8

An OLED was manufactured as in Example 1, except that Compound 73 was used instead of Compound 1 to form the EML.

The OLED had a driving voltage of about 6.31 V at a current density of 50 mA/cm$^2$, a luminosity of 2,470 cd/m$^2$, a luminescent efficiency of 4.94 cd/A, and a half life-span (hr @100 mA/cm$^2$) of about 225 hours.

Example 9

An OLED was manufactured as in Example 1, except that Compound 84 was used instead of Compound 1 to form the EML.

The OLED had a driving voltage of about 6.42 V at a current density of 50 mA/cm$^2$, a luminosity of 2,555 cd/m$^2$, a luminescent efficiency of 5.11 cd/A, and a half life-span (hr @100 mA/cm$^2$) of about 242 hours.

Example 10

An OLED was manufactured as in Example 1, except that Compound 92 was used instead of Compound 1 to form the EML.

The OLED had a driving voltage of about 6.34 V at a current density of 50 mA/cm$^2$, a luminosity of 2,715 cd/m$^2$, a luminescent efficiency of 5.43 cd/A, and a half life-span (hr @100 mA/cm$^2$) of about 279 hours.

Example 11

An OLED was manufactured as in Example 1, except that Compound 104 was used instead of Compound 1 to form the EML.

The OLED had a driving voltage of about 6.47 V at a current density of 50 mA/cm$^2$, a luminosity of 2,525 cd/m$^2$, a luminescent efficiency of 5.05 cd/A, and a half life-span (hr @100 mA/cm$^2$) of about 257 hours.

Example 12

An OLED was manufactured as in Example 1, except that Compound 115 was used instead of Compound 1 to form the EML.

The OLED had a driving voltage of about 6.08 V at a current density of 50 mA/cm$^2$, a luminosity of 2,930 cd/m$^2$, a luminescent efficiency of 5.86 cd/A, and a half life-span (hr @100 mA/cm$^2$) of about 294 hours.

Example 13

An OLED was manufactured as in Example 1, except that Compound 122 was used instead of Compound 1 to form the EML.

The OLED had a driving voltage of about 6.26 V at a current density of 50 mA/cm$^2$, a luminosity of 2,860 cd/m$^2$, a luminescent efficiency of 5.72 cd/A, and a half life-span (hr @100 mA/cm$^2$) of about 277 hours.

Example 14

An OLED was manufactured as in Example 1, except that Compound 135 was used instead of Compound 1 to form the EML.

The OLED had a driving voltage of about 6.41 V at a current density of 50 mA/cm$^2$, a luminosity of 2,605 cd/m$^2$, a luminescent efficiency of 5.21 cd/A, and a half life-span (hr @100 mA/cm$^2$) of about 233 hours.

Comparative Example 1

An OLED was manufactured as in Example 1, except that the blue fluorescent dopant 4,4'-bis[2-(4-(N,N-diphenylamino)phenyl)vinyl]biphenyl (hereinafter, referred as DPAVBi) was used instead of Compound 1 to form the EML.

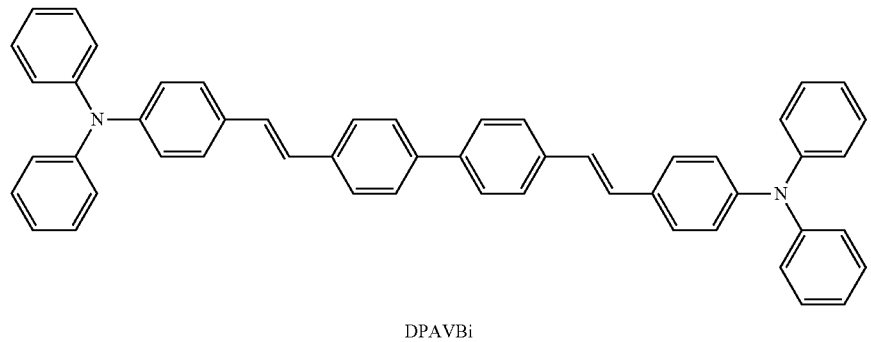 [SMILES: C(=C\c1ccc(N(c2ccccc2)c2ccccc2)cc1)/c1ccc(-c2ccc(/C=C/c3ccc(N(c4ccccc4)c4ccccc4)cc3)cc2)cc1]

DPAVBi

The OLED had a driving voltage of about 7.35 V at a current density of 50 mA/cm$^2$, a luminosity of 2,065 cd/m$^2$, a luminescent efficiency of 4.13 cd/A, and a half life-span (hr @100 mA/cm$^2$) of about 145 hours.

Compounds of Formula 1, according to embodiments of the present invention, were used as a blue dopant in the EML of the OLEDs of Examples 1-14. Compared to the OLED using the blue fluorescent dopant DPVBi (i.e., Comparative Example 1), the OLEDs including the compounds of Formula 1 showed improved driving voltage and I-V-L characteristics as well as improved efficiency, and lifetime. The representative characteristics and lifetimes of the OLEDs of Examples 1-14 are summarized in Table 2 below.

TABLE 2

| | Light-emitting material | Driving voltage (V) | Current density (mA/cm2) | Brightness (cd/m2) | Efficiency (cd/A) | Luminescence color | Half-life lifetime (hr @100 mA/cm$^2$) |
|---|---|---|---|---|---|---|---|
| Example 1 | Compound 1 | 6.43 | 50 | 2,280 | 4.56 | Blue | 217 hr |
| Example 2 | Compound 13 | 6.34 | 50 | 2,420 | 4.84 | Blue | 258 hr |
| Example 3 | Compound 25 | 6.58 | 50 | 2,705 | 5.41 | Blue | 236 hr |
| Example 4 | Compound 41 | 6.45 | 50 | 2,675 | 5.35 | Blue | 277 hr |
| Example 5 | Compound 49 | 6.05 | 50 | 2,885 | 5.77 | Blue | 296 hr |
| Example 6 | Compound 61 | 6.24 | 50 | 2,765 | 5.53 | Blue | 262 hr |
| Example 7 | Compound 71 | 6.61 | 50 | 2,530 | 5.06 | Blue | 243 hr |
| Example 8 | Compound 73 | 6.31 | 50 | 2,470 | 4.94 | Blue | 225 hr |
| Example 9 | Compound 84 | 6.42 | 50 | 2,555 | 5.11 | Blue | 242 hr |
| Example 10 | Compound 92 | 6.34 | 50 | 2,715 | 5.43 | Blue | 279 hr |
| Example 11 | Compound 104 | 6.47 | 50 | 2,525 | 5.05 | Blue | 257 hr |
| Example 12 | Compound 115 | 6.08 | 50 | 2,930 | 5.86 | Blue | 294 hr |
| Example 13 | Compound 122 | 6.26 | 50 | 2,860 | 5.72 | Blue | 277 hr |
| Example 14 | Compound 135 | 6.41 | 50 | 2,605 | 5.21 | Blue | 233 hr |

As described above, a heterocyclic compound represented by Formula 1 has good light-emitting ability, and thus may be effectively used as a light-emitting material suitable for fluorescent and phosphorescent diodes emitting all colors, such as red green, blue, or white. Therefore, an organic electroluminescent device having high efficiency, low driving voltage, high luminance, and a long lifetime may be manufactured using the compound.

While the present invention has been illustrated and described with reference to certain exemplary embodiments, it will be understood by those of ordinary skill in the art that various changes may be made to the described embodiments without departing from the spirit and scope of the present invention as defined by the following claims.

What is claimed is:
1. A heterocyclic compound represented by Formula 1:

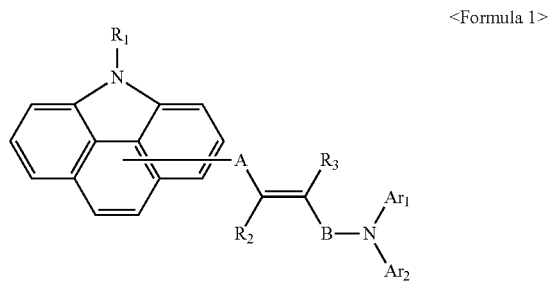

<Formula 1> wherein, in Formula 1,
A and B are each independently a single bond or a bivalent linker that is a substituted or unsubstituted $C_6$-$C_{30}$ arylene group, a substituted or unsubstituted $C_2$-$C_{30}$ heteroarylene group, or a substituted or unsubstituted $C_6$-$C_{30}$ condensed polycyclic group;

$R_1$, $R_2$, and $R_3$ are each independently a hydrogen atom, a deuterium atom, a substituted or unsubstituted $C_1$-$C_{60}$ alkyl group, a substituted or unsubstituted $C_3$-$C_{60}$ cycloalkyl group, a substituted or unsubstituted $C_6$-$C_{60}$ aryl group, a substituted or unsubstituted $C_2$-$C_{60}$ heteroaryl group, a substituted or unsubstituted $C_6$-$C_{30}$ condensed polycyclic group, a fluoro group, or a cyano group;

$Ar_1$ and $Ar_2$ are each independently a substituted or unsubstituted $C_6$-$C_{30}$ aryl group, a substituted or unsubstituted $C_2$-$C_{30}$ heteroaryl group, or a substituted or unsubstituted $C_6$-$C_{30}$ condensed polycyclic group; and $Ar_1$ and $Ar_2$ optionally combine with each other or adjacent substituents to form a ring.

2. The heterocyclic compound of claim 1, wherein the heterocyclic compound is represented by Formula 2:

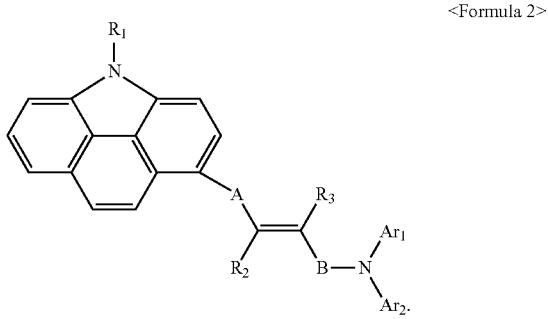

<Formula 2>

3. The heterocyclic compound of claim 1, wherein the heterocyclic compound is represented by Formula 3:

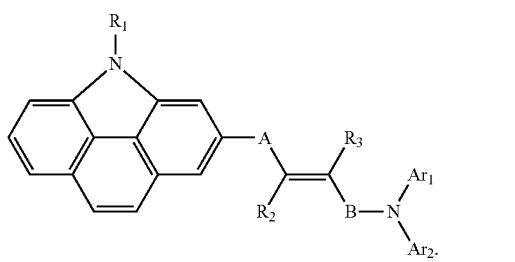

<Formula 3>

4. The heterocyclic compound of claim 1, wherein $Ar_1$ and $Ar_2$ combine with each other or adjacent substituents to form a ring.

5. The heterocyclic compound of claim 1, wherein $R_1$ is a substituted or unsubstituted $C_1$-$C_{30}$ alkyl group, or a group represented by Formula 2a or Formula 2b:

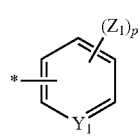

2a

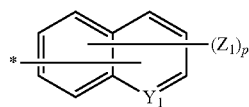

2b wherein, in Formulas 2a and 2b, $Z_1$ is a hydrogen atom, a deuterium atom, a halogen atom, —CN, a substituted or unsubstituted $C_1$-$C_{20}$ alkyl group, a substituted or unsubstituted $C_6$-$C_{20}$ aryl group, or a substituted or unsubstituted $C_2$-$C_{20}$ heteroaryl group;

$Y_1$ is CH or N;

p is an integer from 1 to 6; and

* is a binding site.

6. The heterocyclic compound of claim 1, wherein $R_2$ and $R_3$ are each independently a hydrogen atom, a deuterium atom, a substituted or unsubstituted $C_1$-$C_{30}$ alkyl group, or a group represented by Formula 3a:

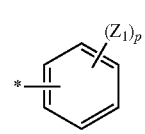

3a wherein, in Formula 3a, $Z_1$ is a hydrogen atom, a deuterium atom, a halogen atom, —CN, a substituted or unsubstituted $C_1$-$C_{20}$ alkyl group, a substituted or unsubstituted $C_6$-$C_{20}$ aryl group, or a substituted or unsubstituted $C_2$-$C_{20}$ heteroaryl group;

p is an integer from 1 to 5; and

* is a binding site.

7. The heterocyclic compound of claim 1, wherein $Ar_1$ and $Ar_2$ are each independently a group represented by one of Formulas 4a to 4d:

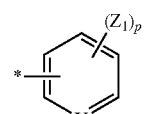

4a

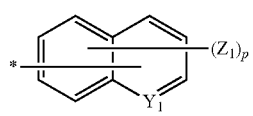

4b

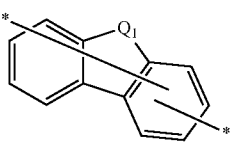

4c

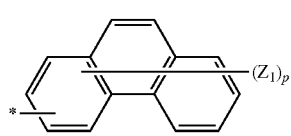

4d wherein, in Formulas 4a to 4d, $Z_1$ is a hydrogen atom a deuterium atom, a halogen atom, —CN, a substituted or unsubstituted $C_1$-$C_{20}$ alkyl group, a substituted or unsubstituted $C_6$-$C_{20}$ aryl group, or a substituted or unsubstituted $C_2$-$C_{20}$ heteroaryl group;

$Y_1$ is CH or N;

$Q_1$ is a linker represented by —C($R_{30}$)($R_{31}$)—, —S—, or —O—;

$R_{30}$ and $R_{31}$ are each independently a hydrogen atom, a deuterium atom, a substituted or unsubstituted $C_1$-$C_{20}$ alkyl group, a substituted or unsubstituted $C_6$-$C_{20}$ aryl group, or a substituted or unsubstituted $C_6$-$C_{20}$ condensed polycyclic group;

p is an integer from 1 to 9; and

* is a binding site.

8. The heterocyclic compound of claim 1, wherein A and B are each independently a single bond, a group represented by one of Formulas 5a to 5e, or a linker connecting at least two groups represented by Formulas 5a to 5e:

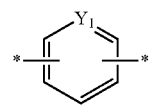
5a

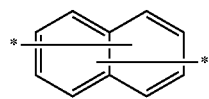
5b

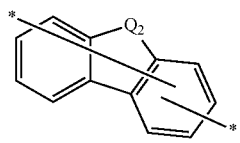
5c

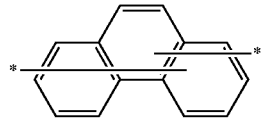
5d

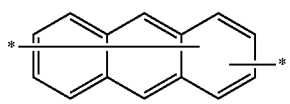
5e wherein, in Formulas 5a to 5e, $Y_1$ is CH or N;

$Q_2$ is a linker represented by —C($R_{30}$)($R_{31}$)—, —S—, or —O—;

$R_{30}$ and $R_{31}$ are each independently a hydrogen atom, a deuterium atom, a substituted or unsubstituted $C_1$-$C_{20}$ alkyl group, a substituted or unsubstituted $C_6$-$C_{20}$ aryl group, or a substituted or unsubstituted $C_6$-$C_{20}$ condensed polycyclic group; and

* is a binding site.

9. The heterocyclic compound of claim 1, wherein the compound of Formula 1 is one of Compounds 1 through 137:

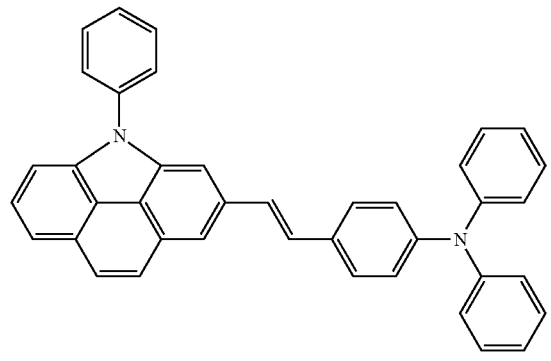
1

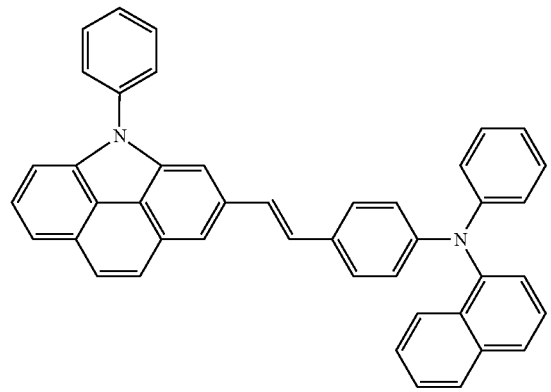
2

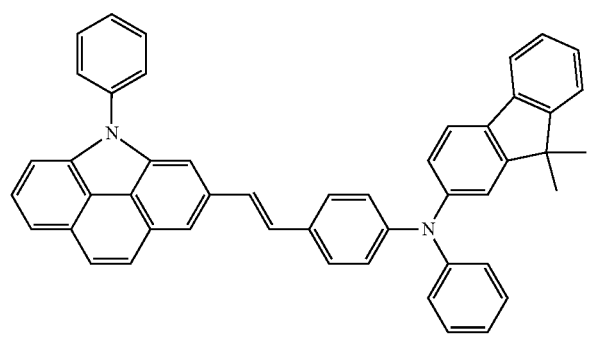
3

-continued
4
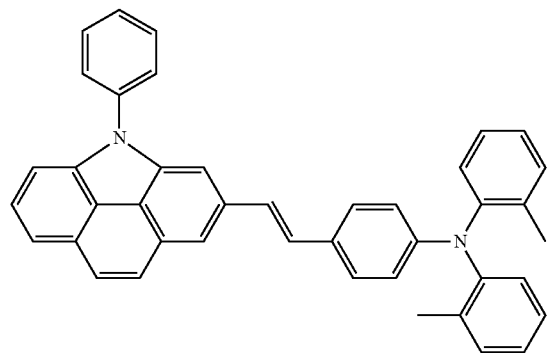
5
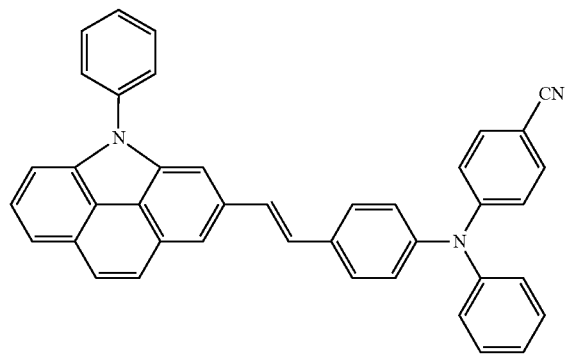
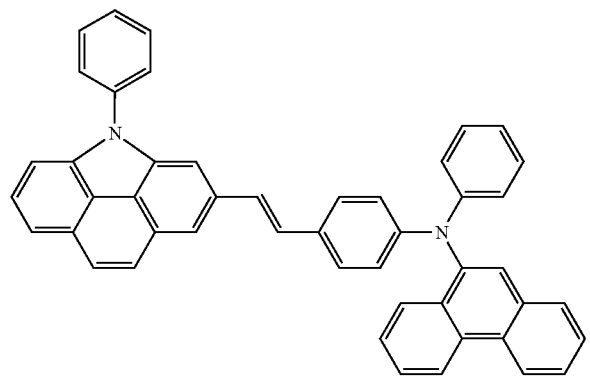
6
7
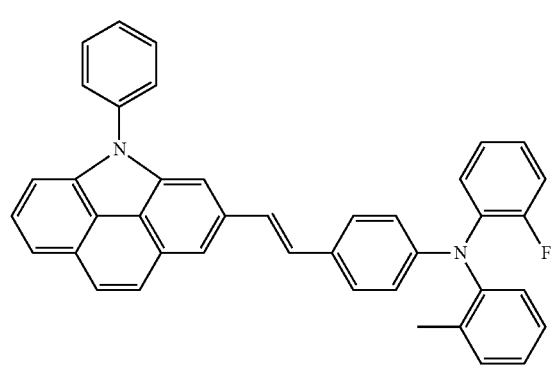
8
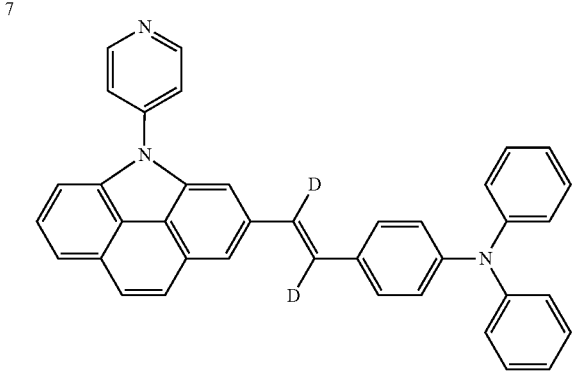
9
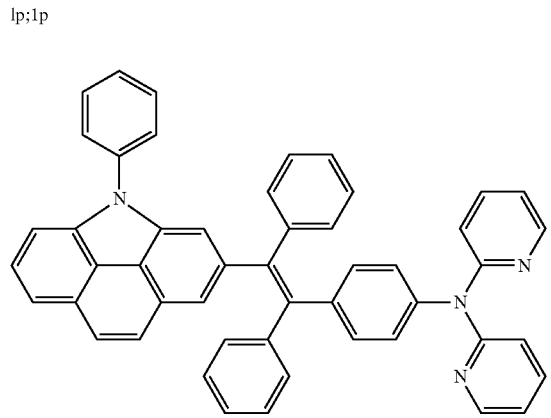
10
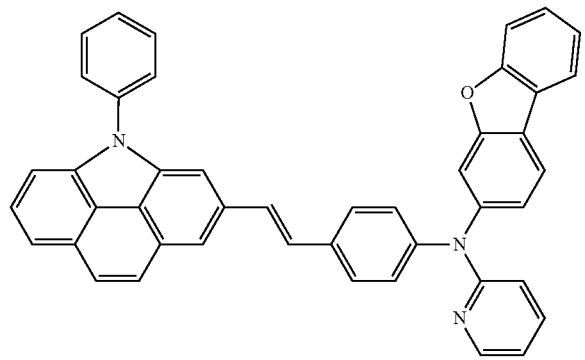

-continued
11
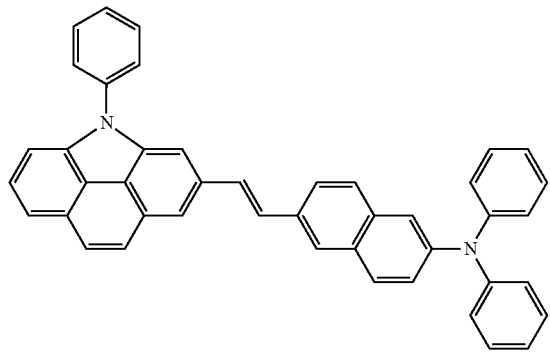
12
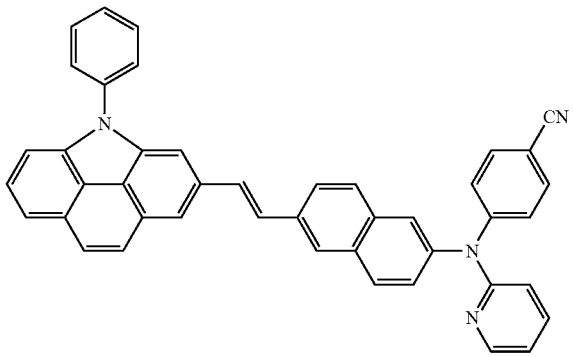
13
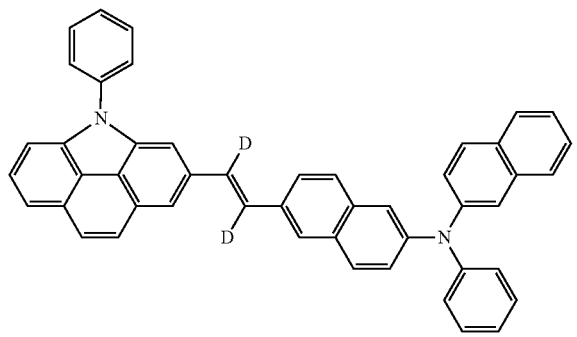
14
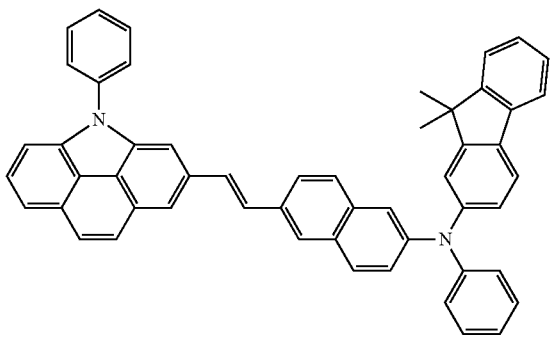
15
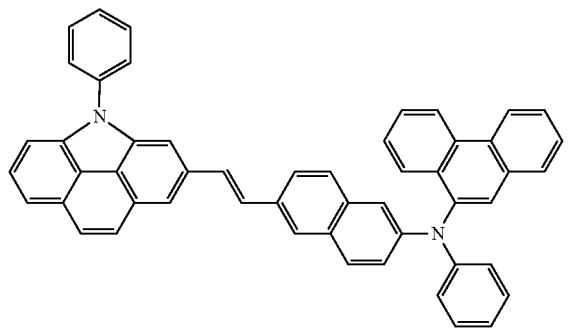
16
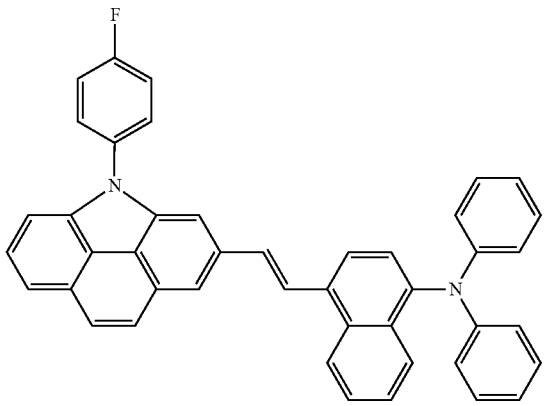
17
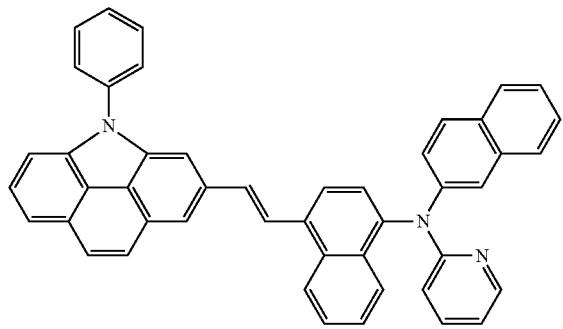
18
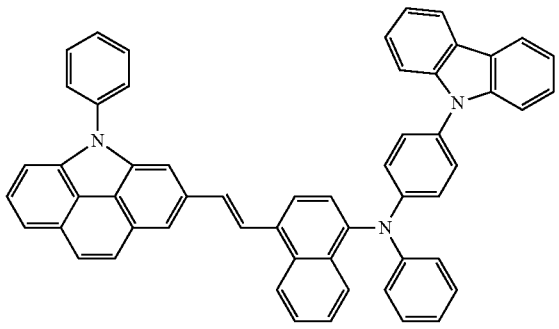

-continued
19
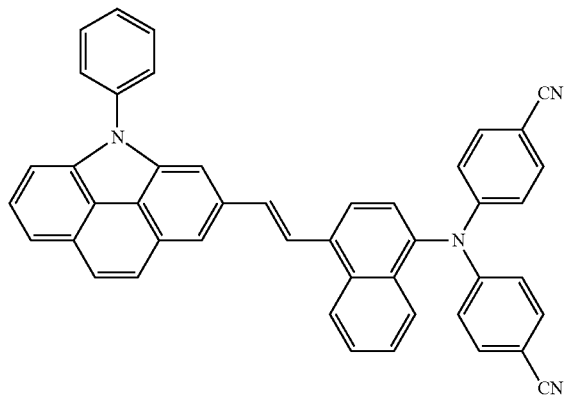
20
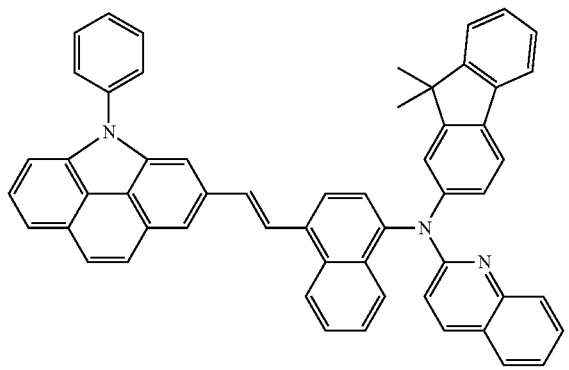
21
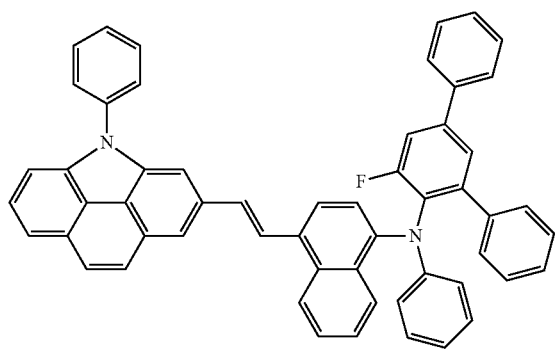
22
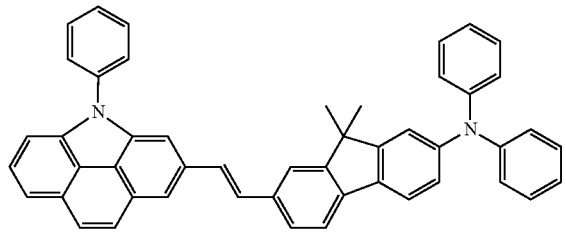
23
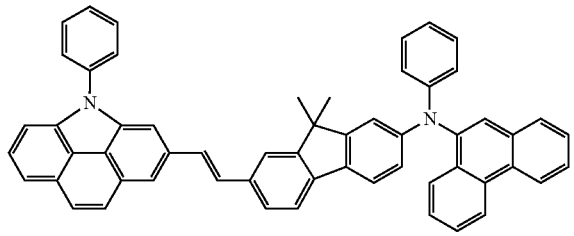
24
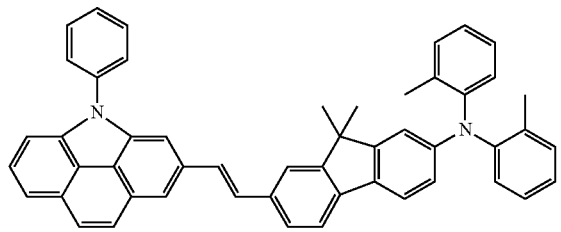
25
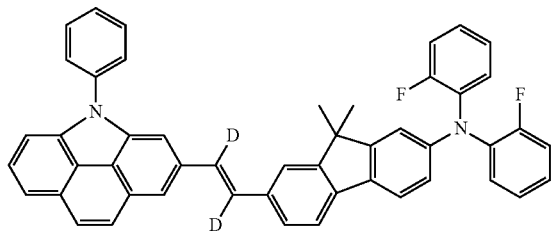
26
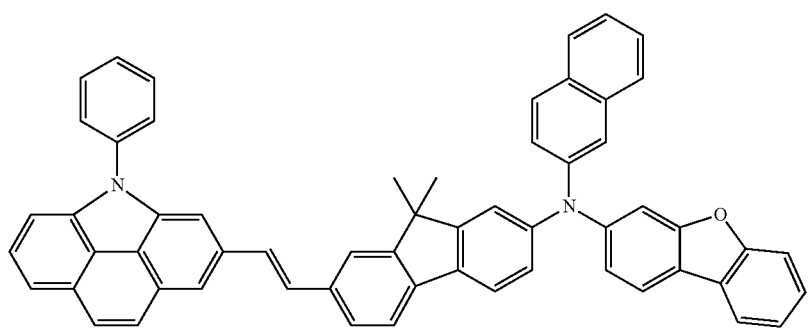

-continued
28
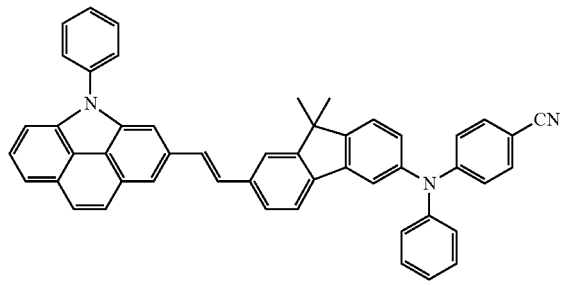
27
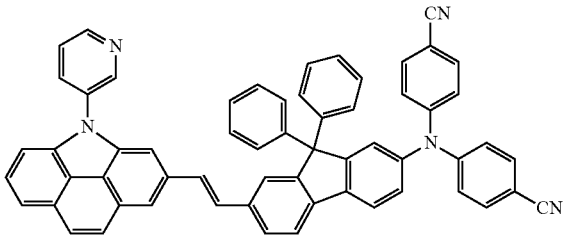
29
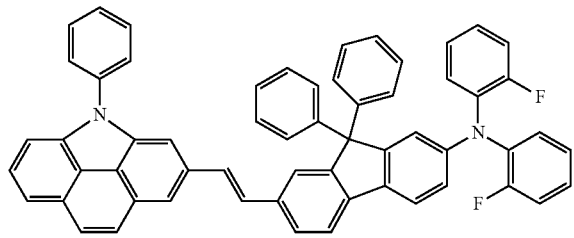
30
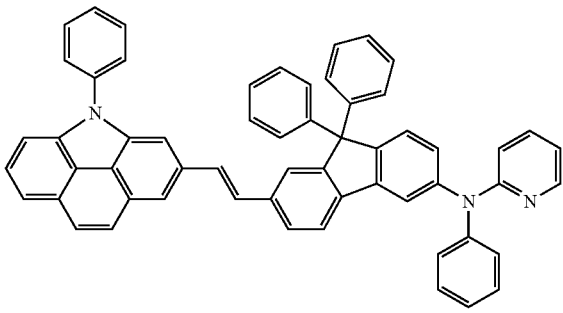
31
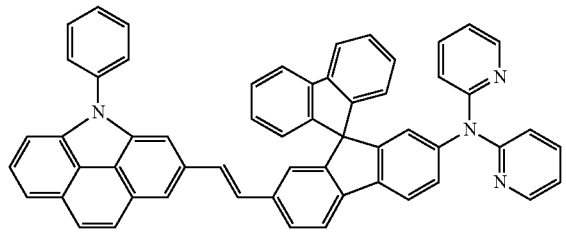
32
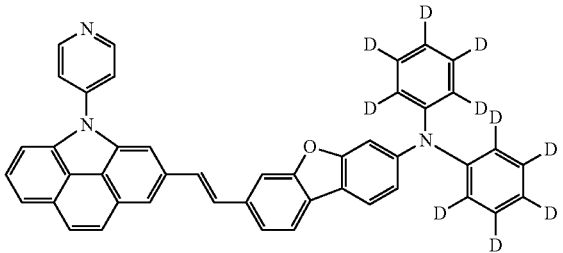
33
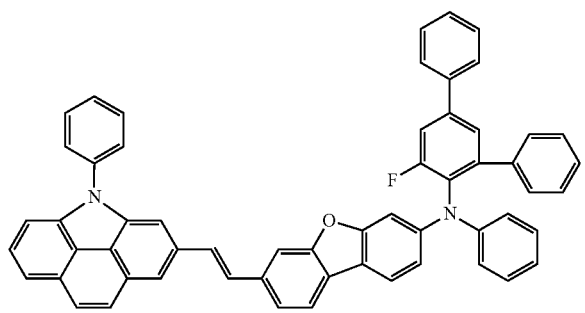
34
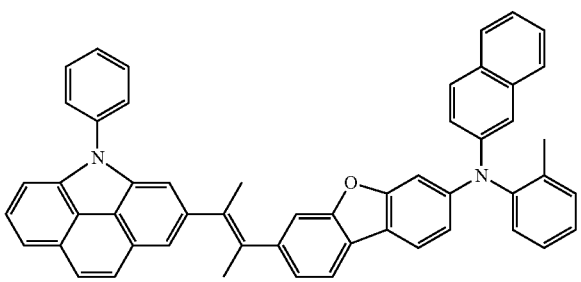
35
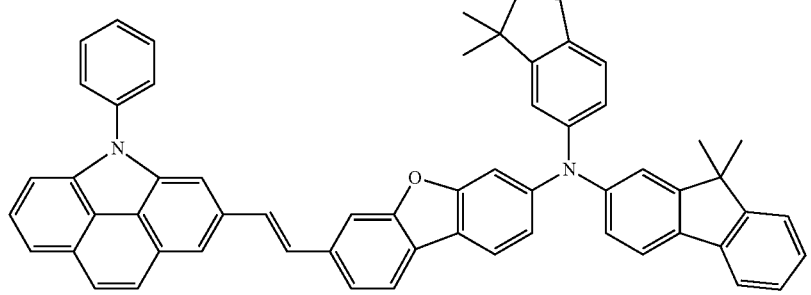

-continued
36
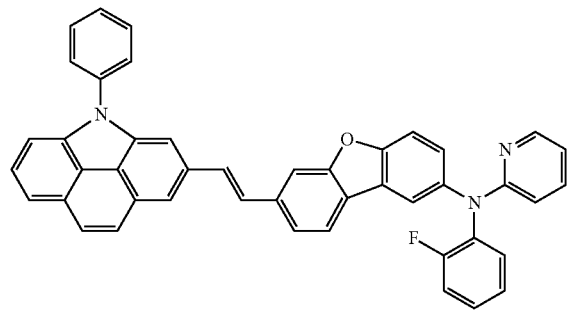
37
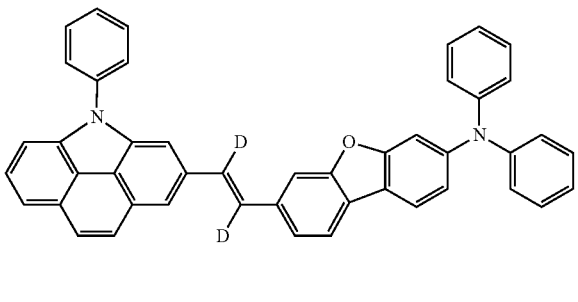
38
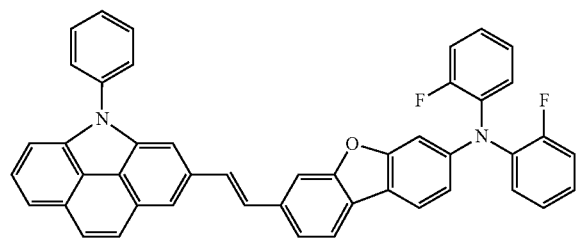
39
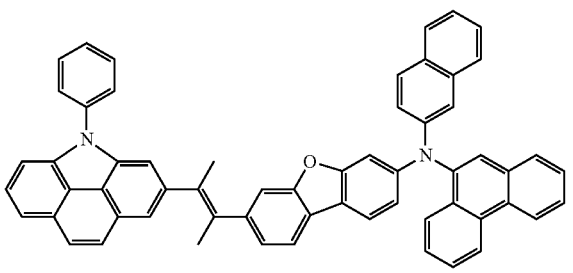
40
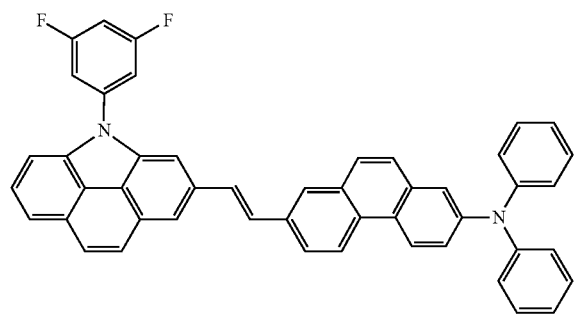
41
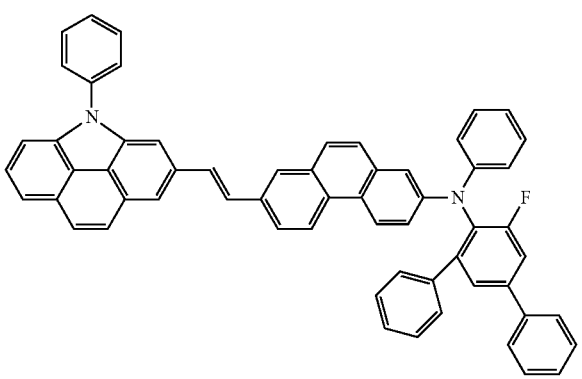
42
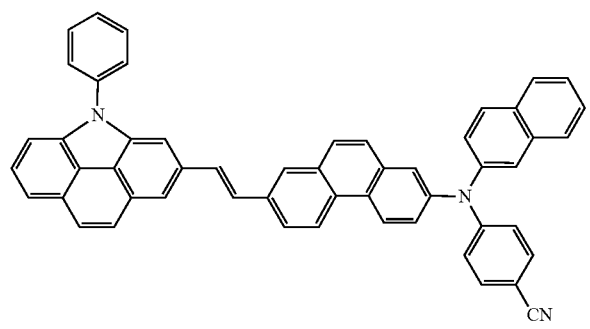
43
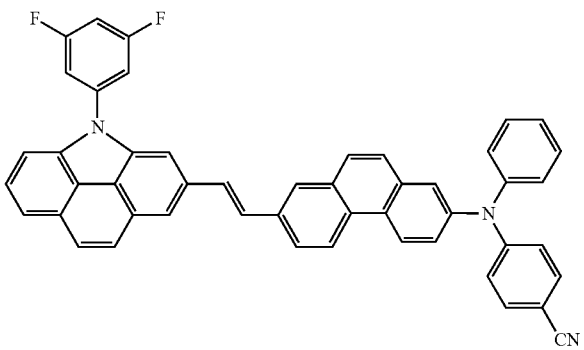

-continued
44
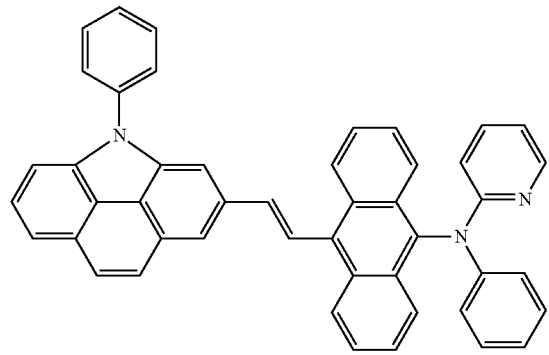
45
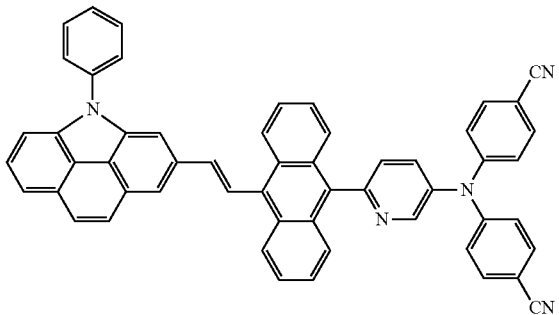
46
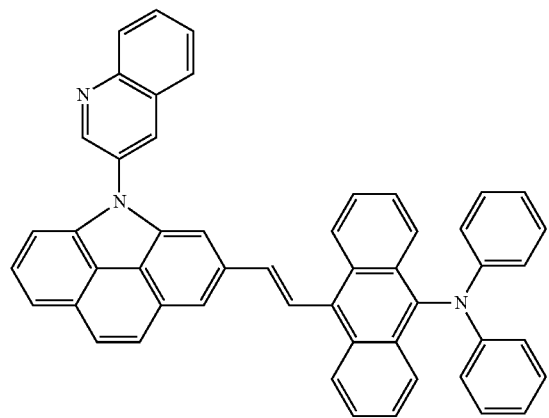
47
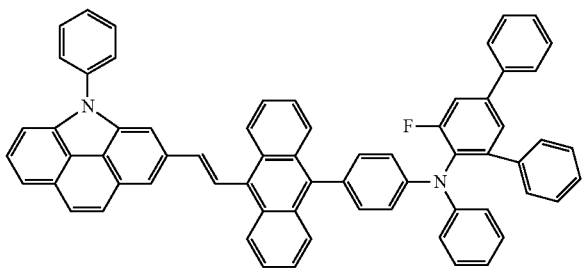
48
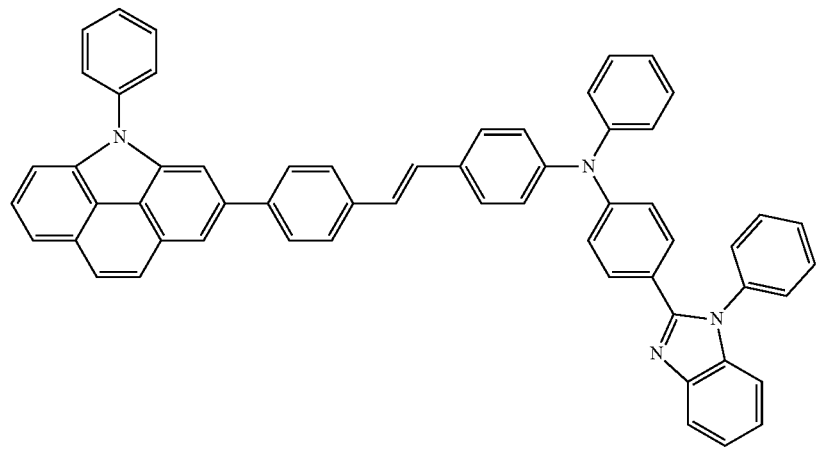
49
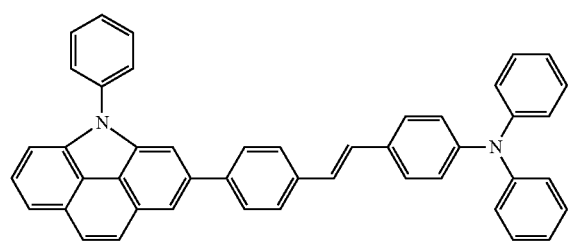

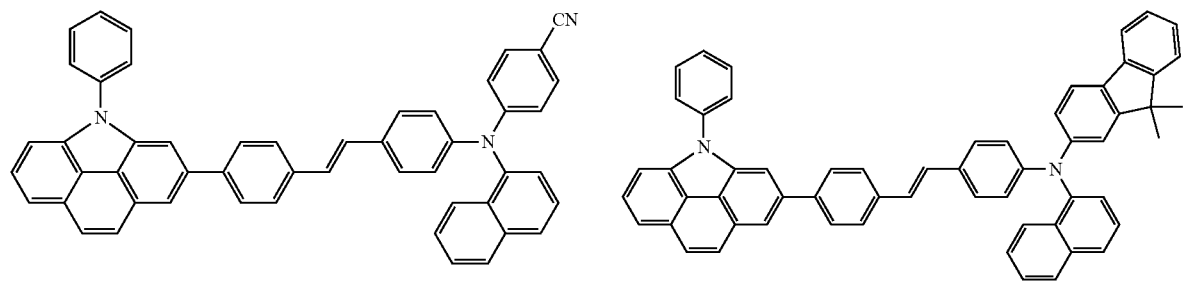
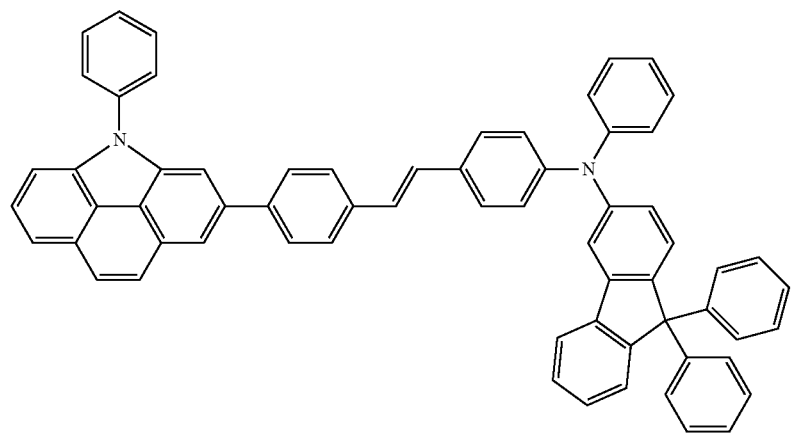
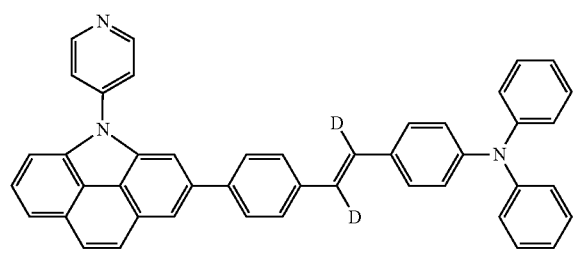
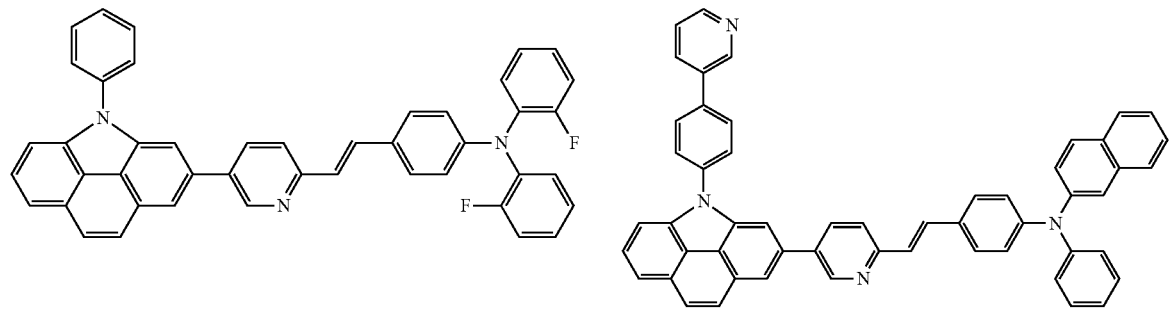

-continued
56
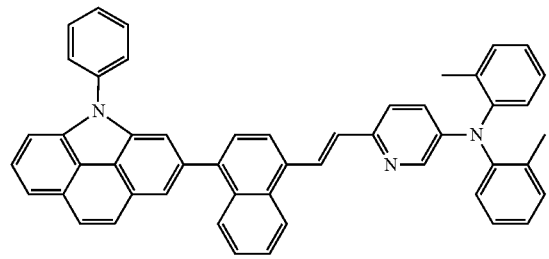
57
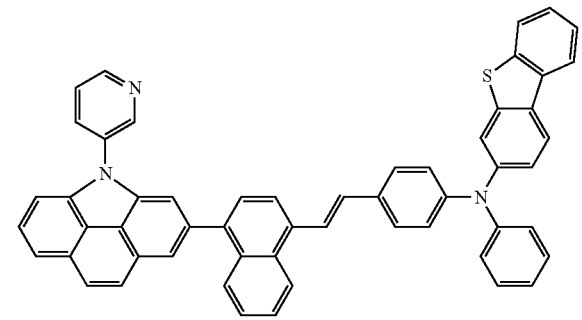
58
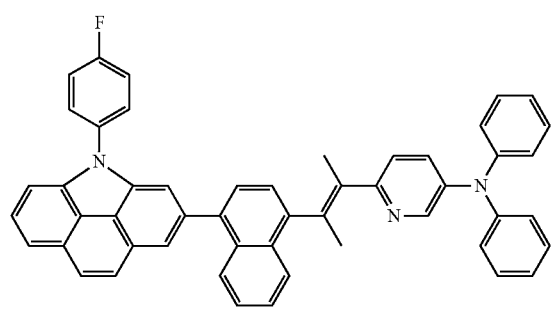
59
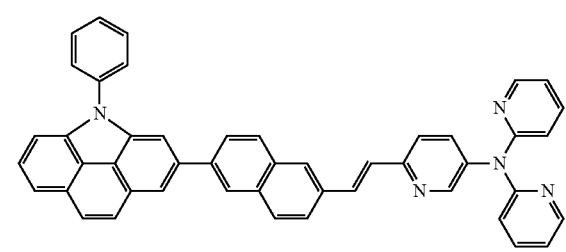
60
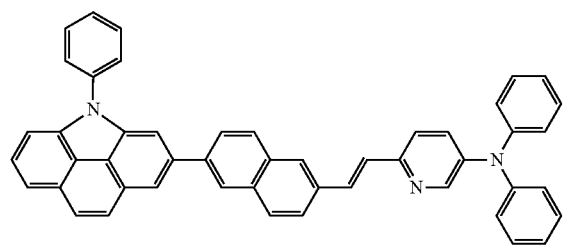
61
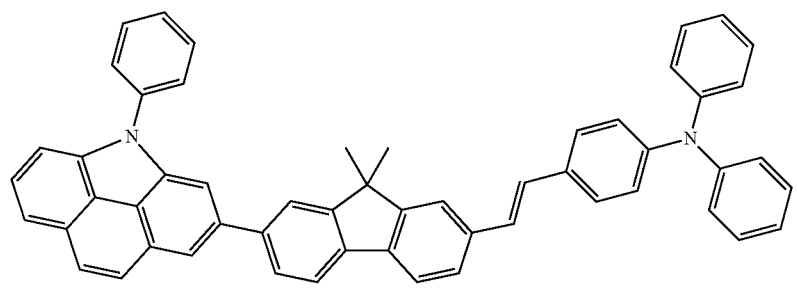
62
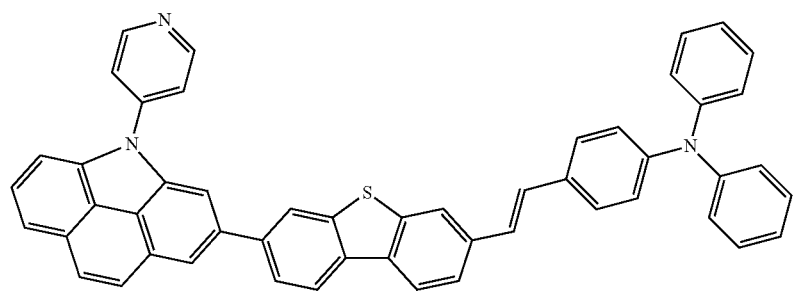

-continued
63
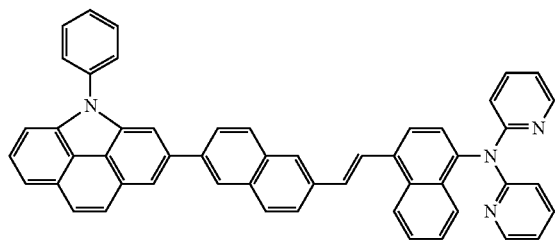
64
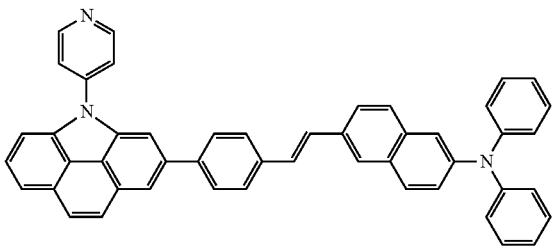
65
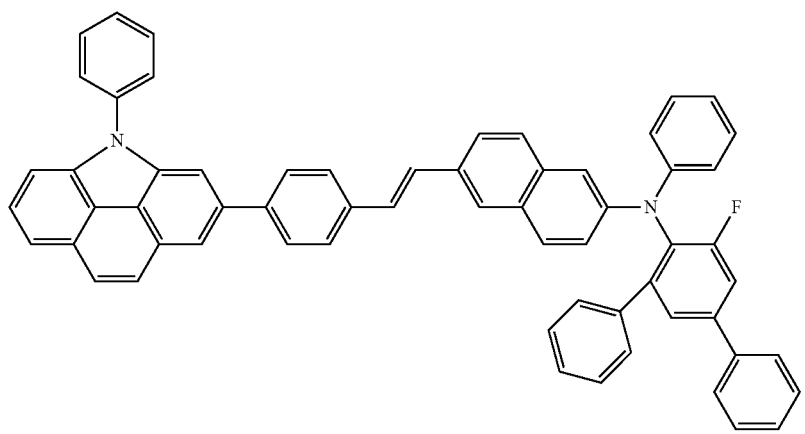
66
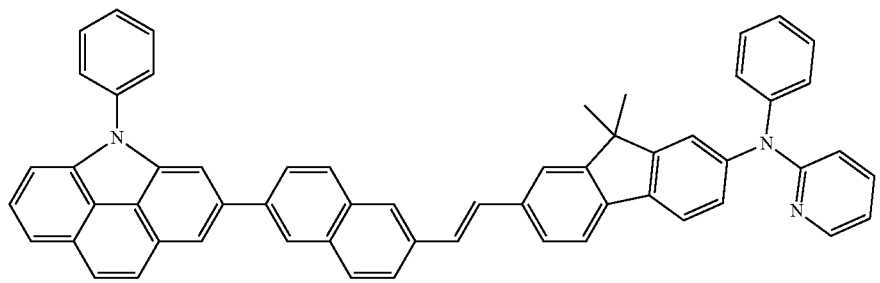
67
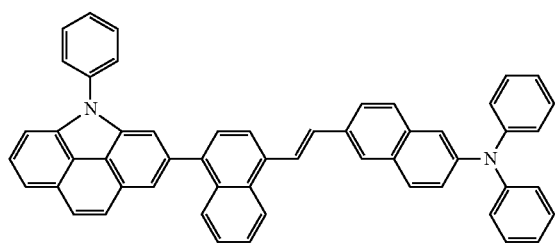
68
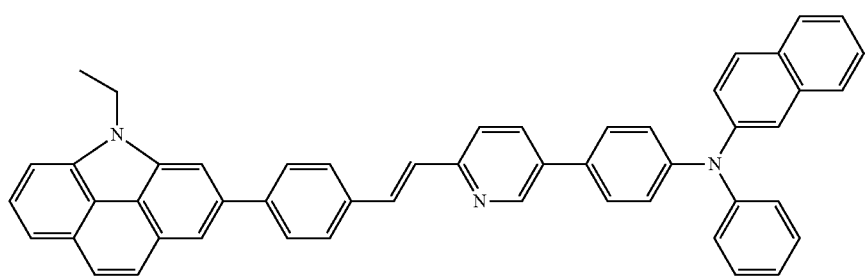

-continued
69
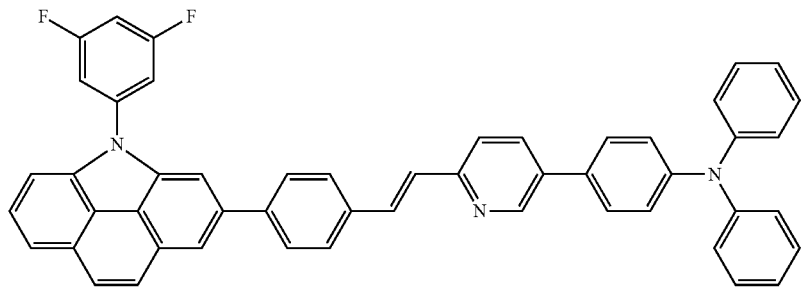
70
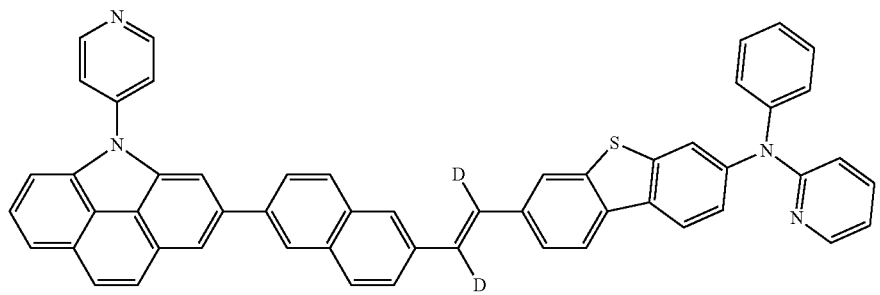
71
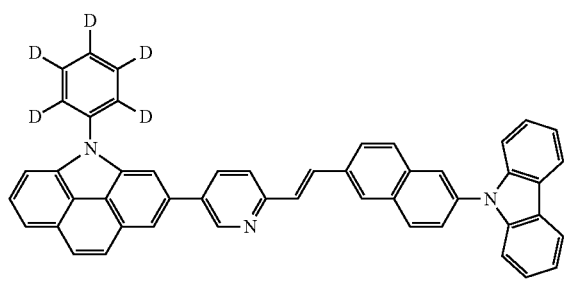
72
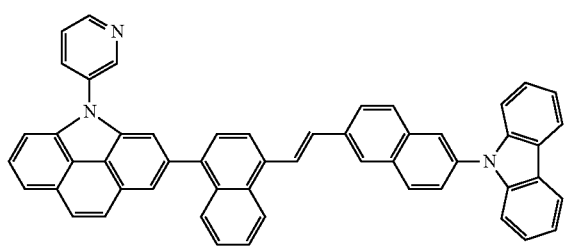
73
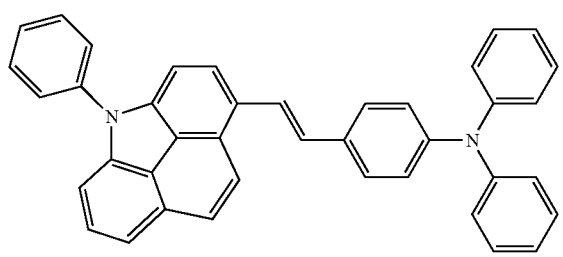
74
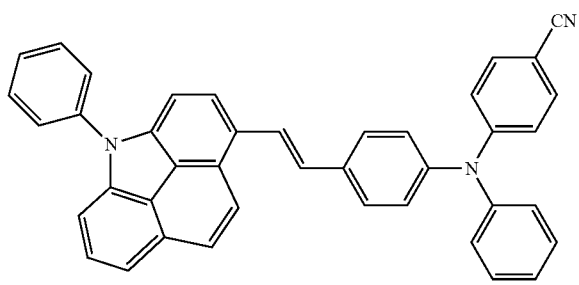
75
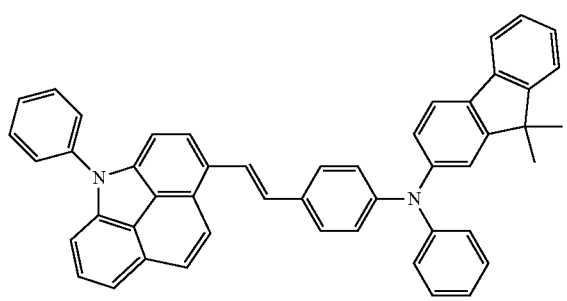
76
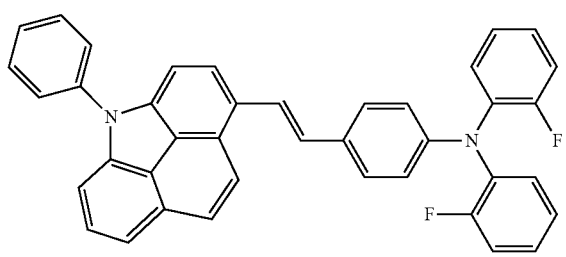

-continued
77
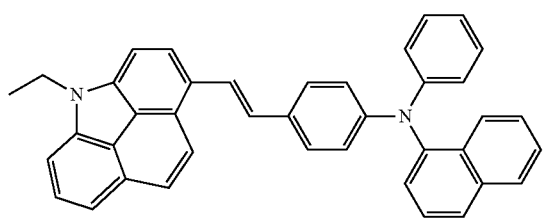
78
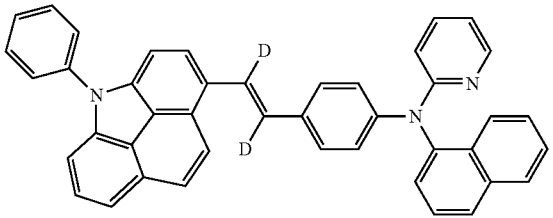
79
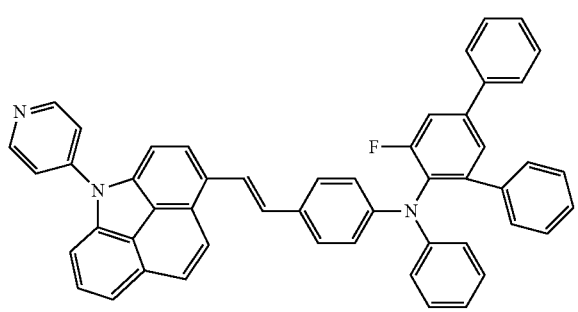
80
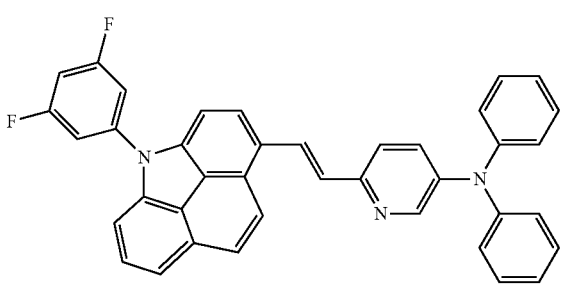
81
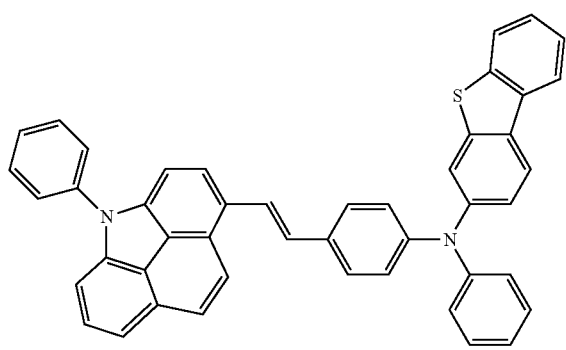
82
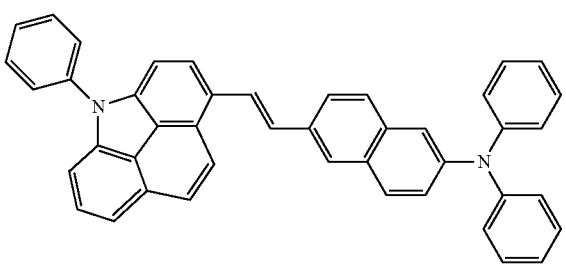
83
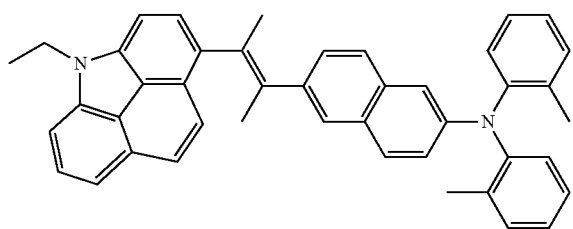
84
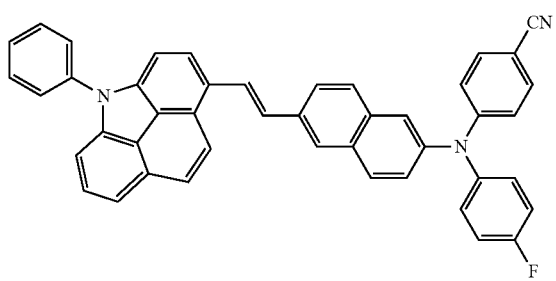
85
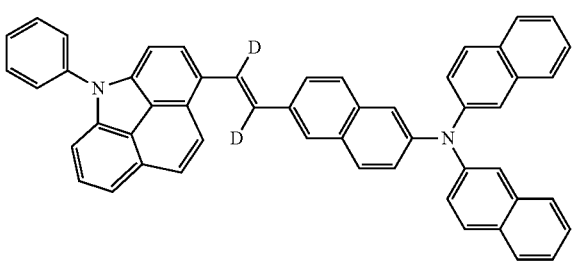

-continued
86
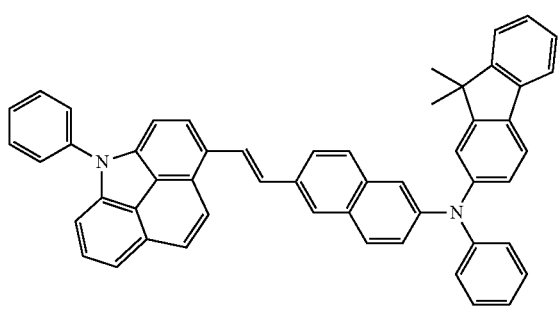
87
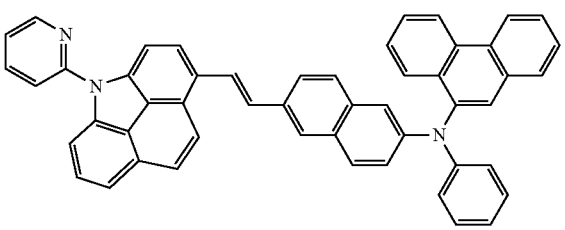
88
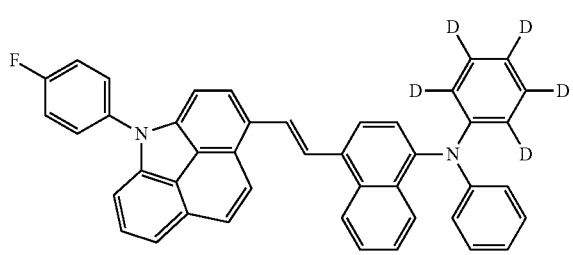
89
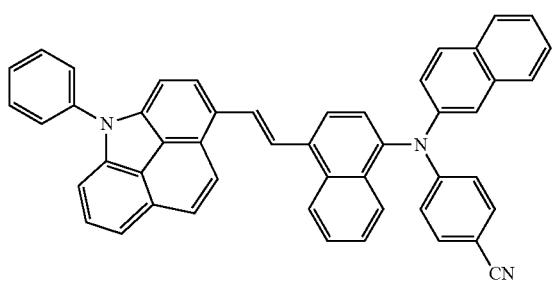
90
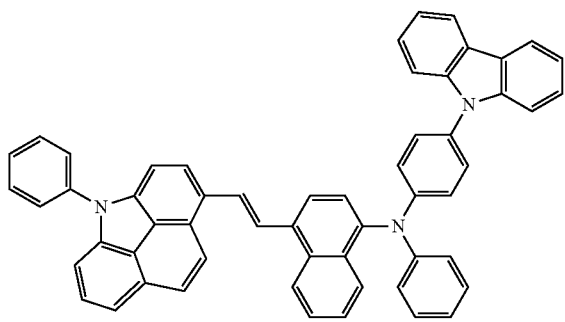
91
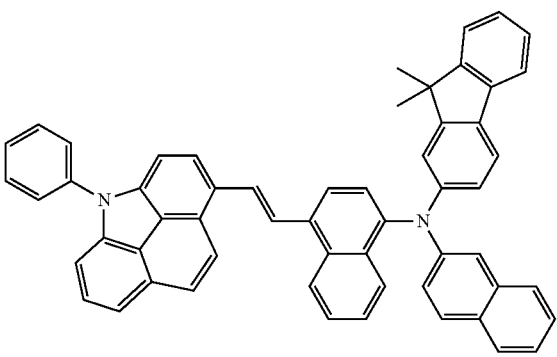
92
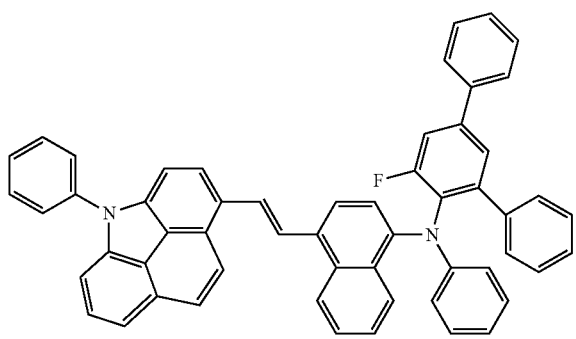
93
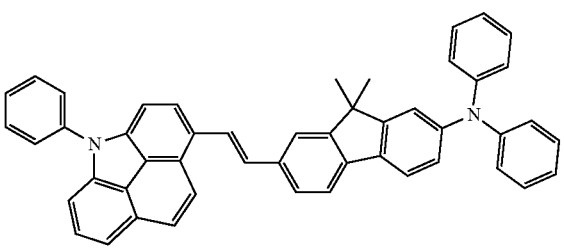

94
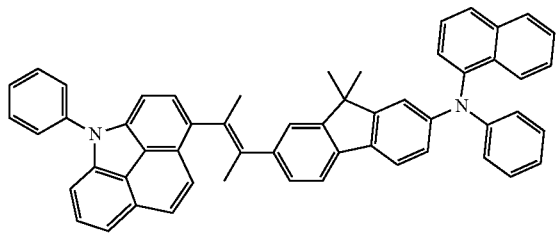
95
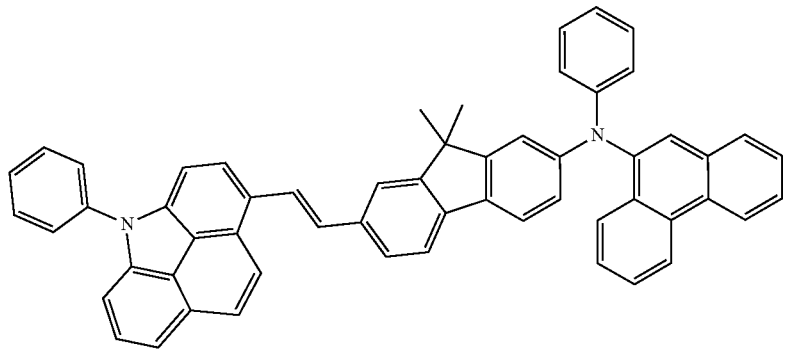
96
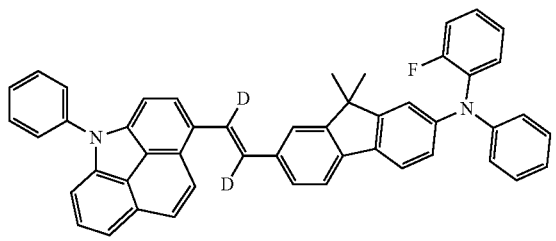
97
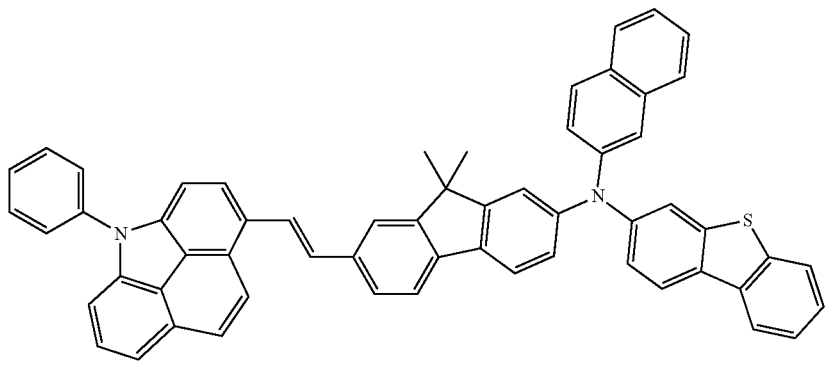
98
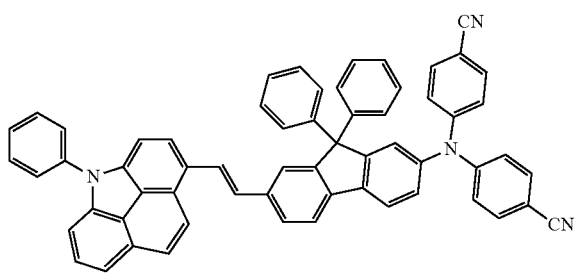
99
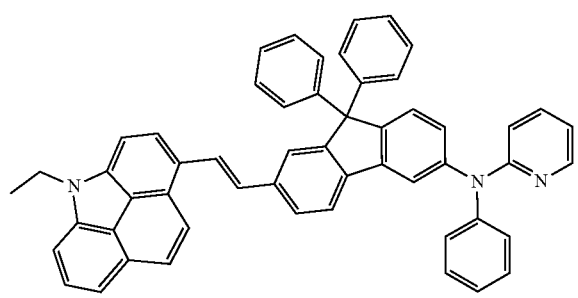

-continued
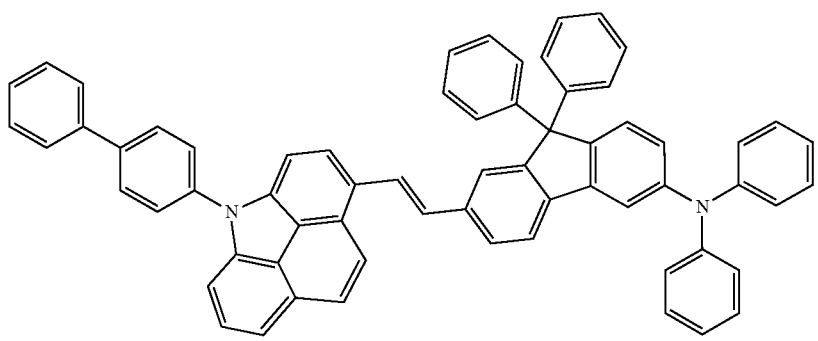
100
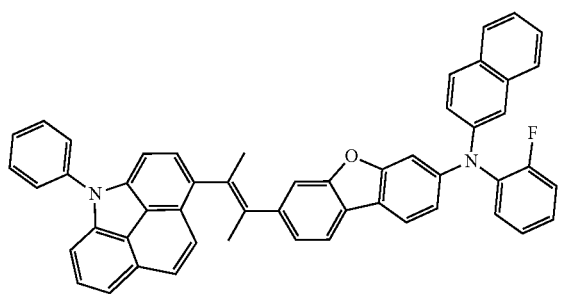
101
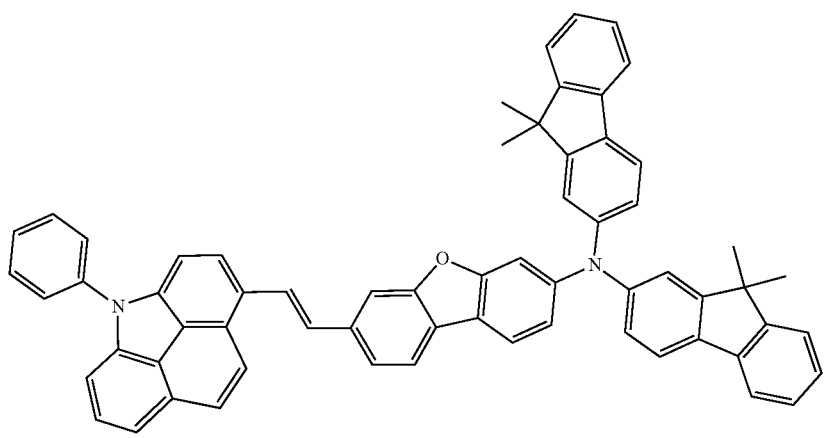
102
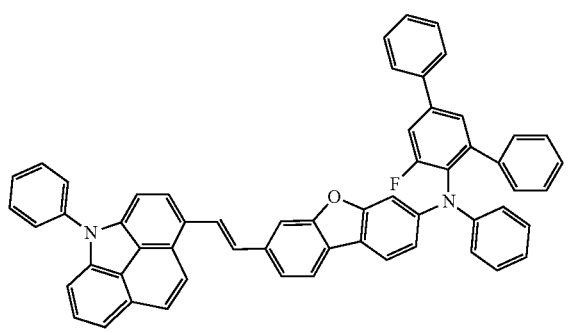
103
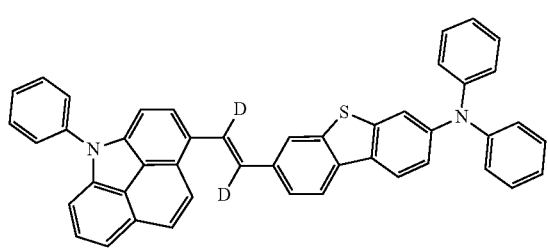
104

-continued
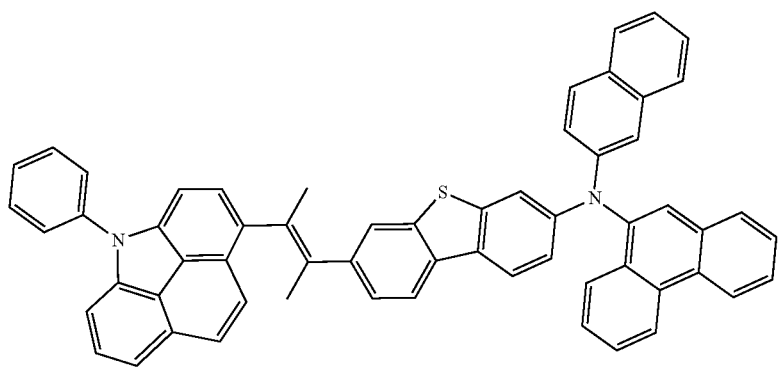
105
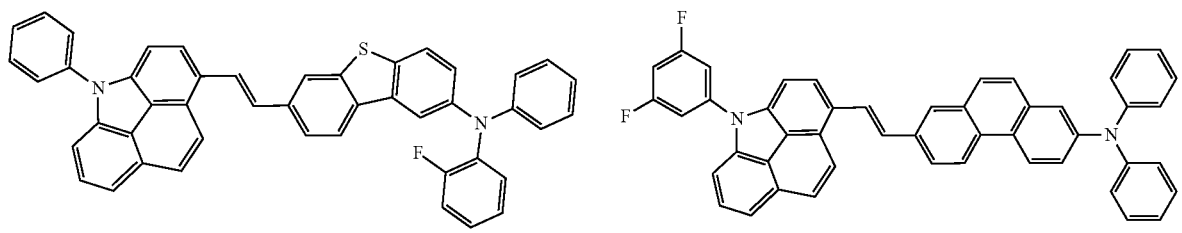
106 107
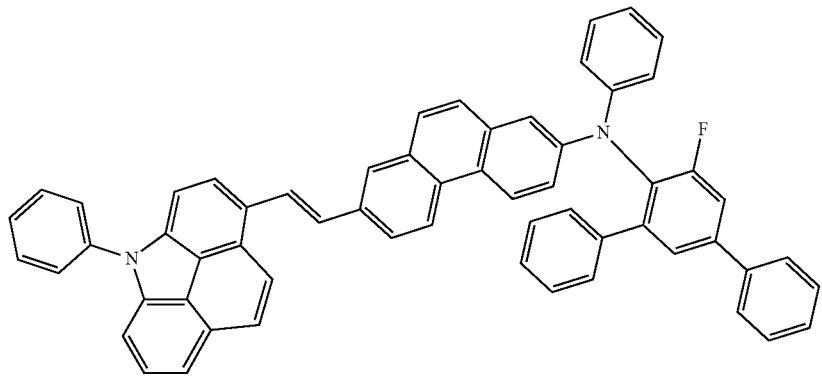
108
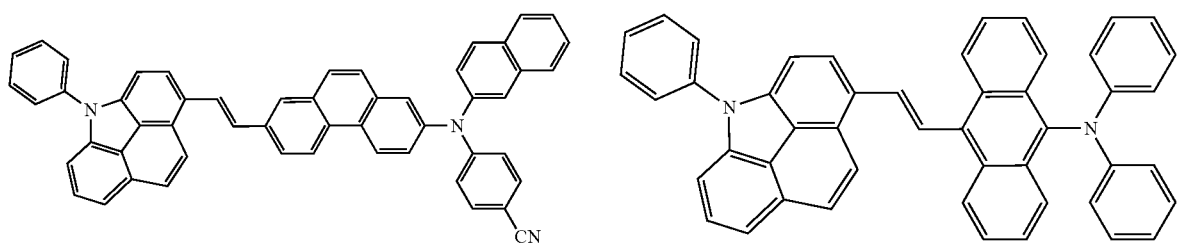
109 110
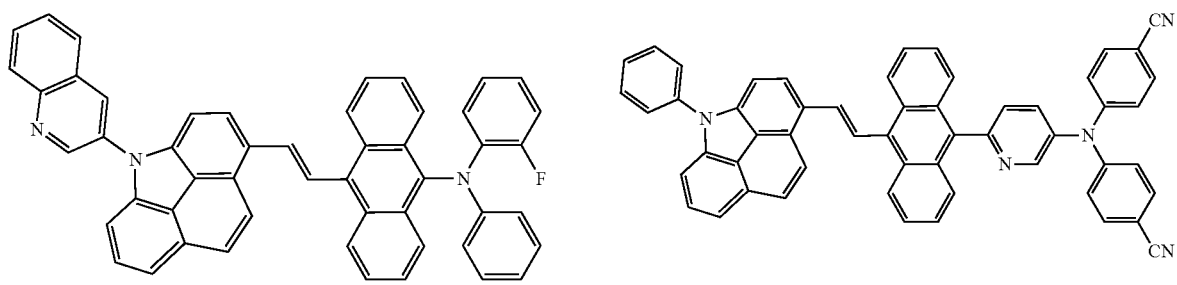
111 112

-continued
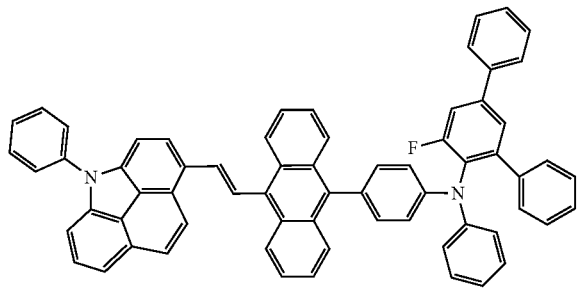
113
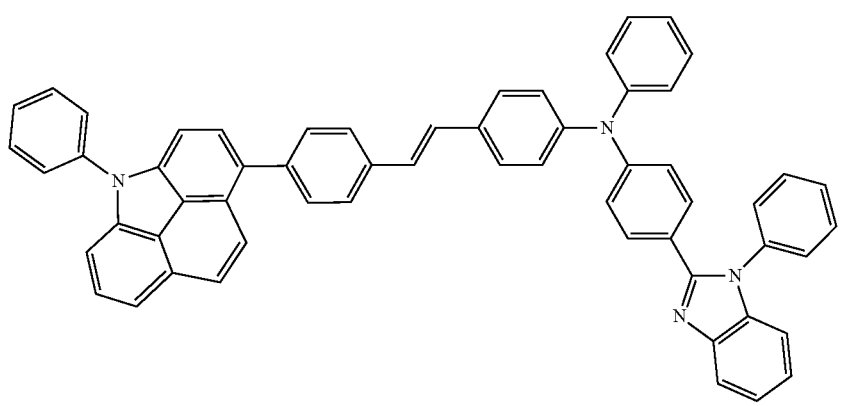
114
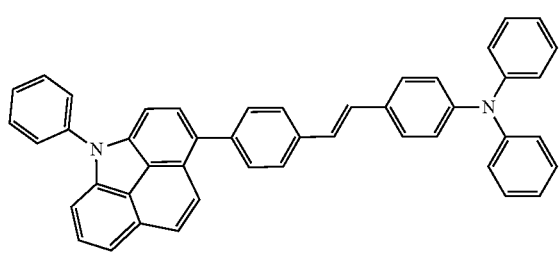
115
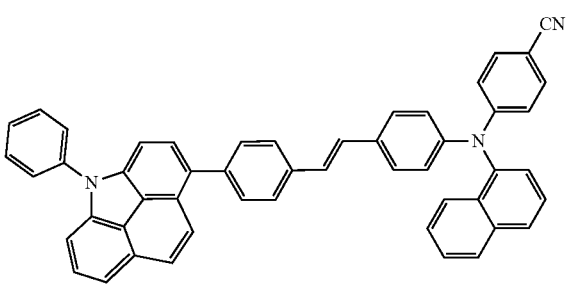
116
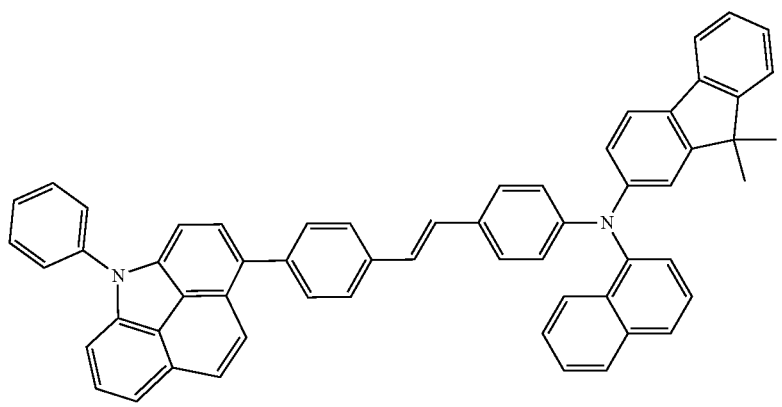
117

-continued
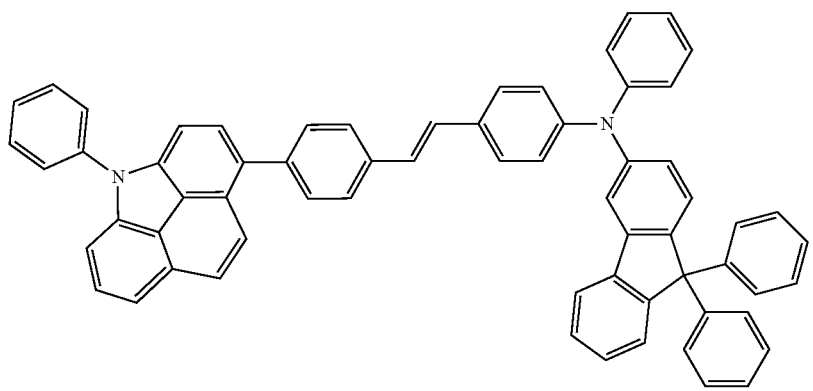
118
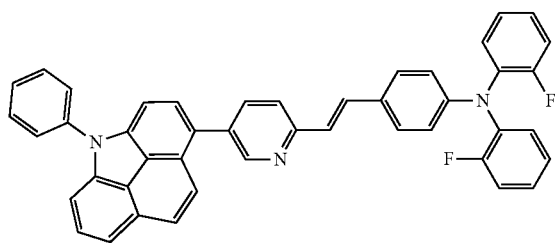
119
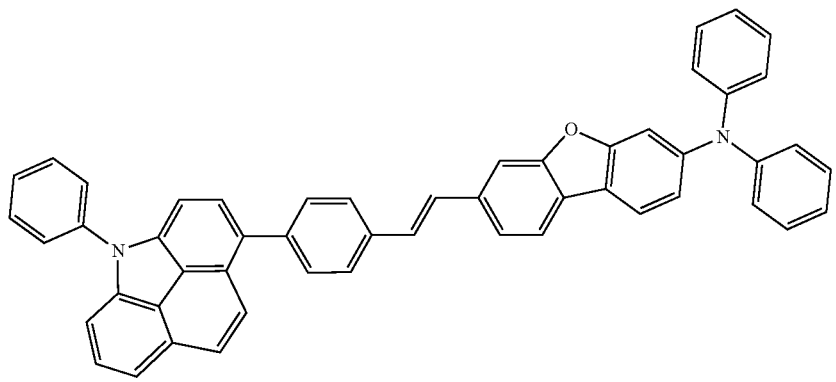
120
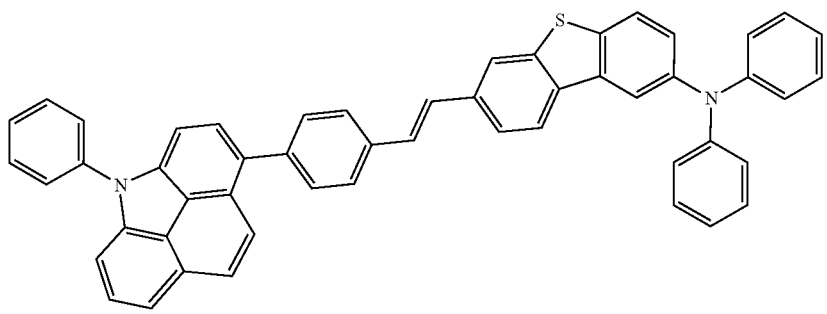
121

-continued
122
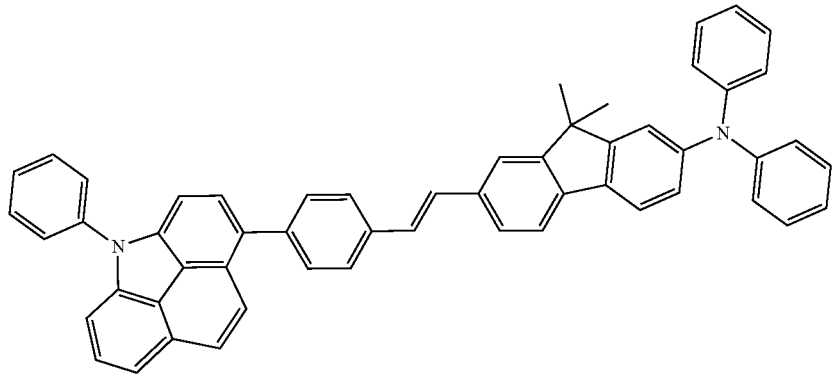
123
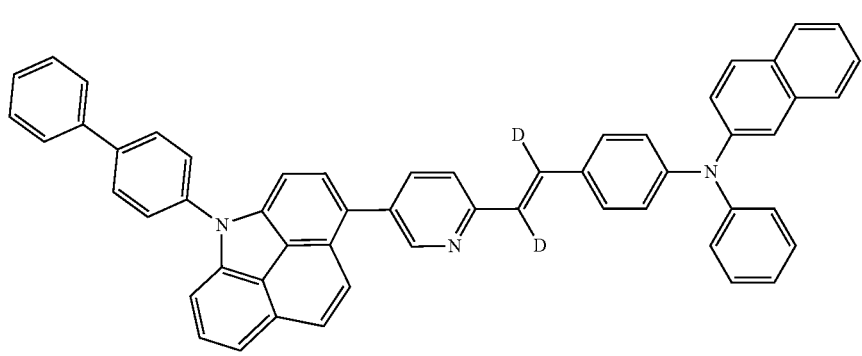
124
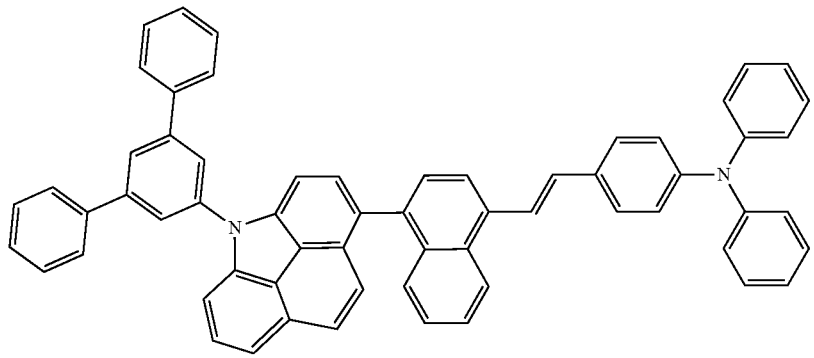
125
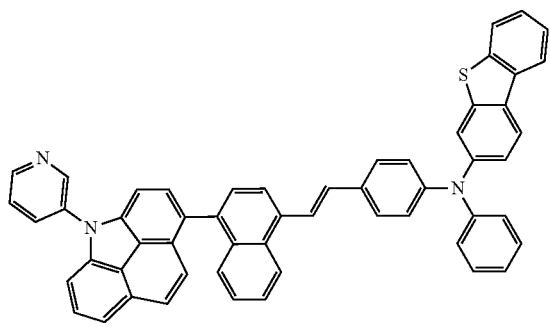
126
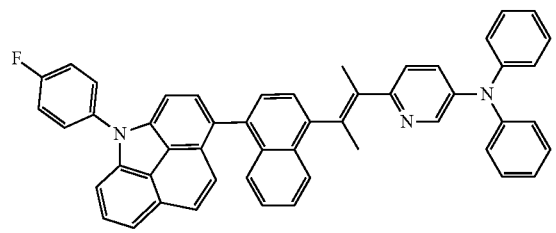
127
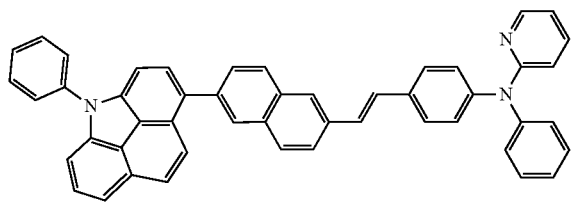

128
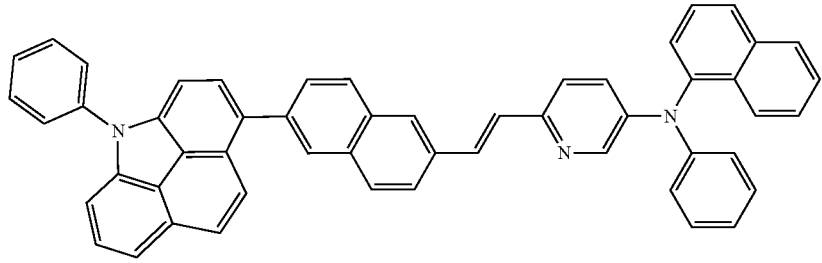
129
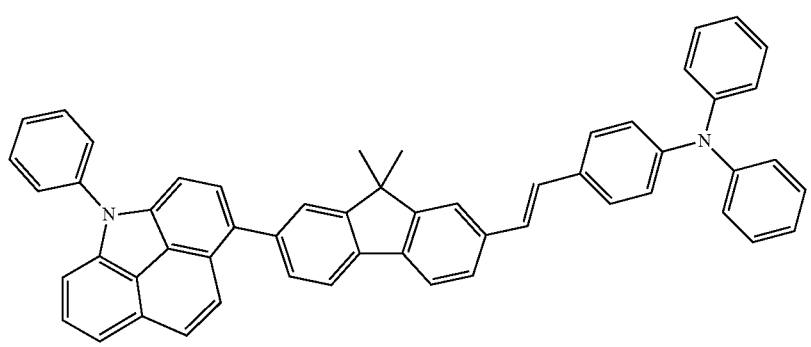
130
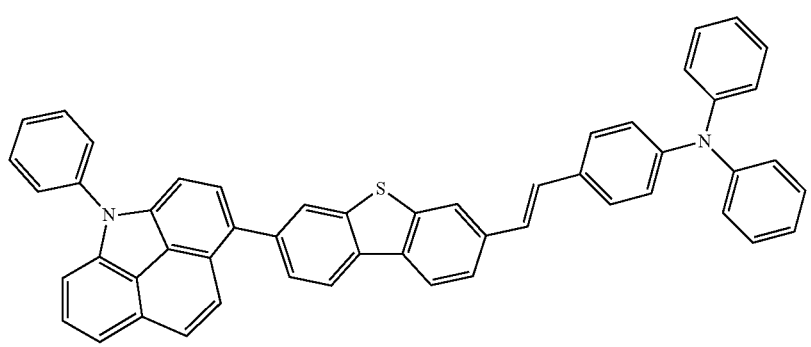
131
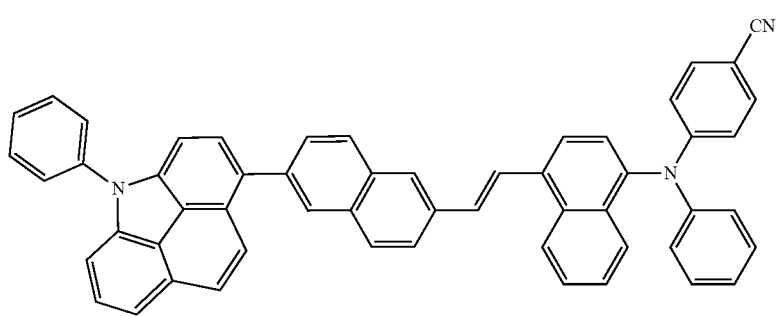
132
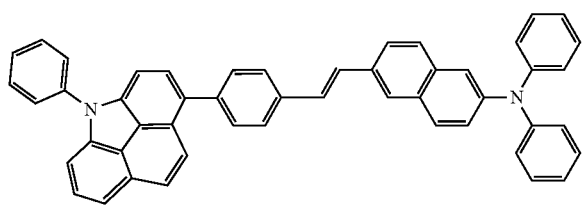

133
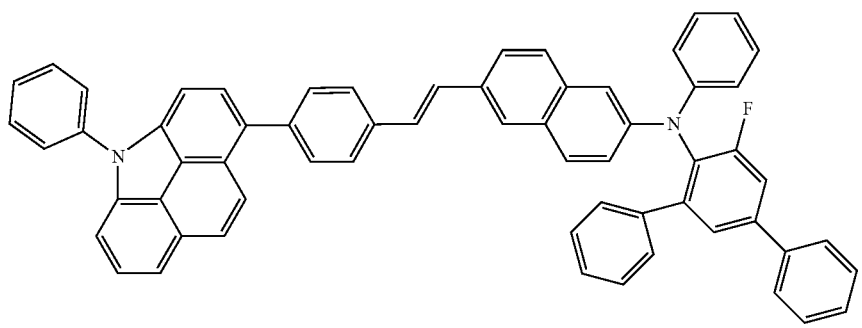
134
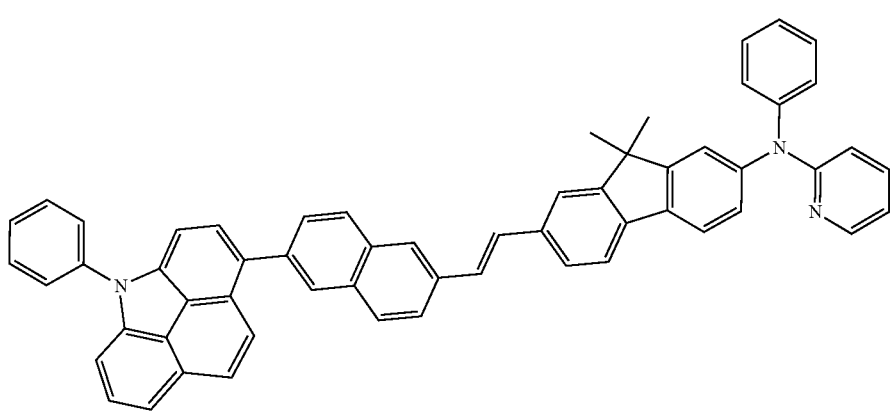
135
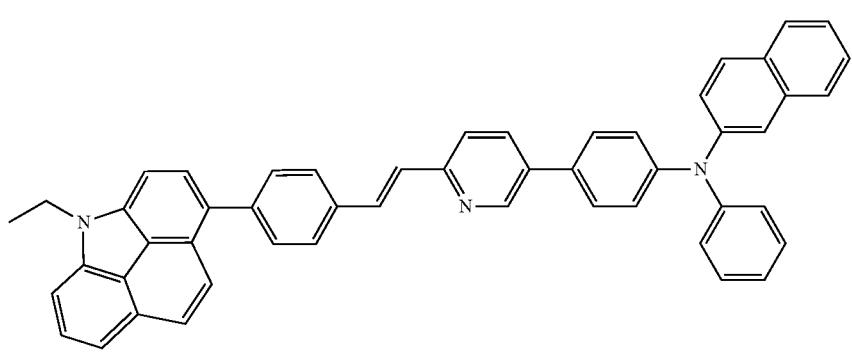
136
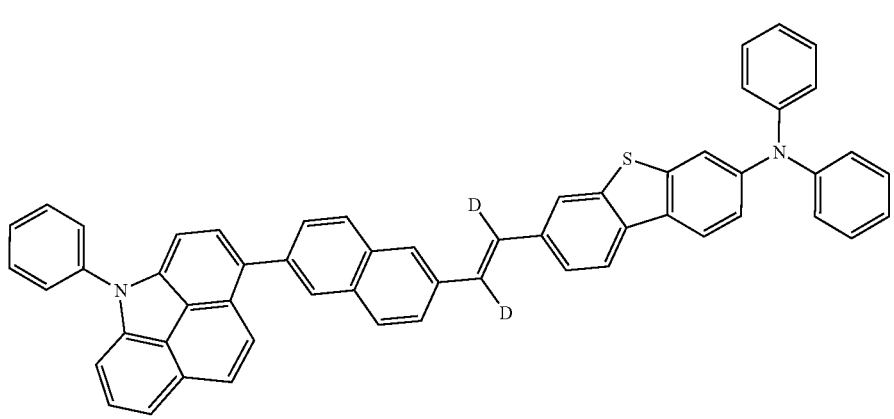

137

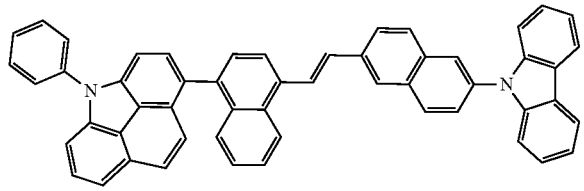

10. An organic light-emitting diode (OLED) comprising:
a first electrode;
a second electrode; and
an organic layer between the first electrode and the second electrode, the organic layer comprising the compound of claim 1.

11. The OLED of claim 10, wherein the organic layer is an emission layer.

12. The OLED of claim 10, wherein the organic layer comprises an emission layer, and one or more of an electron injection layer, an electron transport layer, a functional layer having both electron injection and electron transport capabilities, a hole injection layer, a hole transport layer, or a functional layer having both hole injection and hole transport capabilities,
wherein the emission layer comprises the compound represented by Formula 1, and
the emission layer further comprises an anthracene-based compound, an arylamine-based compound, or a styryl-based compound.

13. The OLED of claim 10, wherein the organic layer comprises an emission layer, and one or more of an electron injection layer, an electron transport layer, a functional layer having both electron injection and electron transport capabilities, a hole injection layer, a hole transport layer, or a functional layer having both hole injection and hole transport capabilities,
wherein the emission layer comprises the compound represented by Formula 1, and
one or more of a red emission layer, a green emission layer, a blue emission layer, or a white emission layer of the emission layer comprises a phosphorescent compound.

14. The OLED of claim 13, wherein the hole injection layer, the hole transport layer, or the functional layer having both hole injection and hole transport capabilities comprises a charge-generating material.

15. The OLED of claim 14, wherein the charge-generating material is a p-dopant.

16. The OLED of claim 15, wherein the p-dopant is a quinone derivative, a metal oxide, or a cyano group-containing compound.

17. The OLED of claim 10, wherein the organic layer comprises an electron transport layer, and the electron transport layer comprises a metal complex.

18. The OLED of claim 17, wherein the metal complex is a lithium (Li) complex.

19. The OLED of claim 10, wherein the organic layer comprising the compound represented by Formula 1 is formed by a wet process.

20. A flat panel display device, comprising the OLED of claim 10, wherein the first electrode of the OLED is electrically connected to a source electrode or a drain electrode of a thin film transistor (TFT).

* * * * *